US011766417B2

(12) United States Patent
Ari D'Agostino et al.

(10) Patent No.: US 11,766,417 B2
(45) Date of Patent: *Sep. 26, 2023

(54) EXOGENOUS KETONE SUPPLEMENTS FOR REDUCING ANXIETY-RELATED BEHAVIOR

(71) Applicant: University of South Florida, Tampa, FL (US)

(72) Inventors: Csilla Ari D'Agostino, Tampa, FL (US); Dominic Paul D'Agostino, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 55 days.

This patent is subject to a terminal disclaimer.

(21) Appl. No.: 17/234,382

(22) Filed: Apr. 19, 2021

(65) Prior Publication Data
US 2021/0236452 A1 Aug. 5, 2021

Related U.S. Application Data

(63) Continuation of application No. 15/422,091, filed on Feb. 1, 2017, now Pat. No. 10,980,764.
(Continued)

(51) Int. Cl.
*A61K 31/22* (2006.01)
*A61K 31/23* (2006.01)
(Continued)

(52) U.S. Cl.
CPC .............. *A61K 31/22* (2013.01); *A23L 33/12* (2016.08); *A23L 33/16* (2016.08); *A23L 33/30* (2016.08);
(Continued)

(58) Field of Classification Search
CPC ....... A61K 31/22; A61K 9/0053; A61K 31/19
See application file for complete search history.

(56) References Cited

U.S. PATENT DOCUMENTS

| 2008/0058416 A1 | 3/2008 | Greenwood |
| 2015/0132280 A1 | 5/2015 | Lopez et al. |
| 2015/0344413 A1 | 12/2015 | Araujo et al. |

OTHER PUBLICATIONS

Albert, C.M. et al., Phobic anxiety and risk of coronary heart disease and sudden cardiac death among women, Circulation, Feb. 1, 2005;111(4):480-7.
(Continued)

*Primary Examiner* — San Ming R Hui
(74) *Attorney, Agent, or Firm* — Meunier Carlin & Curfman LLC

(57) ABSTRACT

Methods of treating anxiety disorders or reducing anxiety-related behaviors. The methods include administering a therapeutically effective amount of ketone supplementation, such as butanediol, ketone esters (e.g., 1,3-butanediol-acetoacetate diester) and/or ketone salts (e.g., beta-hydroxybutyrate-mineral salt), chronically, sub-chronically, or acutely, with or without admixture with a medium chain triglyceride or in combination. It was determined herein that ketone supplementation reduced anxiety in rats on elevated plus maze as measured by less entries to closed arms, more time spent in open arms, more distance travelled in open arms, and delayed latency to entrance to closed arms, when compared to control. Along with reducing anxiety-related behavior, the chronic, sub-chronic, and acute ketone supplements also caused significant elevation of blood βHB levels and changed blood glucose levels.

10 Claims, 37 Drawing Sheets

Related U.S. Application Data

(60) Provisional application No. 62/289,749, filed on Feb. 1, 2016.

(51) Int. Cl.
*A61K 31/19* (2006.01)
*A61K 9/00* (2006.01)
*A23L 33/00* (2016.01)
*A23L 33/16* (2016.01)
*A23L 33/12* (2016.01)

(52) U.S. Cl.
CPC .............. *A61K 9/0053* (2013.01); *A61K 31/19* (2013.01); *A61K 31/23* (2013.01); *A23V 2002/00* (2013.01)

(56) References Cited

OTHER PUBLICATIONS

Aucoin, M. et al., Generalized Anxiety Disorder and Hypoglycemia Symptoms Improved with Diet Modification, Case Reports in Psychiatry, Hindawi Publishing Corporation, vol. 2016, Article ID 7165425, 4 pages.
Coenen, A.M. et al., Genetic animal models for absence epilepsy: a review of the WAG/Rij strain of rats, Behav. Genet., 2003,33(6):635-655.
D'Agostino, D. et al., Therapeutic ketosis with ketone ester delays central nervous system oxygen toxicity seizures in rats, American Journal of Physiology, Regulatory, integrative and comparative physiology, 2013,304(10):R829-36.
De Giorgis, V. et al., GLUT1 Deficiency Syndrome 2013: Current State of the Art, 2013, 22 (10): 803-811.
Dias, B.G. et al., Towards new approaches to disorders of fear and anxiety, Curr Opin Neurobiol, Jun. 2013;23(3): 346-52.
Domes, F.V. et al., The anxiolytic-like effects of cannabidiolinjected into the bed nucleus of the stria terminalis are mediated by 5-HT1Areceptors, Psychopharmacology (Berl), Feb. 2011;213(2-3):465-73.
Ehrenreich, M.J., A case of the re-emergence of panic and anxiety symptoms after initiation of a high-protein, very low carbohydrate diet, Psychosomatics, Mar.-Apr. 2006;47(2):178-9.
Engin, E. et al., The effects of intra-cerebral drug infusions on animals' unconditioned fear reactions: a systematic review, Prog Neuropsychopharmacol Biol Psychiatry, Aug. 1, 2008;32(6):1399-419.
Ferguson, S.A. et al., Aging effects on elevated plus maze behavior inspontaneously hypertensive, Wistar-Kyoto and Sprague-Dawley male and female rats, Physiol Behav, Aug. 7, 2005; 85(5): 621-8.
Gilpin et al., Biol Psychiatry, 2015;77(10):859-869 (Year: 2015). *
Greenberg, P.E. et al., The economic burden of anxiety disorders in the 1990s, J Clin Psychiatry, Jul. 1999;60(7):427-35.
Guimaraes, F.S. et al., Antianxiety effect of cannabidiol in the elevated plus-maze, Psychopharmacology (Berl), 1990;100(4):558-9.
Guimaraes, F.S. et al., Anxiolytic effect in the elevated plus-maze of the Nmda receptor antagonist AP7 microinjected into the dorsal periaqueductal grey, Psychopharmacology (Berl), 1991;103(1):91-4.
Hamid, H. et al. Anxiety symptoms in epilepsy: salient issues for future research, Epilepsy Behav, 2011; 22:63-68.
Hettema, J. M. et al., The nosologic relationship between generalized anxiety disorder and major depression, Depress. Anxiety, 2008; 25, 300-31610.
Johansson, B. et al., Hyperalgesia, anxiety, and decreased hypoxic neuroprotection in mice lacking the adenosine A1 receptor, Proc Natl Acad Sci U S A, Jul. 31, 2001;98(16):9407-12. Epub Jul. 24, 2001.
Kakui, N. et al., Anxiolytic-like profile of mirtazapine in rat conditioned fear stress model: Functional significance of 5-hydroxytryptamine 1A receptor and alpha1-adrenergic receptor, Pharmacol Biochem Behav, May 2009;92(3):393-8.
Kashiwaya, Y. et al., A ketone ester diet exhibits anxiolytic and cognition-sparing properties, and lessens amyloid and tau pathologies in a mouse model of Alzheimer's disease, Neurobiology of Aging, 2013; 34:1530-1539.
Kessler, R.C. et al., Prevalence, severity, and comorbidity of 12-month DSM-IV disorders in the National Comorbidity Survey Replication. Arch. Gen. Psychiatry, Jun. 2005,62 (6): 617-627.
Klein, E. et al., Anxiogenic effects of m-CPP in patients with panic disorder: comparison to caffeine's anxiogenic effects, Biol Psychiatry, Nov. 15, 1991;30(10):973-84.
Klepper, J. et al., Facilitated glucose transporter protein type 1 (GLUT1) deficiency syndrome: impaired glucose transport into brain—a review, Eur JPediatr, Jun. 2002;161(6):295-304. Epub Apr. 16, 2002. Review.
Kovacs, Z. et al., Absence epileptic activity changing effects of non-adenosine nucleoside inosine, guanosine and uridine in Wistar Albino Glaxo Rijswijk rats, Neuroscience, Aug. 6, 2015;300:593-608.
Kovacs, Z. et al., Anatomical distribution of nucleoside system in the human brain and implications for therapy. In: Masino SA, Boison D, editors, Adenosine: a key link between metabolism and brain activity. Springer Science: Business Media, New York, 2013, p. 621-656.
Kovacs, Z. et al., Facilitation of spike-wave discharge activity by lipopolysaccharides in Wistar Albino Glaxo/Rijswijk rats, Neuroscience, Jun. 30, 2006;140(2):731-42.
Kovacs, Z. et al., Neonatal tricyclic antidepressant clomipramine treatment reduces the spike-wave discharge activity of the adultWAG/Rij rat. Brain Res Bull, Nov. 1, 2012;89(3-4):102-7.
Kwiterovich, P. et al., Effect of a high-fat ketogenic diet on plasma levels of lipids, lipoproteins, and apolipoproteins in children, JAMA: the journal of the American Medical Association, 2003, 290; 912-920.
Ledent, C. et al., Aggressiveness, hypoalgesia and high blood pressure in mice lacking the adenosine A2a receptor, Nature, Aug. 14, 1997;388(6643):674-8.
Leen, W.G. et al., Glucose transporter-1 deficiency syndrome: the expanding clinical and genetic spectrum of a treatable disorder, Brain, Mar. 2010;133(Pt 3):655-70.
Li, X., Using the conditioned fear stress (CFS) animal model to understand the neurobiological mechanisms and pharmacological treatment of anxiety. Shanghai Archives of Psychiatry, 2012, vol. 24, No. 5:241-249.
Luhmann, H.J. et al., Impairment of intracortical GABAergic inhibition in a rat model of absence epilepsy, Epilepsy Res, Sep. 1995;22(1):43-51.
Lutas, A. et al., The ketogenic diet: metabolic influences on brain excitability and epilepsy, Trends Neurosci, Jan. 2013;36(1):32-40.
Lynn, D.A. et al., The Ontogeny of Anxiety-Like Behavior in Rats from Adolescence to Adulthood, Developmental Psychobiology, 2010;52(8):731-739.
Masino, S.A. et al., Purines and neuronal excitability: links to the ketogenic diet, Epilepsy Res, Jul. 2012;100(3):229-38.
Mergl, R. et al., Depressive, anxiety, and somatoform disorders in primary care: prevalence and recognition, Depress Anxiety, 2007;24(3):185-95.
Mula, M. Treatment of Anxiety Disorders, in Epilepsy: An Evidence-Based Approach, Epilepsia, 2013; 54: 13-18.
Nagy, J. et al., Anti-anxiety action of diazepam after intra-amygdaloid application in the rat, Neuropharmacology, 1979; 18(6): 573-576.
Nair et al., A simple practice guide for dose conversion between animals and human, Journal of Basic and Clinical Pharmacy, Mar.-May 2016, vol. 7, Issue 2, pp. 27-31.
Paslawski, T. et al., The antidepressant drug phenelzine produces antianxiety effects in the plus-maze and increases in rat brain GABA, Psychopharmacology (Berl), Sep. 1996;127(1):19-24.
Pellow, S. et al., Validation of open:closed arm entries in an elevated plus-maze as a measure of anxiety in the rat, J Neurosci Methods, 1985;14:149-167.

(56) References Cited

OTHER PUBLICATIONS

Placidi, G.P.A. et al., Anxiety in major depression: relationship to suicide attempts, Am J Psychiatry, 2000; 157:1614-1618.

Poff, A. et al., The ketogenic diet and hyperbaric oxygen therapy prolong survival in mice with systemic metastatic cancer, PloS one Jun. 8, 2013;8(6):e65522.

Poff, A. M. et al., Ketone supplementation decreases tumor cell viability and prolongs survival of mice with metastatic cancer, International journal of cancer, 2014;1711-1720.

Rebuli, M.E. et al., Impact of Low Dose Oral Exposure to Bisphenol A (BPA) on Juvenile and Adult RatExploratory and Anxiety Behavior: A CLARITY-BPA Consortium Study, Toxicol Sci, Jul. 23, 2015;148(2):341-354.

Sankar, R. GABA(A) receptor physiology and its relationship to the mechanism of action of the 1,5-benzodiazepine clobazam, CNS Drugs, Mar. 1, 2012;26(3):229-44.

Sarkisova, K.Y. et al., Behavioral characteristics of WAG/Rij rats susceptible and non-susceptible to audiogenic seizures, Behav Brain Res, Jan. 6, 2006;166(1):9-18.

Sarkisova, K.Y. et al., Depressive-like behavioral alterations and c-fos expression in the dopaminergic brain regions in WAG/Rij rats with genetic absence epilepsy, Behav Brain Res, Sep. 15, 2003;144(1-2):211-26.

Sarkisova, K.Y. et al., The WAG/Rij strain: a genetic animal model of absence epilepsy with comorbidity of depression, Prog Neuropsychopharmacol Biol Psychiatry, Jun. 1, 2011;35(4):854-76.

Stafstrom, C. et al., The ketogenic diet as a treatment paradigm for diverse neurological disorders, Frontiers in Pharmacology, Apr. 2002; 3(59):1-8.

Teri, L. et al., Anxiety in Alzheimer's Disease: Prevalence and Comorbidity, The Journals of Gerontology Series A: Biological Sciences and Medical Sciences, 1999; 54 (7): M348-M352.

Tu, W. et al., Serotonin in the ventral hippocampus modulates anxiety-like behavior during amphetamine withdrawal, Neuroscience, Sep. 18, 2014;281C:35-43.

Veech, R. The therapeutic implications of ketone bodies: the effects of ketone bodies in pathological conditions: ketosis, ketogenic diet, redox states, insulin resistance, and mitochondrial metabolism, Prostaglandins, leukotrienes, and essential fatty acids, 2004; 70, 309-319.

Veggiotti, P. et al., Dietary Treatments and New Therapeutic Perspective in GLUT1 Deficiency Syndrome, Curr Treat Options Neurol, 2014; 16 (5):291.

Waif, A. et al., The Use of the Elevated Plus Maze as an Assay of Anxiety-Related Behavior in Rodents, Nature Protocols, 2007; 2 (2): 322-328.

Yudkoff, M. et al., The ketogenic diet and brain metabolism of amino acids: relationship to the anticonvulsant effect, Annu Rev Nutr, 2007;27:415-30.

EXOGENOUS KETONE SUPPLEMENTS FOR REDUCING ANXIETY-RELATED BEHAVIOR

CROSS-REFERENCE TO RELATED APPLICATIONS

This nonprovisional application claims priority to U.S. Provisional Patent Application No. 62/289,749, entitled "Exogenous Ketone Supplements for Reducing Anxiety-Related Behavior", filed Feb. 1, 2016 by the same inventors, the entirety of which is incorporated herein by reference.

RELATED APPLICATION

This application relates to International Patent Application No. PCT/US2014/031237, entitled "Compositions and Methods for Producing Elevated and Sustained Ketosis", filed Mar. 19, 2014 by several of the current inventors, the entirety of which is incorporated herein by reference.

FEDERALLY SPONSORED RESEARCH OR DEVELOPMENT

This invention was made with Government support under Grant Nos. N00014-09-1-0244 and N00014-13-1-0062 awarded by the Office of Naval Research. The government has certain rights in the invention.

BACKGROUND OF THE INVENTION

1. Field of the Invention

This invention relates, generally, to therapies for anxiety-related behavior. More specifically, it relates to short- and long-term ketosis to treat and/or prevent anxiety-related behavior.

2. Brief Description of the Prior Art

Anxiety

Anxiety disorders, such as generalized anxiety disorder, phobias, and panic disorder, are the most prevalent type of mental disorders (Li, Xiaobai Using the conditioned fear stress (CFS) animal model to understand the neurobiological mechanisms and pharmacological treatment of anxiety. Shanghai Archives of Psychiatry, 2012, Vol. 24, No. 5 241-249). Anxiety can be associated with psychiatric morbidity, disability, increased healthcare utilization, and mortality in the general population (Teri, L., et al. 1999. 'Anxiety in Alzheimer's Disease: Prevalence and Comorbidity'. The Journals of Gerontology Series A: Biological Sciences and Medical Sciences 54 (7): M348-M352. doi:10.1093/gerona/54.7.m348). These symptoms can cause significant distress interfering with an individual's quality of life. This commonly occurs along with other mental or physical illnesses, which may mask anxiety symptoms or even aggravate them. Some symptoms, like fear and worry, occur in all anxiety disorders including generalized anxiety disorders, panic disorder, and social anxiety disorder (Mula, Marco. 2013. 'Treatment of Anxiety Disorders, in Epilepsy: An Evidence-Based Approach'. Epilepsia 54: 13-18. doi: 10.1111/epi.12101).

Knowledge relating to the exact cause and pathomechanism(s) of anxiety disorders is far from complete; however, it is known that the amygdala is determinant in the experience of fear and anxiety by mediating the autonomic and endocrine responses through the output to the hypothalamus, and also avoidance behavior through the output to the periaqueductal gray matter (Engin E, et al. The effects of intra-cerebral drug infusions on animals' unconditioned fear reactions: a systematic review. Prog Neuropsychopharmacol Biol Psychiatry. 2008 Aug. 1; 32(6):1399-419; Li, Xiaobai Using the conditioned fear stress (CFS) animal model to understand the neurobiological mechanisms and pharmacological treatment of anxiety. Shanghai Archives of Psychiatry, 2012, Vol. 24, No. 5 241-249; Mula, Marco. 2013. 'Treatment of Anxiety Disorders, in Epilepsy: An Evidence-Based Approach'. Epilepsia 54: 13-18. doi:10.1111/epi.12101). Previous studies also show that serotonergic, glutamatergic, and GABAergic system have roles in the regulation of anxiety (Nagy J, et al. Anti-anxiety action of diazepam after intra-amygdaloid application in the rat. Neuropharmacology. 1979; 18(6): 573-576; Kakui N, et al. Anxiolytic-like profile of mirtazapine in rat conditioned fear stress model: Functional significance of 5-hydroxytryptamine 1A receptor and alpha1-adrenergic receptor. Pharmacol Biochem Behav. 2009 May; 92(3):393-8; Li, Xiaobai Using the conditioned fear stress (CFS) animal model to understand the neurobiological mechanisms and pharmacological treatment of anxiety. Shanghai Archives of Psychiatry, 2012, Vol. 24, No. 5 241-249; Dias B G, et al. Towards new approaches to disorders of fear and anxiety. Curr Opin Neurobiol. 2013 June; 23(3):346-52).

Further, anxiety and depression are common problems affecting people with epilepsy and Alzheimer's disease (AD), and can exacerbate symptoms of GLUT1 deficiency syndrome (GLUT1 DS). Comorbidity between anxiety, depression, and AD has been recognized (Teri, L., et al. 1999. 'Anxiety in Alzheimer's Disease: Prevalence and Comorbidity'. The Journals of Gerontology Series A: Biological Sciences and Medical Sciences 54 (7): M348-M352. doi:10.1093/gerona/54.7.m348; Hamid H, et al. (2011) Anxiety symptoms in epilepsy: salient issues for future research. *Epilepsy Behav* 22:63-68; Mula, Marco. 2013. 'Treatment of Anxiety Disorders, in Epilepsy: An Evidence-Based Approach'. Epilepsia 54: 13-18. doi:10.1111/epi.12101), and anxiety plays a key role in suicidality among patients with depression (Placidi G P A, et al. (2000) Anxiety in major depression: relationship to suicide attempts. *Am J Psychiatry* 157:1614-1618). Interestingly, the same brain regions involved in a significant proportion of patients with focal epilepsy, such as the amygdala and the hippocampus, also play a key role in the neurobiology of anxiety (Li, Xiaobai Using the conditioned fear stress (CFS) animal model to understand the neurobiological mechanisms and pharmacological treatment of anxiety. Shanghai Archives of Psychiatry, 2012, Vol. 24, No. 5 241-249; Dias B G, et al. Towards new approaches to disorders of fear and anxiety. Curr Opin Neurobiol. 2013 June; 23(3):346-52).

Ketones

Ketones are produced naturally in the liver only under certain physiological conditions associated with the suppression of the hormone insulin: starvation, fasting, calorie restriction, prolonged exercise, or during the consumption of high fat, low carbohydrate KD. The restrictive nature of these states has limited the clinical applicability of therapeutic ketosis due to practical considerations. In an effort to circumvent this dilemma, researchers have recently developed a number of exogenous ketogenic supplements, ketogenic precursors that are metabolized to produce a dose-dependent elevation of βHB and AcAc in the blood (Clarke, K., Tchabanenko, K., Pawlosky, R., Carter, E., Todd, K. M., Musa-Veloso, K., Ho, M., Roberts, A., Robertson, J., Vanitallie, T. B., Veech, R. L. (2012) Kinetics, safety and tolerability of (R)-3-hydroxybutyl (R)-3-hydroxybutyrate in healthy adult subjects. *Regul Toxicol Pharmacol.* 63(3):401-8; Veech, R. (2004). The therapeutic implications of ketone bodies: the effects of ketone bodies in pathological conditions: ketosis, ketogenic diet, redox states, insulin resistance, and mitochondrial metabolism. *Prostaglandins, leukotrienes, and essential fatty acids* 70, 309-319; Kesl, S. L., Poff, A. M., Ward, N. P., Fiorelli, T. N., Ari, C., Van Putten, A. J., Sherwood, J. W., Arnold, P., D'Agostino, D. P. (2016) Effects of exogenous ketone supplementation on blood ketone, glucose, triglyceride, and lipoprotein levels in Sprague-Dawley rats. Nutr Metab (Lond). 4; 13:9). Induction of hyperketonemia produces acute and chronic changes in metabolic physiology and neuropharmacological pathways that provide therapeutic effects in varied disease states.

Previous studies have demonstrated the use of exogenous ketones as a means to induce a dose-dependent hyperketonemia (1-7 mM) in rats, mice, dogs, pigs, and humans (Brunengraber, H. (1997) Potential of ketone body esters for parenteral and oral nutrition. *Nutrition.* 13(3):233-5; Ciraolo, S. T., Previs, S. F., Fernandez, C. A., Agarwal, K. C., David, F., Koshy, J., Lucas, D., Tammaro, A., Stevens, M. P., and Tserng, K. Y. (1995). Model of extreme hypoglycemia in dogs made ketotic with (R,S)-1,3-butanediol acetoacetate esters. Am J Physiol 269, 75; Clarke, K., Tchabanenko, K., Pawlosky, R., Carter, E., Todd, K. M., Musa-Veloso, K., Ho, M., Roberts, A., Robertson, J., Vanitallie, T. B., Veech, R. L. (2012) Kinetics, safety and tolerability of (R)-3-hydroxybutyl (R)-3-hydroxybutyrate in healthy adult subjects. *Regul Toxicol Pharmacol.* 63(3):401-8; Desrochers, S., David, F., Garneau, M., Jetté, M., and Brunengraber, H. (1992). Metabolism of R- and S-1,3-butanediol in perfused livers from meal-fed and starved rats. *J Biochem* 285 (Pt 2), 647-653; Puchowicz, M. A., Smith, C. L., Bomont, C., Koshy, J., David, F., Brunengraber, H. (2000) Dog model of therapeutic ketosis induced by oral administration of R,S-1,3-butanediol diacetoacetate. *J Nutr Biochem.* 11(5):281-7. PubMed PMID: 10876102; Srivastava, S., Kashiwaya, Y., King, M., Baxa, U., Tam, J., Niu, G., Chen, X., Clarke, K., and Veech, R. (2012). Mitochondrial biogenesis and increased uncoupling protein 1 in brown adipose tissue of mice fed a ketone ester diet. FASEB Journal: Official publication of the Federation of American Societies for Experimental Biology 26, 2351-2362; Desrochers, S., Quinze, K., Dugas, H., Dubreuil, P., Bomont, C., David, F. et al. (1995). *R,S*-1,3-*butanediol acetoacetate esters, potential alternates to lipid emulsions for total parenteral nutrition. Journal Nutr Biochem*, 6(2), 111-118). Exogenous ketogenic supplementation mimics the metabolic and physiologic effects of the KD, including enhancing mitochondrial biogenesis, anaplerosis, suppression of glycolysis, and increasing ATP and adenosine production, all thought to mediate the therapeutic effects of KD in epilepsy (Kesl, S., Prather, J., Sherwood, J., Gould, L., D'Agostino, P. D. (2014). Sustaining dietary ketosis to improve blood flow and wound healing in young and aged Fisher rats. *The FASEB Journal* 28 no. 1 Supplement 734.7, 73; Poff, A. M., Ward, N., Seyfried, T. N., Arnold, P., D'Agostino, D. P. (2015). Non-Toxic Metabolic Management of Metastatic Cancer in VM Mice: Novel Combination of Ketogenic Diet, Ketone Supplementation, and Hyperbaric Oxygen Therapy. *PLoS One* 10: e0127407, 125; Srivastava, S., Kashiwaya, Y., King, M., Baxa, U., Tam, J., Niu, G., Chen, X., Clarke, K., and Veech, R. (2004). The therapeutic implications of ketone bodies: the effects of ketone bodies in pathological conditions: ketosis, ketogenic diet, redox states, insulin resistance, and mitochondrial metabolism. *Prostaglandins, leukotrienes, and essential fatty acids* 70, 309-319). Mitochondrial biogenesis and increased uncoupling protein 1 in brown adipose tissue of mice fed a ketone ester diet. FASEB Journal: Official publication of the Federation of American Societies for Experimental Biology 26, 2351-2362; Veech, 2004).

Anecdotal reports suggest that nutritional ketosis can promote a reduction in anxiety, although there is currently no convincing evidence to indicate that elevated ketone levels would reduce anxiety in humans (Ehrenreich M J. A case of the re-emergence of panic and anxiety symptoms after initiation of a high-protein, very low carbohydrate diet. Psychosomatics. 2006 March-April; 47(2):178-9 Engin E, et al. The effects of intra-cerebral drug infusions on animals' unconditioned fear reactions: a systematic review. Prog Neuropsychopharmacol Biol Psychiatry. 2008 Aug. 1; 32(6):1399-419). Nutritional ketosis is a state when the body utilizes ketones instead of glucose as the primary molecule of energy metabolism (Veech, R. (2004) The therapeutic implications of ketone bodies: the effects of ketone bodies in pathological conditions: ketosis, ketogenic diet, redox states, insulin resistance, and mitochondrial metabolism. *Prostaglandins, leukotrienes, and essential fatty acids* 70, 309-319). Specifically, the body increases conversion of ketones such as beta-hydroxybutyrate (βHB) into acetyl-CoA and thus generates ATP (Yudkoff M, et al. The ketogenic diet and brain metabolism of amino acids: relationship to the anticonvulsant effect. Annu Rev Nutr. 2007; 27:415-30). This can be achieved by fasting or following a ketogenic diet (KD), which is a high-fat (70-85% of daily caloric intake) and low-carbohydrate (5-10%) diet (Kwiterovich, P., et al. (2003) Effect of a high-fat ketogenic diet on plasma levels of lipids, lipoproteins, and apolipoproteins in children. *JAMA: the journal of the American Medical Association* 290, 912-920; De Giorgis, Valentina, et al. 2013. 'GLUT1 Deficiency Syndrome 2013: Current State of The Art'. 22 (10): 803-811. doi:10.1016/j.seizure.2013.07.003).

Maintaining long-term ketosis has proven to be beneficial in epileptic patients by decreasing the frequency and severity of seizures (Kossoff E H, et al. Ketogenic diets: treatments for epilepsy and other disorders. 5th ed. New York N.Y.: Demos Medical; 2011). Nutritional ketosis also has confirmed beneficial effects in patients with AD, GLUT1 DS, and cancer (Vegiotti and De Giorgis, 2014; Poff, A., et al. (2013) The ketogenic diet and hyperbaric oxygen therapy prolong survival in mice with systemic metastatic cancer. *PloS one* 8; Poff, A. M., et al. (2014) Ketone supplementation decreases tumor cell viability and prolongs survival of mice with metastatic cancer. *International journal of cancer*). GLUT1 DS results from impaired glucose transport into the brain (Klepper J, et al. Facilitated glucose transporter protein type 1 (GLUT1) deficiency syndrome: impaired glucose transport into brain—a review. Eur J Pediatr. 2002 June; 161(6):295-304. Epub 2002 Apr. 16. Review. PubMed PMID:12029447); however, ketones use another transporter to enter the central nervous system (CNS), providing an alternative source of fuel. Therefore, nutritional ketosis is used as a treatment option in GLUT1 patients (De Giorgis, Valentina, et al. 2013. 'GLUT1 Deficiency Syndrome 2013: Current State of The Art'. 22 (10): 803-811. doi:10.1016/j.seizure.2013.07.003), effectively correcting the impaired brain energy metabolism and reducing the frequency of the seizures (Leen W G, et al. Glucose transporter-1 deficiency syndrome: the expanding clinical and genetic spectrum of a treatable disorder. Brain. 2010 March; 133(Pt 3):655-70. doi:10.1093/brain/awp336. Epub 2010 Feb. 2. PubMed PMID: 20129935).

Additionally, previous studies have shown an anxiolytic effect in the EPM when the antidepressant/antipanic drug phenelzine, agonists and/or antagonists of different neurotransmitter systems (e.g., GABAergic and glutamatergic system) were given acutely to rats (Paslawski T, et al. The antidepressant drug phenelzine produces antianxiety effects in the plus-maze and increases in rat brain GABA. Psychopharmacology (Berl). 1996 September; 127(1):19-24. PubMed PMID: 8880939; Engin E, et al. The effects of intra-cerebral drug infusions on animals' unconditioned fear reactions: a systematic review. Prog Neuropsychopharmacol Biol Psychiatry. 2008 Aug. 1; 32(6):1399-419). Additionally, the anxiolytic properties of cannabidiol were tested in an EPM in rats, and it significantly increased the entry ratio (open/total number of entries), suggesting an anxiolytic-like effect (Guimarães F S, et al. Anxiolytic effect in the elevated plus-maze of the N/MDA receptor antagonist AP7 microinjected into the dorsal periaqueductal grey. Psychopharmacology (Berl). 1991; 103(1):91-4; Gomes F V, et al. The anxiolytic-like effects of cannabidiol injected into the bed nucleus of the stria terminalis are mediated by 5-HT1A receptors. Psychopharmacology (Berl). 2011 February; 213 (2-3):465-73. doi: 10.1007/s00213-010-2036-z. Epub 2010 Oct. 14. PubMed PMID: 20945065).

It has been demonstrated that KD may (i) decrease extracellular glutamate release/level by means of inhibition of vesicular glutamate transporter, (ii) increase adenosine level, and (iii) augment the GABAergic effects by $GABA_A$ receptors (Yudkoff M, et al. The ketogenic diet and brain metabolism of amino acids: relationship to the anticonvulsant effect. Annu Rev Nutr. 2007; 27:415-30; Engin E, et al. The effects of intra-cerebral drug infusions on animals' unconditioned fear reactions: a systematic review. Prog Neuropsychopharmacol Biol Psychiatry. 2008 Aug. 1; 32(6):1399-419; Masino S A, et al. Purines and neuronal excitability: links to the ketogenic diet. Epilepsy Res. 2012 July; 100(3):229-38; Lutas A, et al. The ketogenic diet: metabolic influences on brain excitability and epilepsy. Trends Neurosci. 2013 January; 36(1):32-40). It has been demonstrated that serotonergic, glutamatergic and GABAergic system of different brain areas such as hippocampus and/or amygdala have a role in the regulation of anxiety: serotonin (5-hydroxytryptamine, 5-HT) transporters, serotonin receptors (e.g., 5-HT1A), N-methyl-D-aspartate (NMDA) receptors and GABA receptors (e.g., $GABA_A$ receptors) are potential targets in the treatment of anxiety disorders (Nagy J, et al. Anti-anxiety action of diazepam after intra-amygdaloid application in the rat. Neuropharmacology. 1979; 18(6): 573-576; Kakui N, et al. Anxiolytic-like profile of mirtazapine in rat conditioned fear stress model: Functional significance of 5-hydroxytryptamine 1A receptor and alpha1-adrenergic receptor. Pharmacol Biochem Behav. 2009 May; 92(3):393-8; Li, Xiaobai Using the conditioned fear stress (CFS) animal model to understand the neurobiological mechanisms and pharmacological treatment of anxiety. Shanghai Archives of Psychiatry, 2012, Vol. 24, No. 5 241-249; Sankar R. GABA(A) receptor physiology and its relationship to the mechanism of action of the 1,5-benzodiazepine clobazam. CNS Drugs. 2012 Mar. 1; 26(3):229-44; Dias B G, et al. Towards new approaches to disorders of fear and anxiety. Curr Opin Neurobiol. 2013 June; 23(3):346-52). It was concluded that GABAergic system may have critical role in the modulation of the level of anxiety: increased GABAergic transmission may evoke anxiolytic effect (Engin E, et al. The effects of intra-cerebral drug infusions on animals' unconditioned fear reactions: a systematic review. Prog Neuropsychopharmacol Biol Psychiatry. 2008 Aug. 1; 32(6):1399-419; Li, Xiaobai Using the conditioned fear stress (CFS) animal model to understand the neurobiological mechanisms and pharmacological treatment of anxiety. Shanghai Archives of Psychiatry, 2012, Vol. 24, No. 5 241-249). Thus, augmentation of the GABAergic effects by means of KD via $GABA_A$ receptors may evoke a decrease in anxiety level.

It has also been demonstrated that (i) KD may increase extracellular adenosine level (Masino S A, et al. Purines and neuronal excitability: links to the ketogenic diet. Epilepsy Res. 2012 July; 100(3):229-38; Lutas A, et al. The ketogenic diet: metabolic influences on brain excitability and epilepsy. Trends Neurosci. 2013 January; 36(1):32-40), (ii) inhibition of adenosine receptors ($A_1R$ and $A_{2A}R$) by means of caffeine promotes anxious behavior (Klein E, et al. Anxiogenic effects of m-CPP in patients with panic disorder: comparison to caffeine's anxiogenic effects. *Biol Psychiatry*. 1991 Nov. 15; 30(10):973-84), (iii) $A_1R$- or $A_{2A}R$-knockout mice showed anxiogenic-like behaviors (Johansson B, et al. Hyperalgesia, anxiety, and decreased hypoxic neuroprotection in mice lacking the adenosine A1 receptor. Proc Natl Acad Sci USA. 2001 Jul. 31; 98(16):9407-12. Epub 2001 Jul. 24; Ledent C, et al. Aggressiveness, hypoalgesia and high blood pressure in mice lacking the adenosine A2a receptor. Nature. 1997 Aug. 14; 388(6643):674-8) and (iv) modulation of adenosine receptor activity might be an effective treatment strategy for patients with anxiety disorders (Kovacs, Z., Dobolyi, A. (2013). Anatomical distribution of nucleoside system in the human brain and implications for therapy. In: Masino S A, Boison D, editors. Adenosine: a key link between metabolism and brain activity. Springer Science: Business Media, New York. p. 621-656) Anatomical distribution of nucleoside system in the human brain and implications for therapy. In: Masino S A, Boison D, editors. Adenosine: a key link between metabolism and brain activity. Springer Science: Business Media, New York. p. 621-656). In addition, as KD may evoke decreased extracellular glutamate level (Lutas A, et al. The ketogenic diet: metabolic influences on brain excitability and epilepsy. Trends Neurosci. 2013 January; 36(1):32-40) and NMDA receptor antagonists may have anxiolytic effects (Guimarães, F. S., Carobrez, A. P., De Aguiar, J. C., Graeff, F. G. (1991). Anxiolytic effect in the elevated plus-maze of the NMDA receptor antagonist AP7 microinjected into the dorsal periaqueductal grey. *Psychopharmacology* (Berl).103 (1):91-4; Engin E, et al. The effects of intra-cerebral drug infusions on animals' unconditioned fear reactions: a systematic review. Prog Neuropsychopharmacol Biol Psychiatry. 2008 Aug. 1; 32(6):1399-419) KD may exert its alleviating effect on anxiety level via glutamatergic system. Indeed, a recent study supports the effect of ketone esters increasing the brain GABA/Glutamate ratio in an animal model of Angelman's syndrome (Ciarlone, S. L., Grieco, J. C., D'Agostino, D. P., Weeber, E. J. (2016) Ketone ester supplementation attenuates seizure activity, and improves behavior and hippocampal synaptic plasticity in an Angelman mouse model. *Neurobiol Dis.* 18; 96:38-46).

However, many patients with epilepsy, AD, and about 20% of GLUT1 DS patients have difficulties with compliance, or experience a loss of effectiveness over time (Veggiotti, et al. 2014. 'Dietary Treatments and New Therapeutic Perspective in GLUT1 Deficiency Syndrome'. Curr Treat Options Neurol 16 (5). doi:10.1007/s11940-014-0291-8). Further, very little is known about the link between ketone application-evoked changes in CNS and anxiety disorders.

Attempts have been made and studies have been performed to overcome the foregoing problems, though none have been completely effective. Examples include U.S. Patent Application Publication Serial No. 2015/0132280; U.S. Patent Application Publication Serial No. 2015/0344413; Yoshihiro Kashiwaya et al., "A ketone ester diet exhibits anxiolytic and cognition-sparing properties, and lessens amyloid and tau pathologies in a mouse model of Alzheimer's disease", Neurobiology of Aging 34 (2013) 1530-1539; and Carl E. Strafstrom et al., "The ketogenic diet as a treatment paradigm for diverse neurological disorders", Frontiers in Pharmacology: Neuropharmacology 3(59): 1-8 (April 2012). However, it is still unknown how to maintain the desired long-term ketosis, both for reducing anxiety-related behavior and for sustaining nutritional ketosis.

Accordingly, what are needed are short-term and long-term therapeutic strategies that have increased effectiveness in maintaining ketosis to improve anxiety-related behavior. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an improved treatment for anxiety disorders and anxiety-related behaviors is now met by a new, useful, and nonobvious invention.

In an embodiment, the current invention is a method of treating a patient suffering from an anxiety disorder or a method of reducing anxiety in a patient/subject. The method comprises administering to the patient a therapeutically effective amount of exogenous ketone supplementation chronically or sub-chronically. The ketone supplementation can be a ketone ester (e.g., 1,3-butanediol-acetoacetate diester), a ketone salt (e.g., beta-hydroxybutyrate-mineral salt (chronic administration)), or combined with MCT (medium chain triglyceride), a combination thereof. Butanediol was used in aged rats.

When the ketone ester is used, it can be low concentration (~10 g/kg b.w./day) or high concentration (~25 g/kg b.w./day). Alternatively, when the ketone salt is used, it can have a concentration of ~25 g/kg b.w./day. Optionally, the ketone salt can be admixed with a medium chain triglyceride in a 1:1 ratio, potentially each having a concentration of ~25 g/kg b.w./day. Alternatively, sub-chronic administration can accomplish benefits at 5 g/kg/day or 2.5 g/kg/day.

In another embodiment, the current invention is a method of reducing anxiety in a patient/subject, comprising chronically administering to the patient or subject a therapeutically effective amount of exogenous ketone supplementation. The ketone supplementation includes a ketone salt comprising beta-hydroxybutyrate-mineral salt admixed with a medium chain triglyceride in a 1:1 ratio, such that the concentration of the beta-hydroxybutyrate-mineral salt and the medium chain triglyceride is each ~25 g/kg b.w./day.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIG. 1A is a graphical illustration showing that rats consuming SD+KS or SD+KSMCT supplements spent more time in open arms and less in closed arms, showing reduced anxiety compared to control (SD) group.

FIG. 1B is a graphical illustration showing that rats consuming ketone supplements travelled more distance in open arms (SD+KS and SD-KSMCT) and less in closed arms (SD+LKE, SD+KS and SD-KSMCT), showing reduced anxiety compared to control group.

FIG. 1C is a graphical illustration showing that rats consuming SD+HKE, SD+KS or SD+KSMCT entered the closed arms later, showing reduced anxiety compared to control group.

FIG. 1D is a graphical illustration showing that rats consuming either ketone supplements with ~25 g/kg b.w./day dose (SD+HKE/KS/KSMCT) had elevated blood ketone levels after 13 weeks compared to control group.

FIG. 1E is a graphical illustration showing that blood glucose levels were be elevated in SD+KSMCT groups after 13 weeks.

SD+KSMCT: SD+βHB-S+medium chain triglyceride (MCT) (~5 g/kg b.w./day); (*p<0.05; p<0.01; *p<0.001; ****p<0.0001).

Figure 2A:
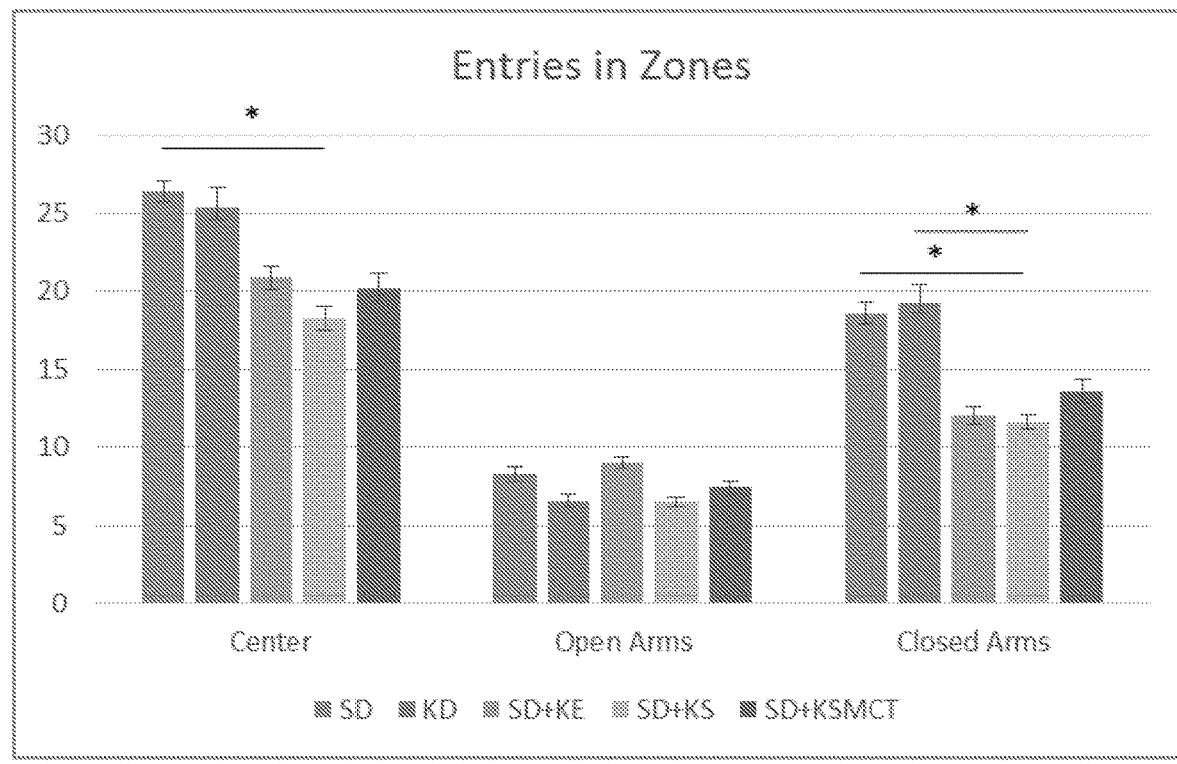
FIGS. 2A-2E depict response of SPD rats to 7 days oral administration (gavage) of exogenous ketone supplementation. Abbreviations: SD: standard rodent chow+water (~25 g/kg b.w. water/day); KD: ketogenic diet (25 g/kg b.w./day); SD+KE: SD+ketone ester (1,3-butanediol-acetoacetate diester, ~5 g/kg b.w./day); SD+KS: SD+beta-hydroxybutyrate-mineral salt (βHB-S) (~5 g/kg b.w./day)

FIG. 2A is a graphical illustration showing that less entries were in center and in closed arms by SD+KS group.

Figure 2B:
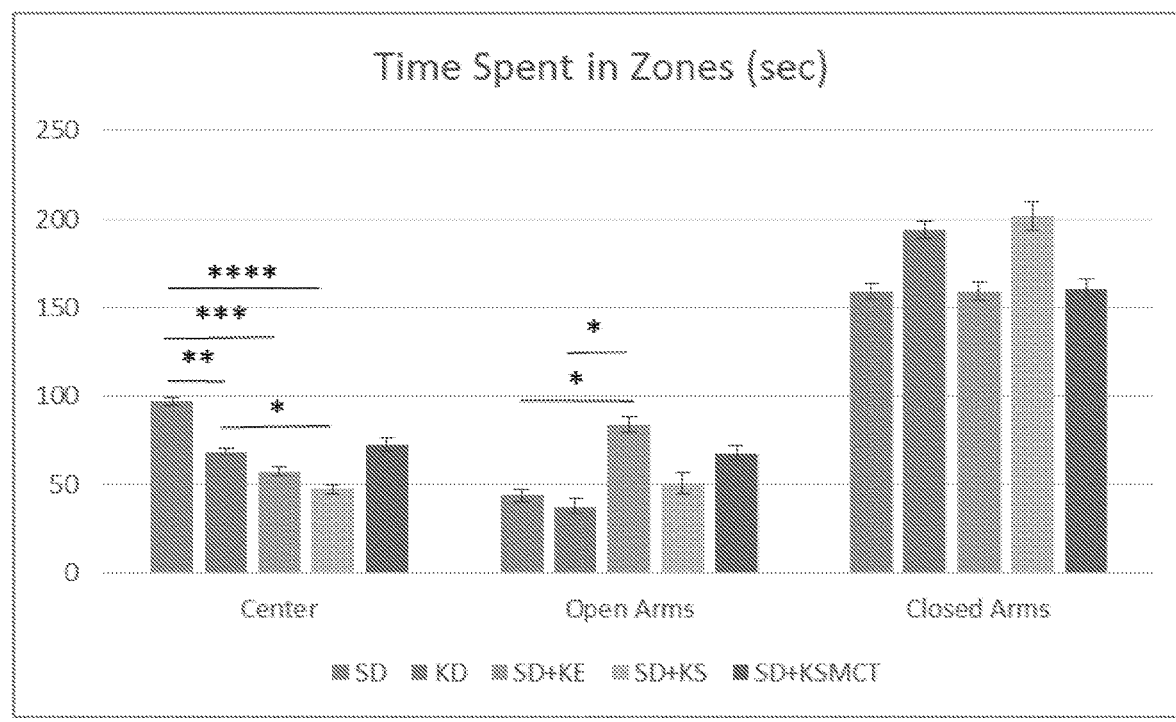

FIG. 2B is a graphical illustration showing that more time was spent in open arms by SD+KE group and less time spent in center by KD, SD+KE, SD+KS groups, compared to control.

Figure 2C:
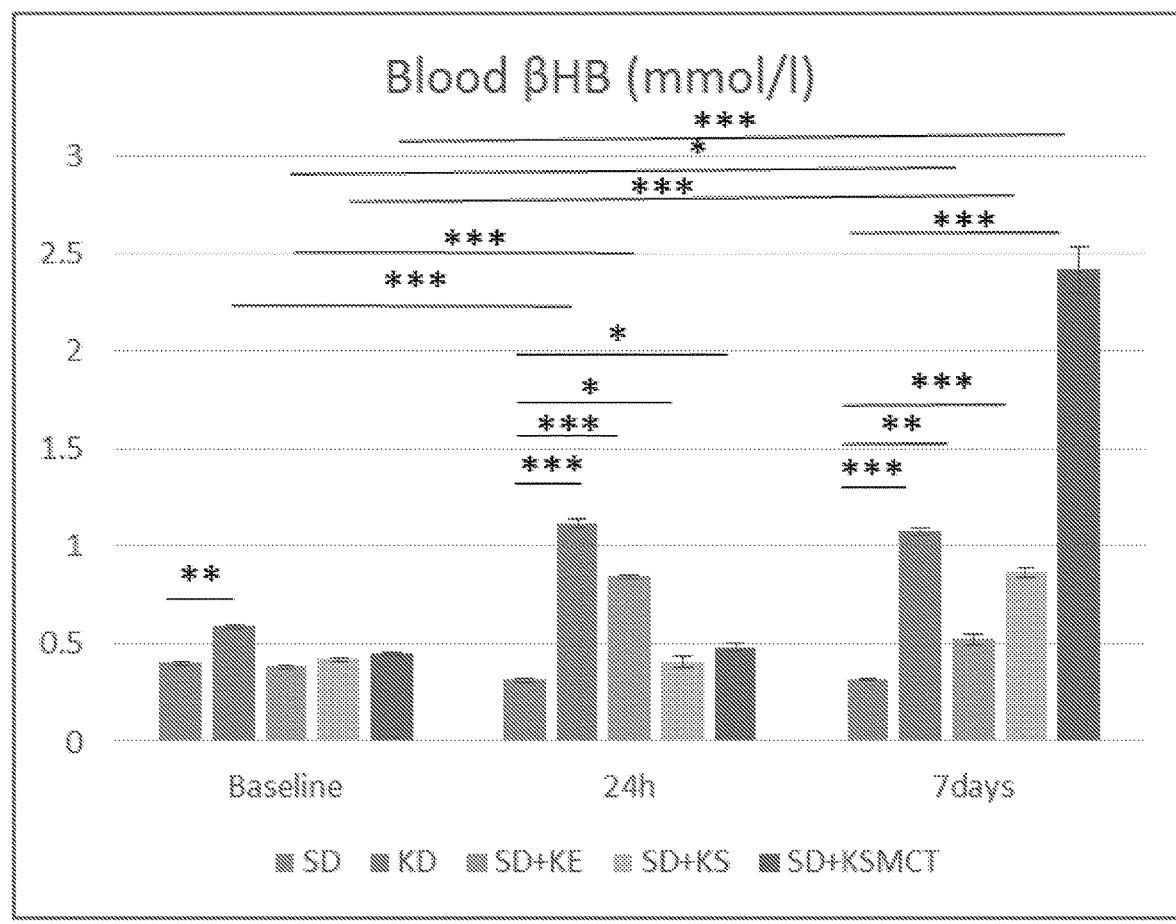

FIG. 2C is a graphical illustration showing that blood βHB levels were higher in all treatment groups after 24 hours and after 7 days as well. Specifically, blood βHB level was higher in KD group at baseline whereas compared to control, and blood βHB levels were higher in KD and SD+KE groups.

Figure 2D:
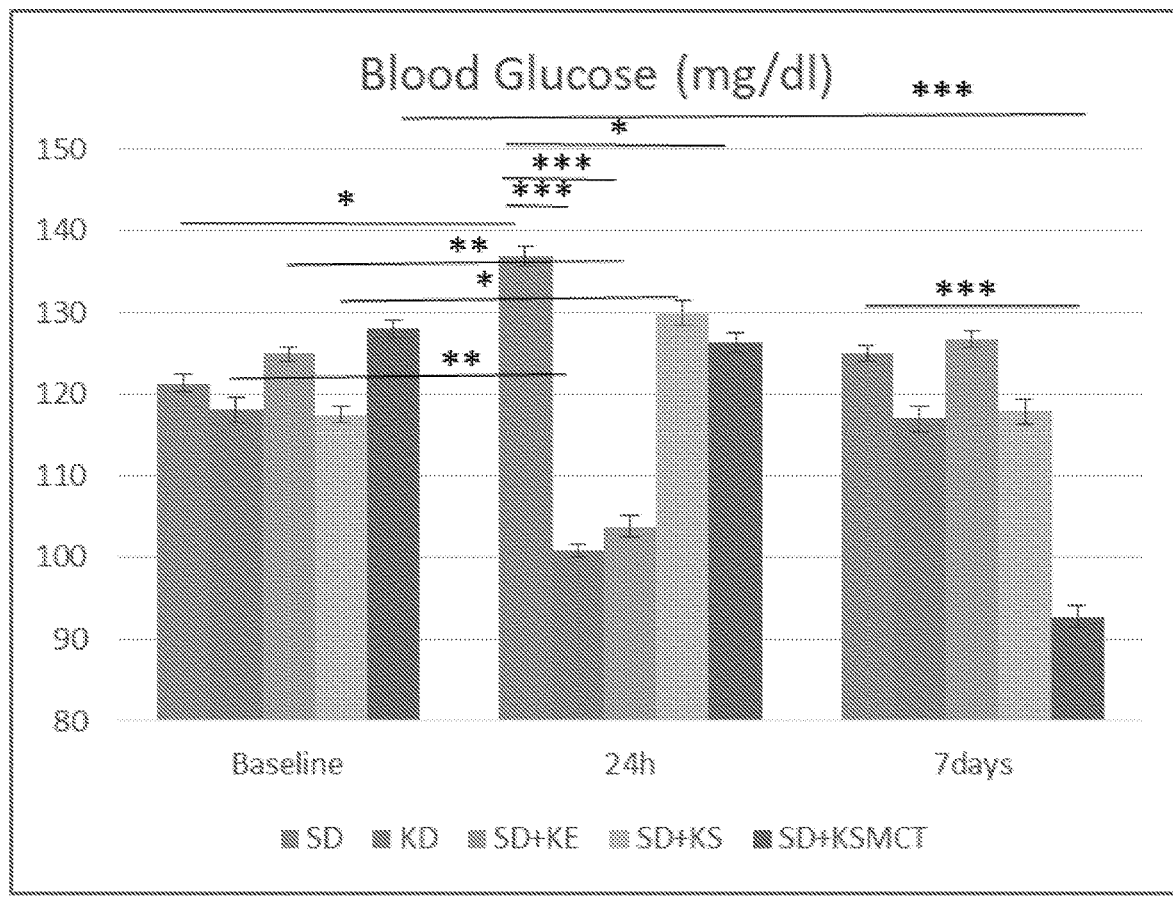

FIG. 2D is a graphical illustration showing that blood glucose was lower in all treatment groups, except SD+KSMCT, after 24 hours. Blood glucose was lower in SD+KSMCT group after 7 days, compared to its baseline. Blood glucose was lower in KD, SD+KE, SD+KSMCT groups after 24 hours, compared to control. Blood glucose was lower in SD+KSMCT group after 7 days, compared to control.

Figure 2E:
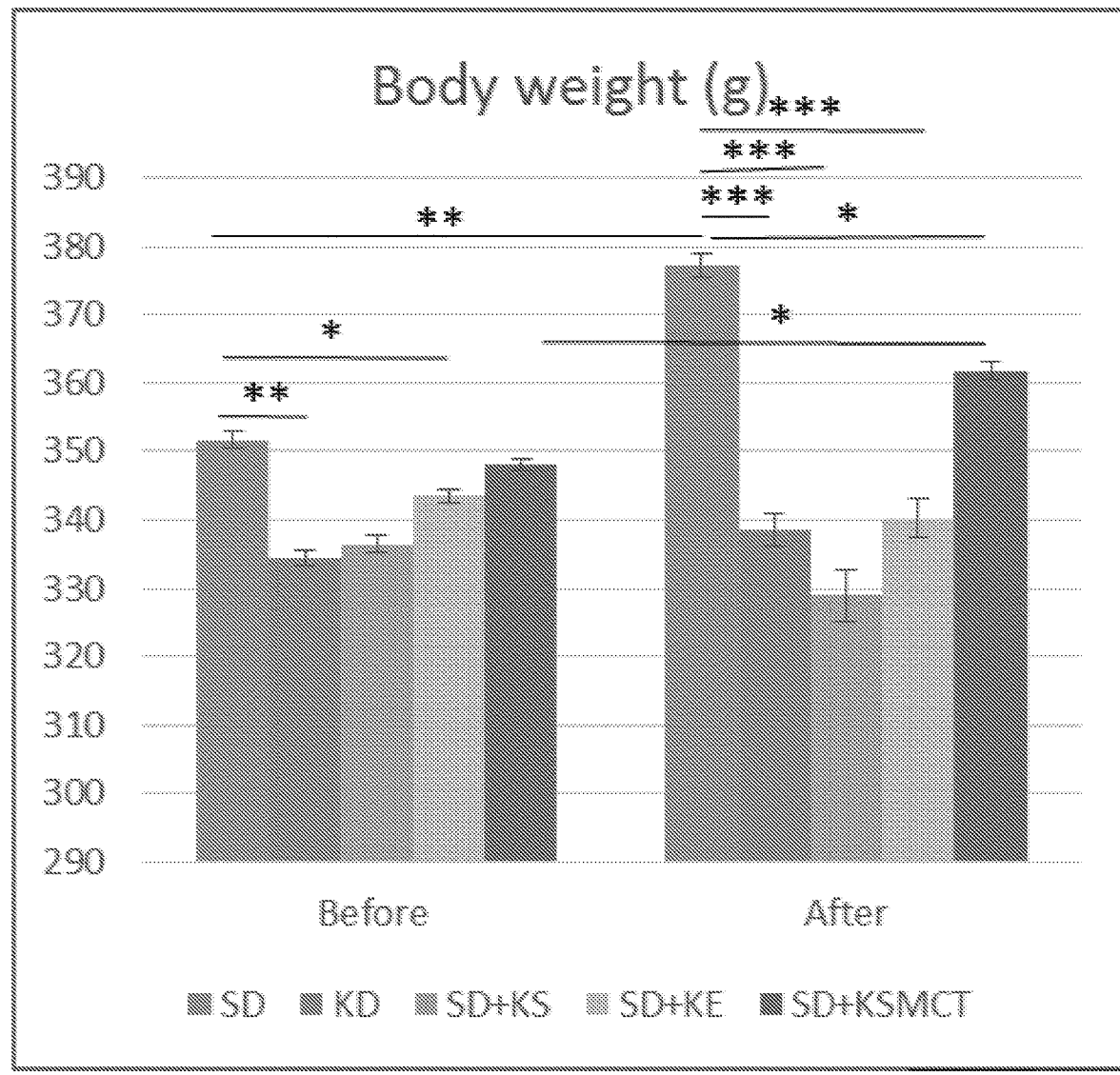

FIG. 2E is a graphical illustration showing that body weight increased in SD and SD+KSMCT groups, compared to their baseline. Body weight was lower in KD and SD+KS groups at baseline, compared to control. Body weight was lower in all treatment groups after 7 days, compared to control.

FIGS. 3A-3E depict response of WAG/Rij rats to 7 days oral administration of exogenous ketone supplementation. Abbreviations: SD: standard rodent chow+water (~2.5 g/kg b.w. water/day); SD+KE: SD+ketone ester (1,3-butanediol-acetoacetate diester, ~2.5 g/kg b.w./day); SD+KS: SD+beta-hydroxybutyrate-mineral salt (βHB-S; ~2.5 g/kg b.w./day); (*p<0.05; p<0.01; *p<0.001; ****p<0.0001).

Figure 3A:
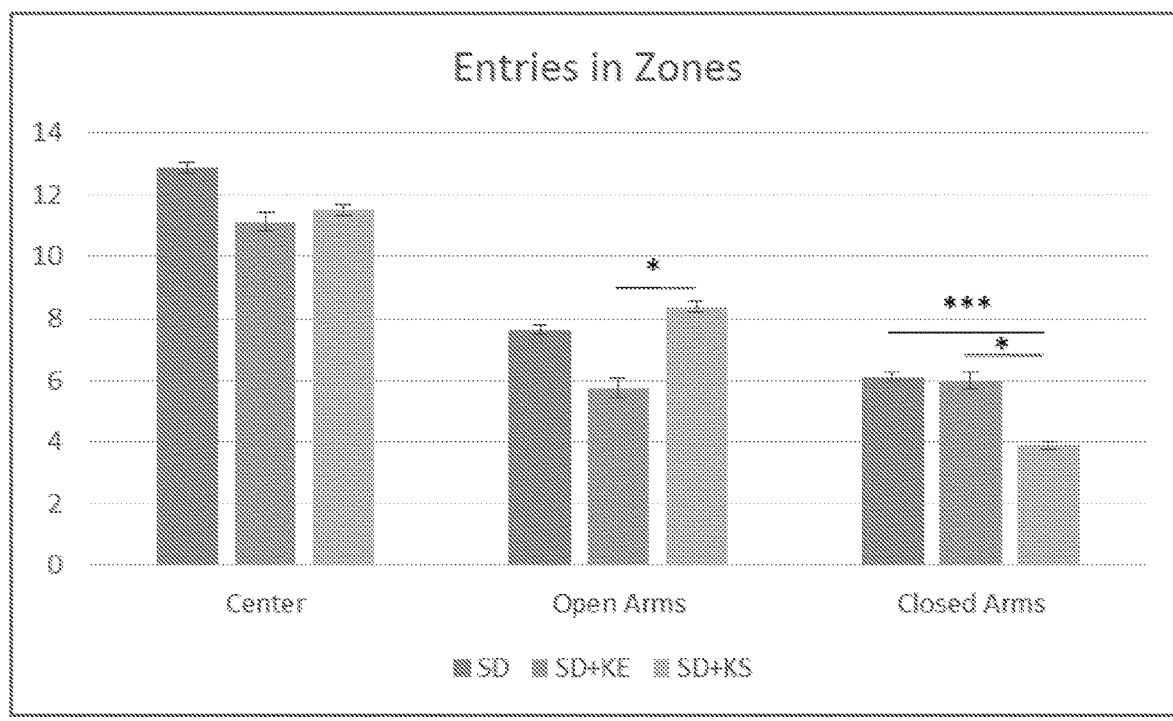

FIG. 3A is a graphical illustration showing that less entries were in closed arms by SD+KS group, compared to control.

Figure 3B:
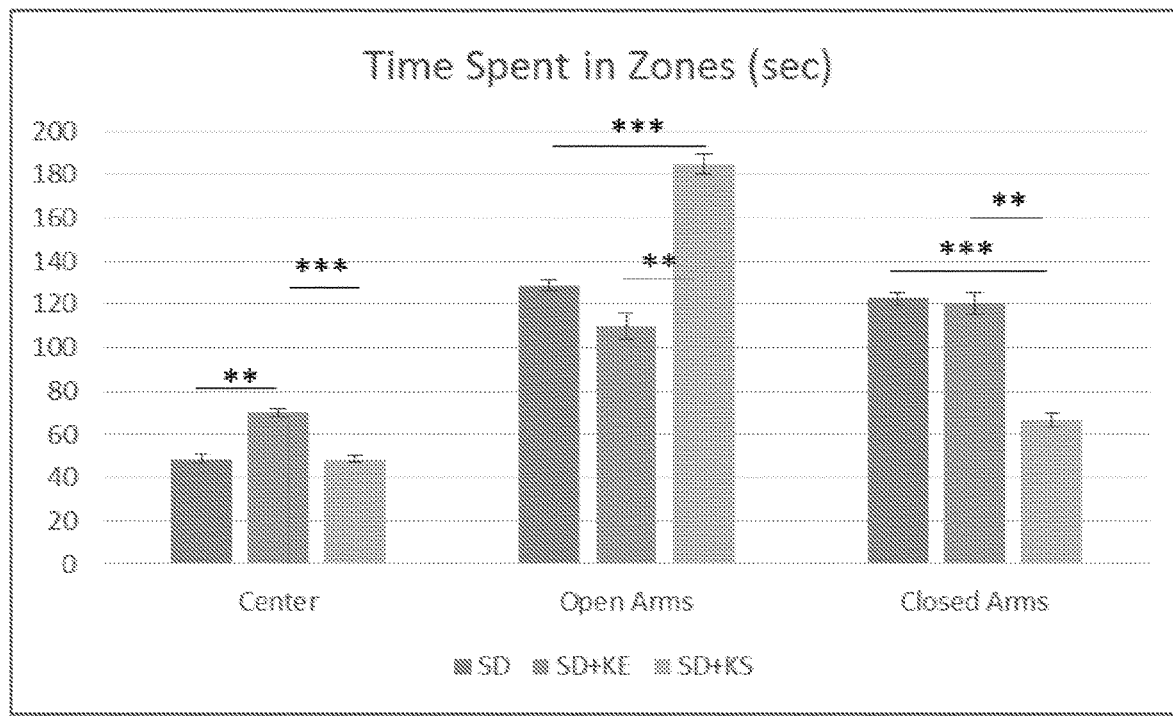

FIG. 3B is a graphical illustration showing that more time was spent in open arms and less time spent in closed arms by SD+KS group, compared to control.

Figure 3C:
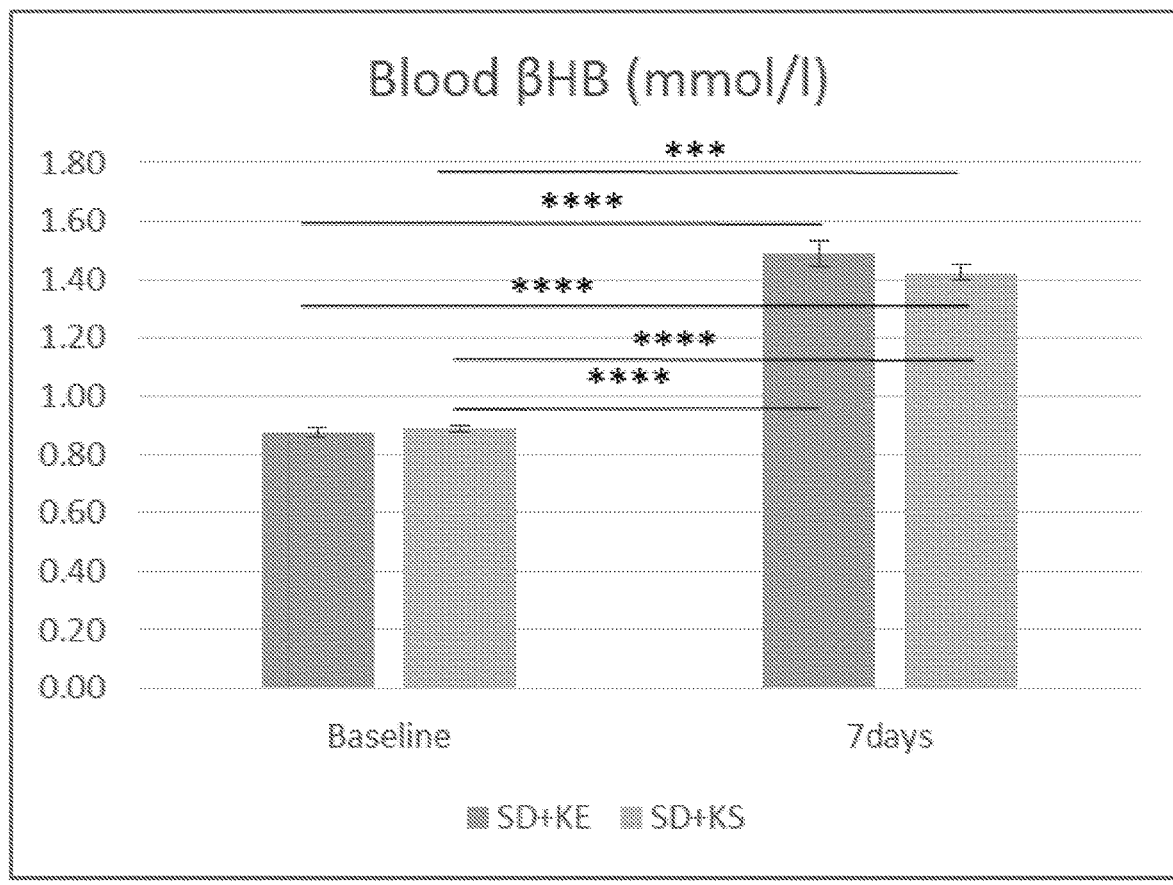

FIG. 3C is a graphical illustration showing that blood βHB levels were higher in both treatment groups (SD+KE/KS) after 7 days, compared to baseline.

Figure 3D:

FIG. 3D is a graphical illustration showing that blood glucose level did not change significantly in either group, compared to baseline levels.

Figure 3E:

FIG. 3E is a graphical illustration showing that body weight did not change significantly in either group during the treatment period.

Figure 4A:
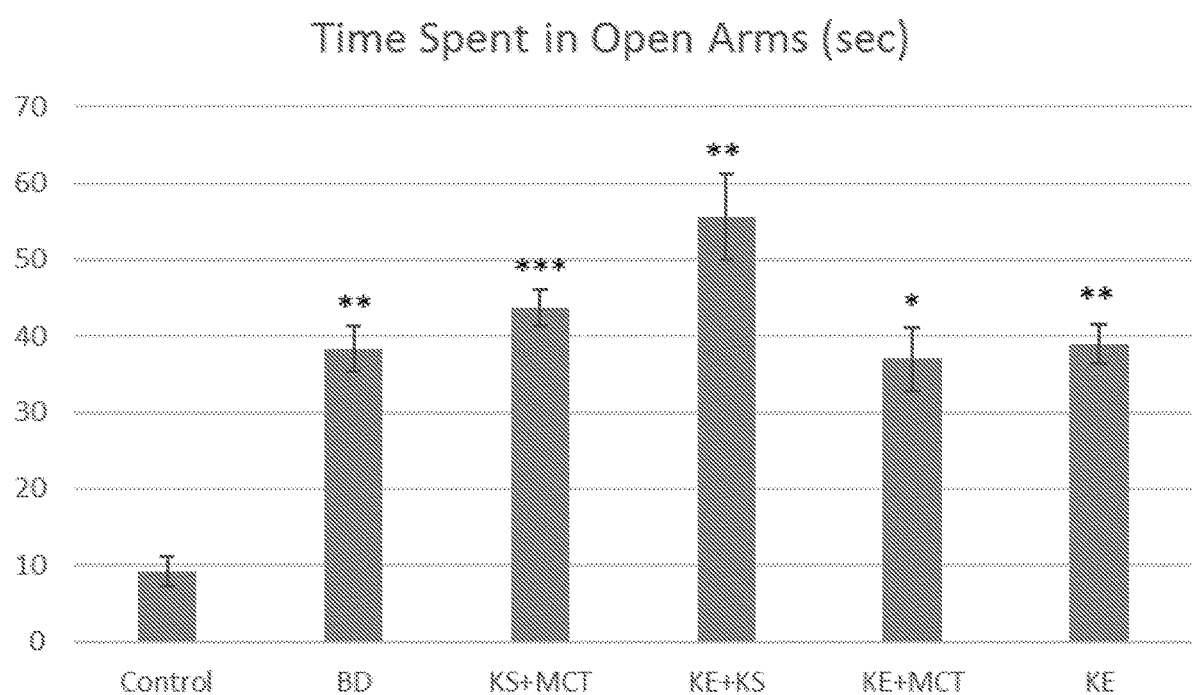

FIG. 4A is a graphical illustration depicting that 30 min after single dose administration of ketone supplements, the 1 year old SPD rats spent more time in the open arms, compared to the control group.

Figure 4B:
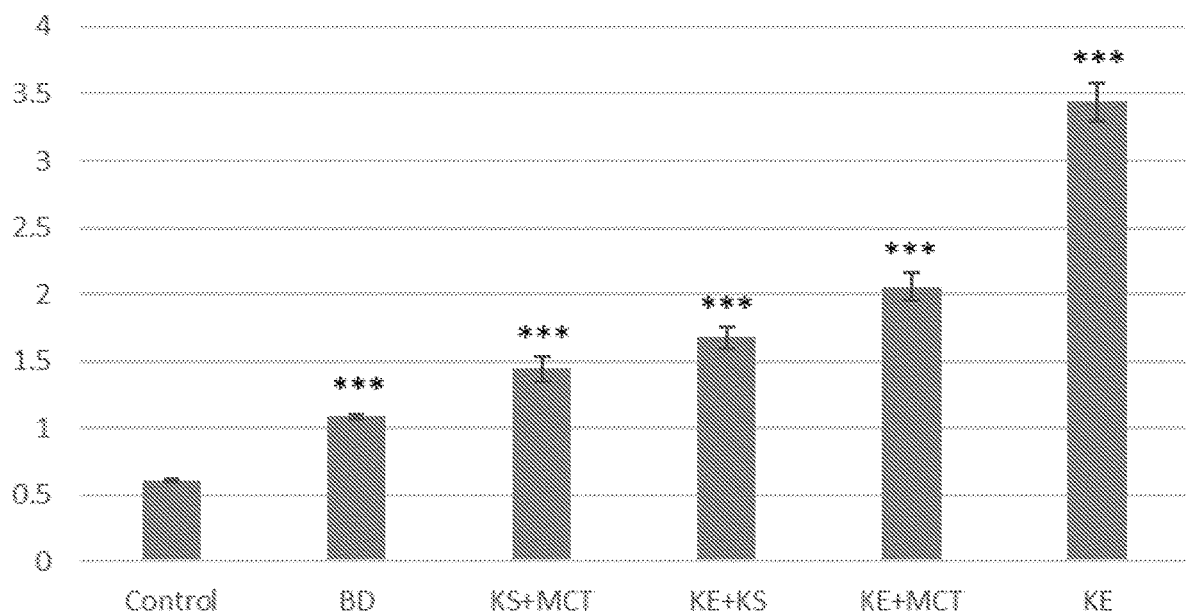
Figure 4C:
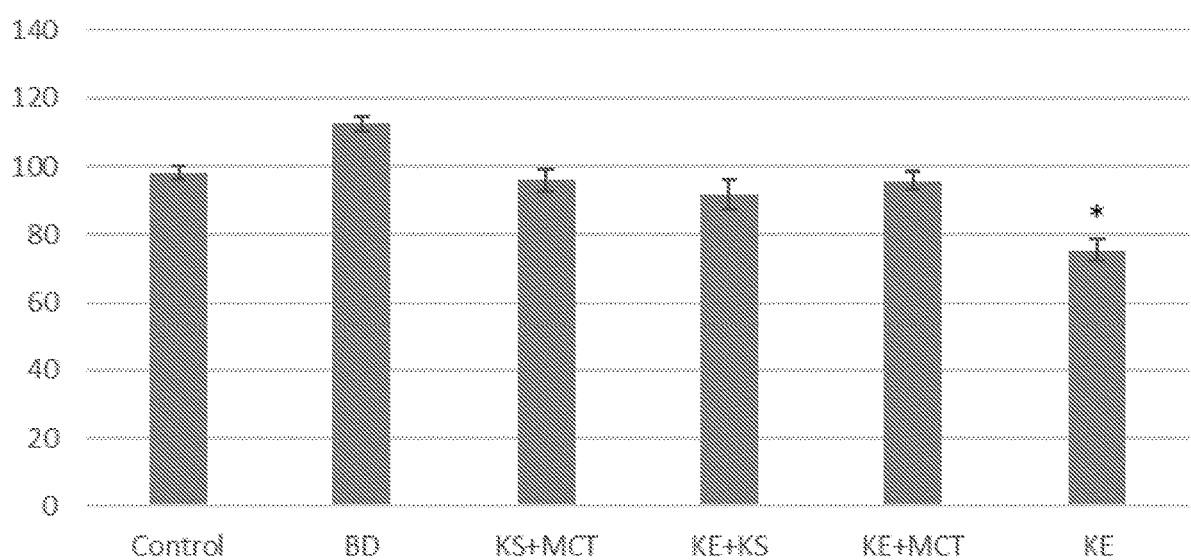

FIG. 4B is a graphical illustration depicting that ~40 min after single dose administration of ketone supplements and right after completion of 5 min EPM test in 1 year old SPD rats, all treatment group had significantly elevated βHB levels, compared to control group FIG. 4C is a graphical illustration depicting that ~40 min after single dose administration of ketone supplements and right after completion of 5 min EPM test in 1 year old SPD rats, KE group had significantly lower blood glucose level, compared to control group.

FIGS. 5A-5E depicts response of SPD rats to chronic feeding of exogenous ketone supplementation. Abbreviations: SD: standard rodent chow+water (~25 g/kg b.w. water/day); LKE: SD+low-dose ketone ester (1,3-butanediol-acetoacetate diester, ~10 g/kg b.w./day); HKE: SD+high dose ketone ester (~25 g/kg b.w./day); KS: SD+beta-hydroxybutyrate-mineral salt (βHB-S) (~25 g/kg b.w./day); KSMCT: SD+βHB-S+medium chain triglyceride (MCT) (~25 g/kg b.w./day); (*p<0.05; p<0.01; *p<0.001; ****p<0.0001)

Figure 5A:
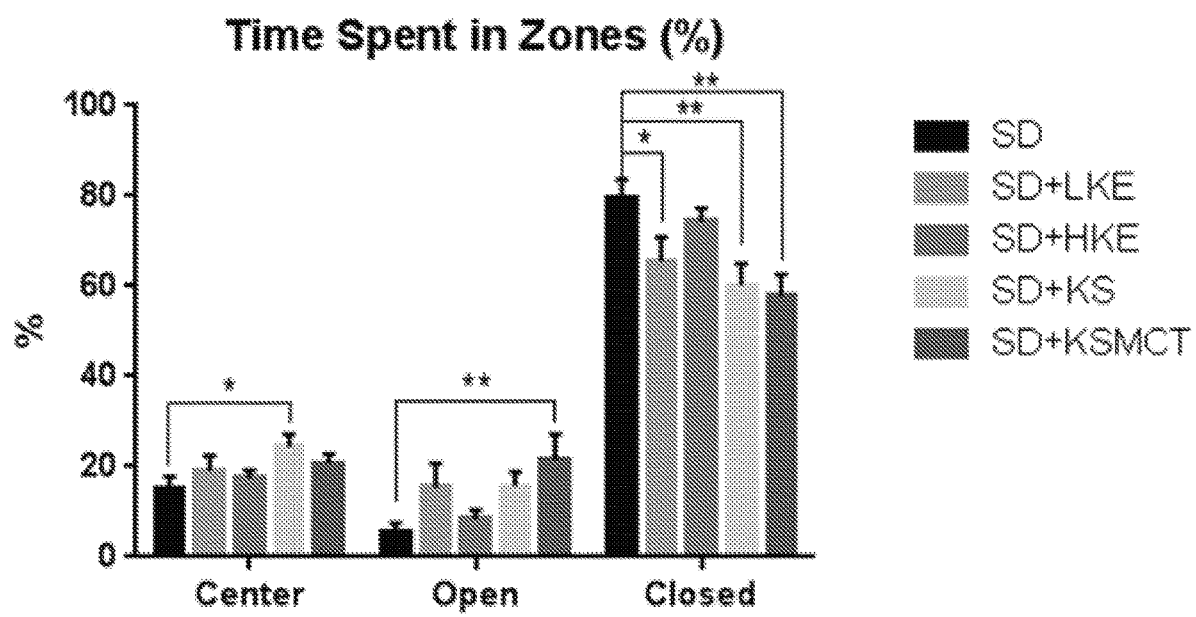

FIG. 5A shows that rats consuming KSMCT supplements spent more time in open arms (open), LKE, KS and KSMCT groups spent less time in closed arms (closed), showing reduced anxiety compared to control (SD) group.

Figure 5B:
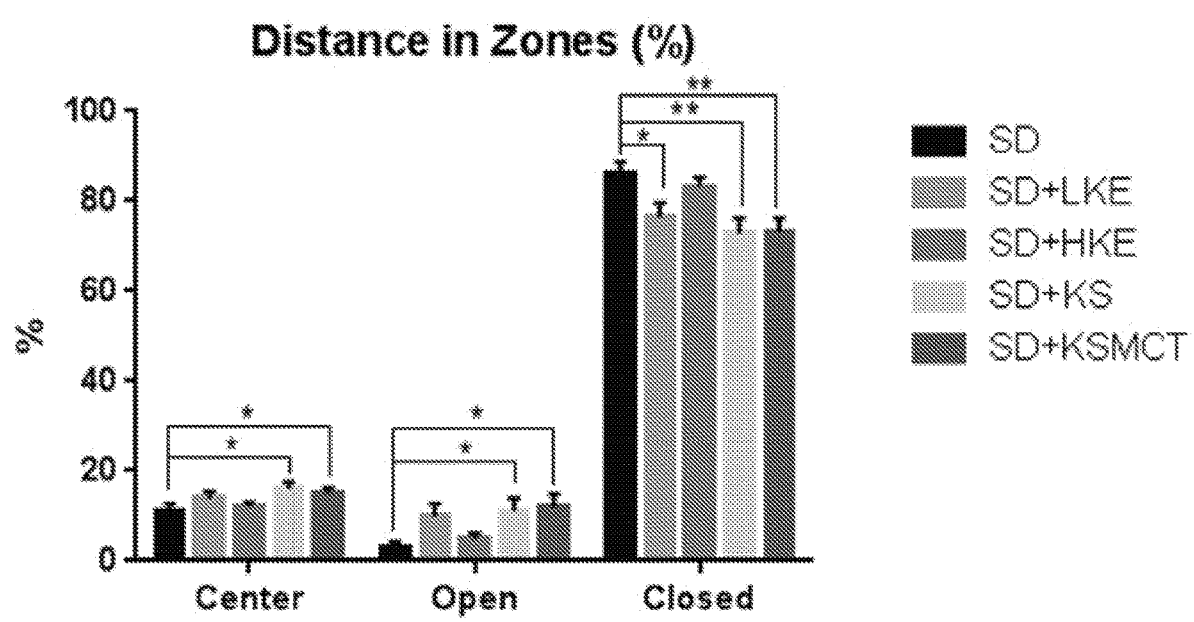

FIG. 5B shows that rats consuming ketone supplements travelled more distance in open arms (KS and KSMCT) and less in closed arms (LKE, KS and KSMCT), showing reduced anxiety compared to control group.

Figure 5C:
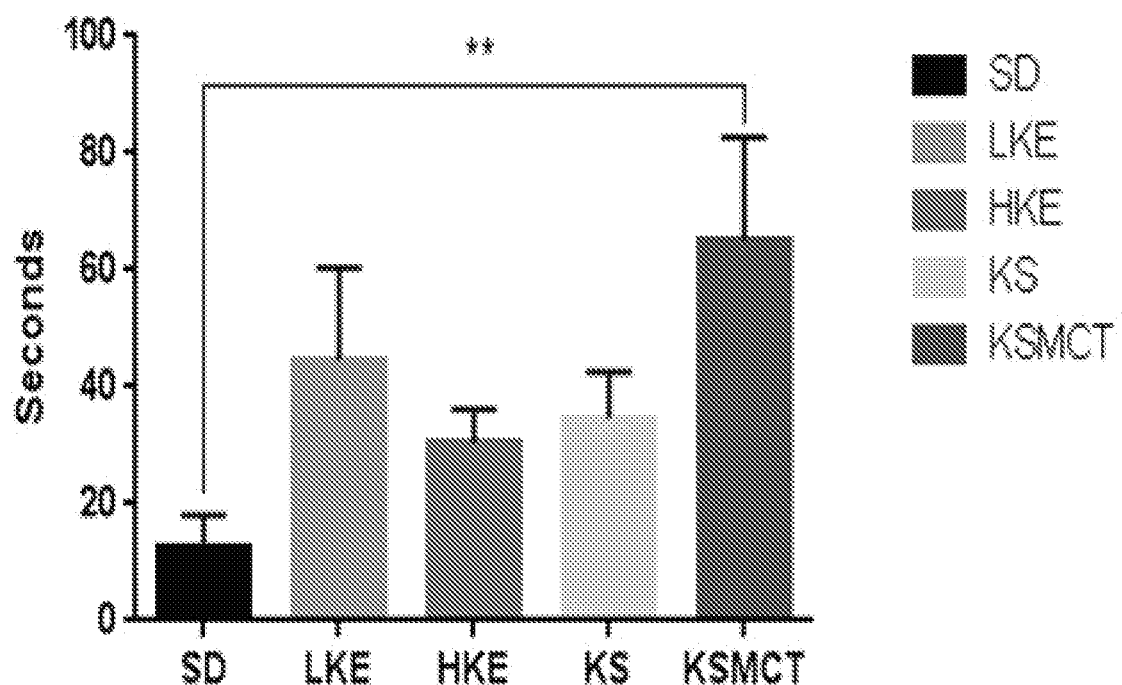

FIG. 5C shows that rats consuming KSMCT entered the closed arms later, evidencing reduced anxiety compared to control group.

Figure 5D:
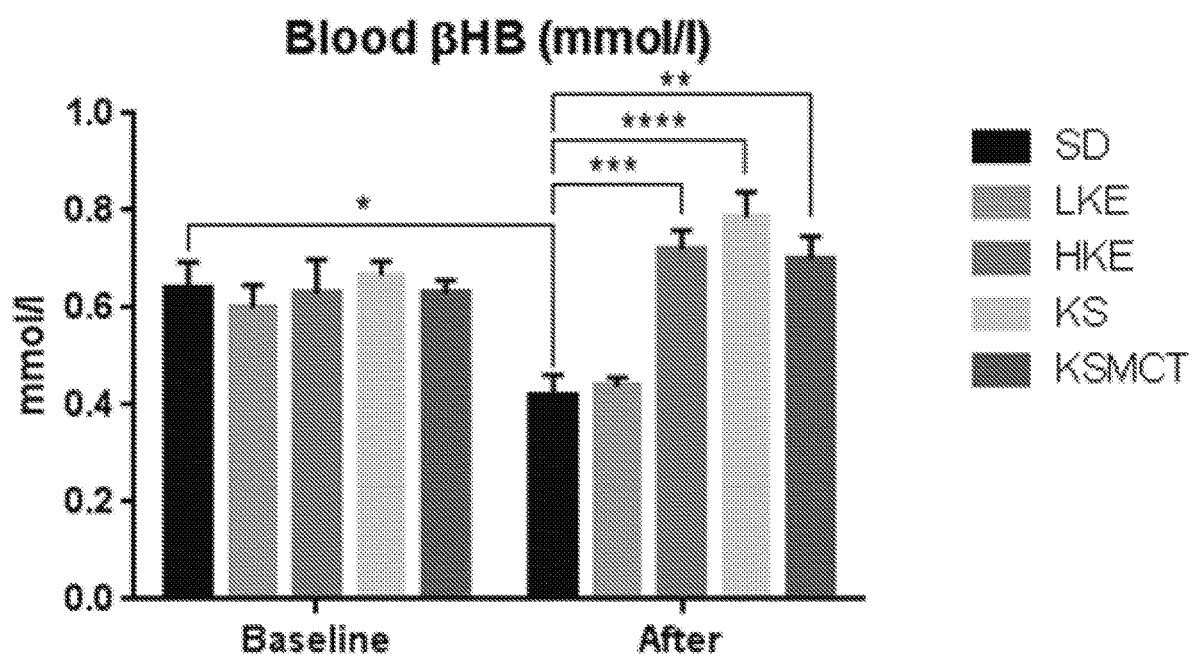

FIG. 5D shows that rats consuming HKE, KS and KSMCT had elevated blood ketone levels after 13 weeks (after) compared to control group.

Figure 5E:
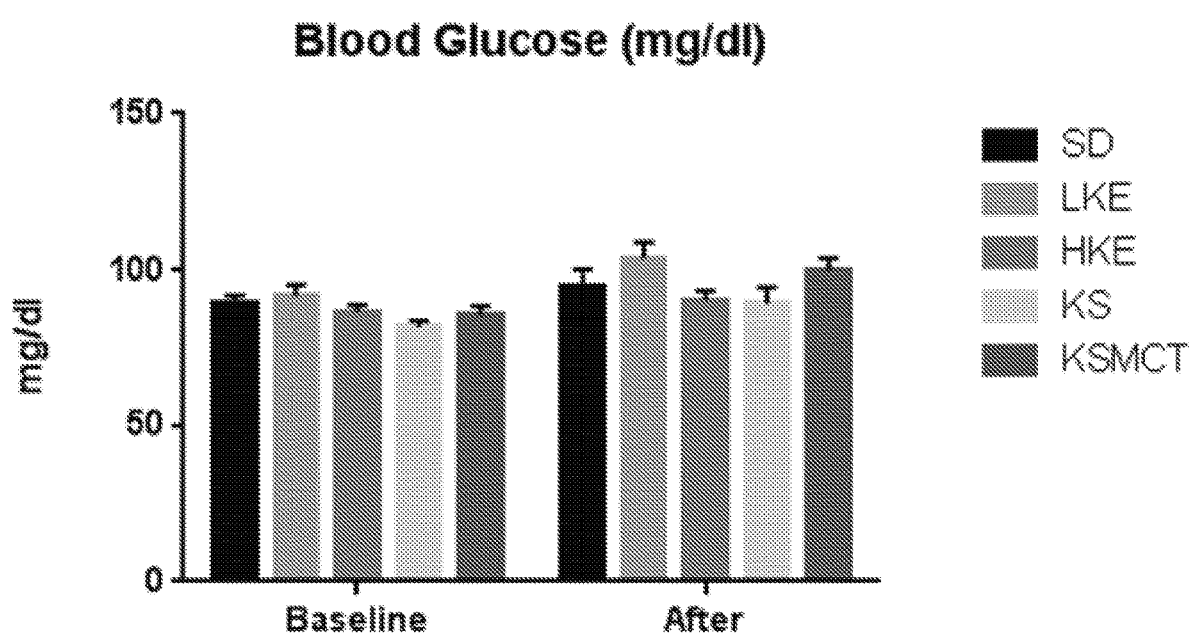

FIG. 5E shows that blood glucose levels were lower in HKE and KSMCT groups compared to control after 13 weeks.

Figure 5F:
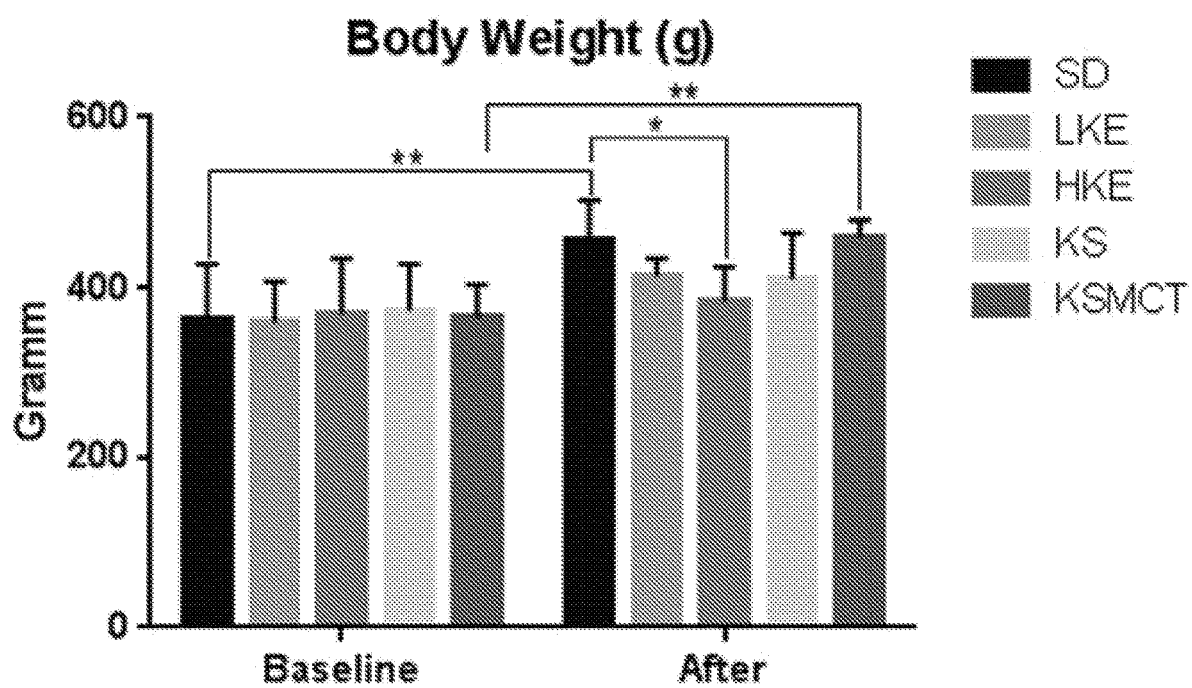

FIG. 5F shows that body weight was lower in HKE group after 13 weeks.

FIGS. 6A-6E depicts response of SPD rats to 7 days oral administration (gavage) of exogenous ketone supplementation. Abbreviations: SD: standard rodent chow+water (~5 g/kg b.w. water/day); KE: SD+ketone ester (1,3-butanediol-acetoacetate diester, ~5 g/kg b.w./day); KS: SD+beta-hydroxybutyrate-mineral salt (βHB-S) (~5 g/kg b.w./day); KSMCT: SD+βHB-S+medium chain triglyceride (MCT) (~5 g/kg b.w./day); (*p<0.05; p<0.01; *p<0.001; ****p<0.0001)

Figure 6A:
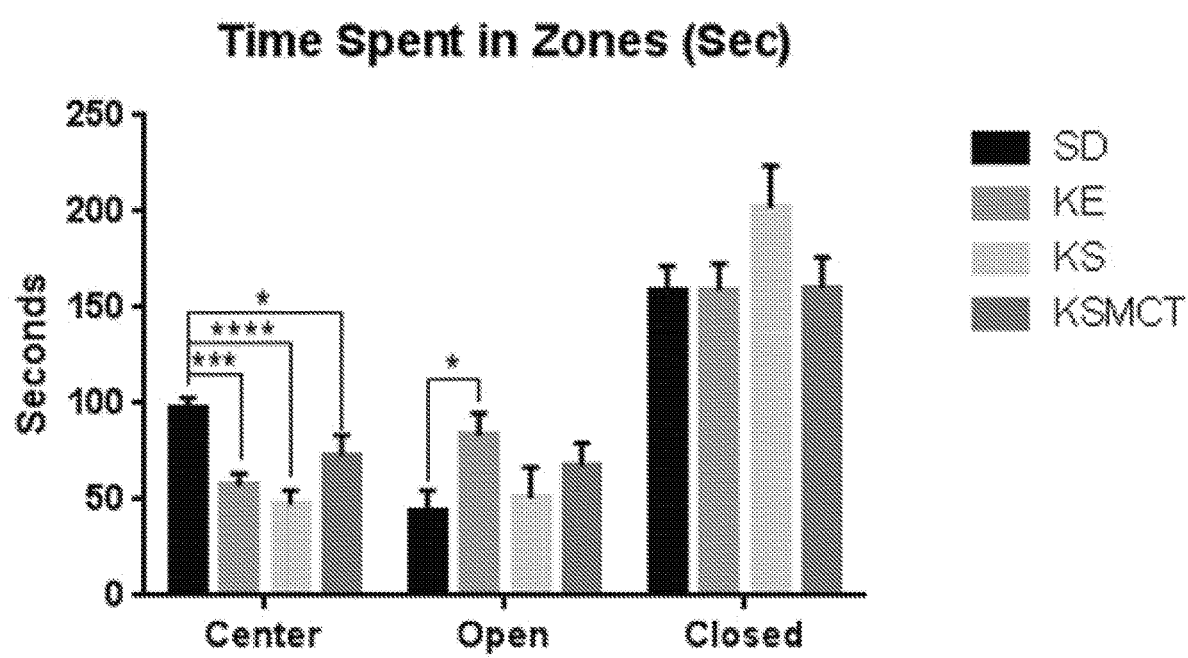

FIG. 6A depicts more time spent in open arms (open) by KE group and less time spent in center by KE, KS and KSMCT, compared to control.

Figure 6B:
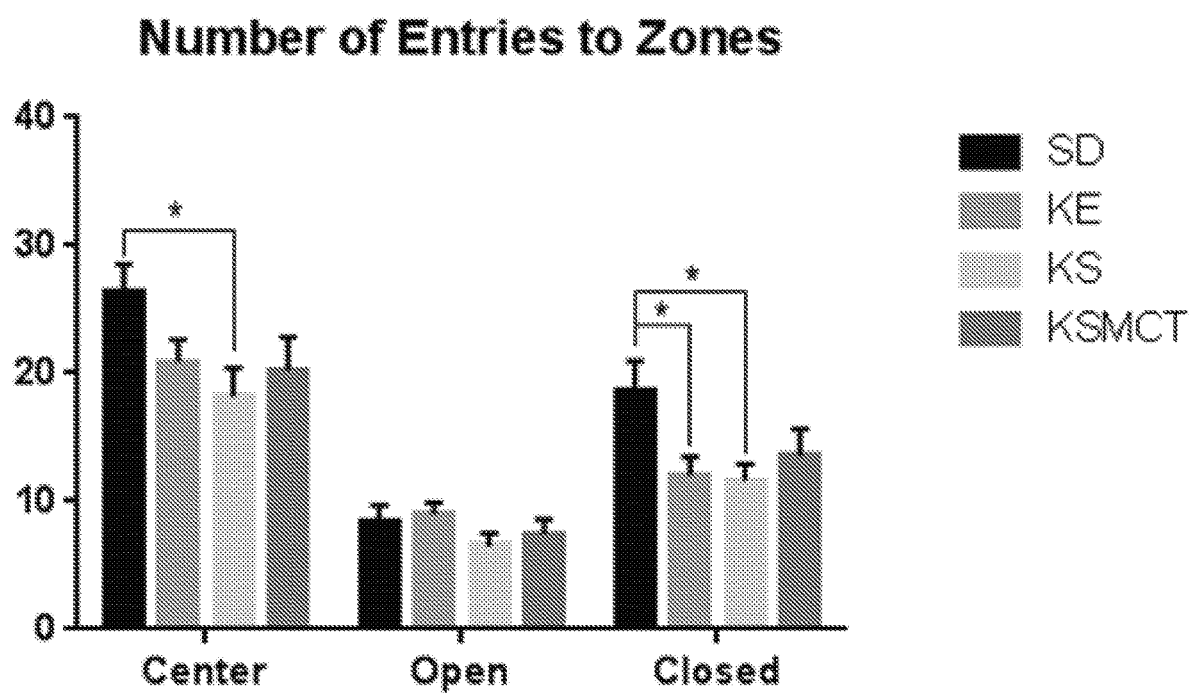

FIG. 6B depicts less entries in closed arms (closed) by KE and KS groups.

Figure 6C:
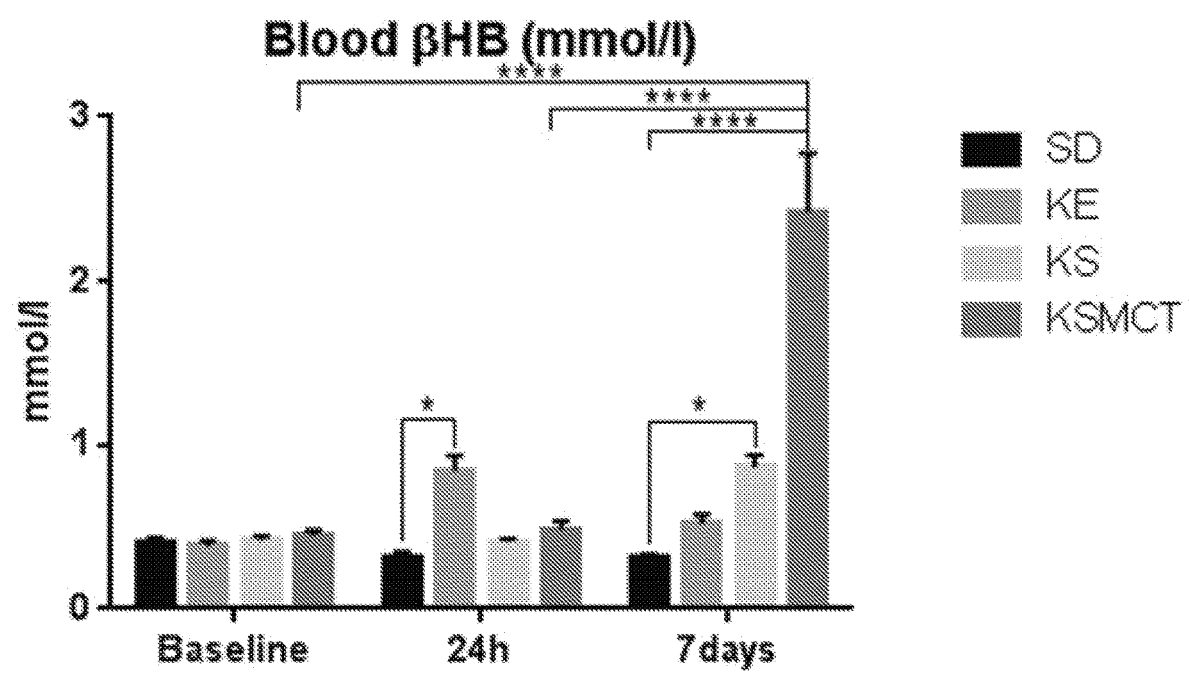

FIG. 6C shows that blood βHB levels were higher in KE group after 24 hours and in KS and KSMCT groups after 7 days, compared to control.

Figure 6D:
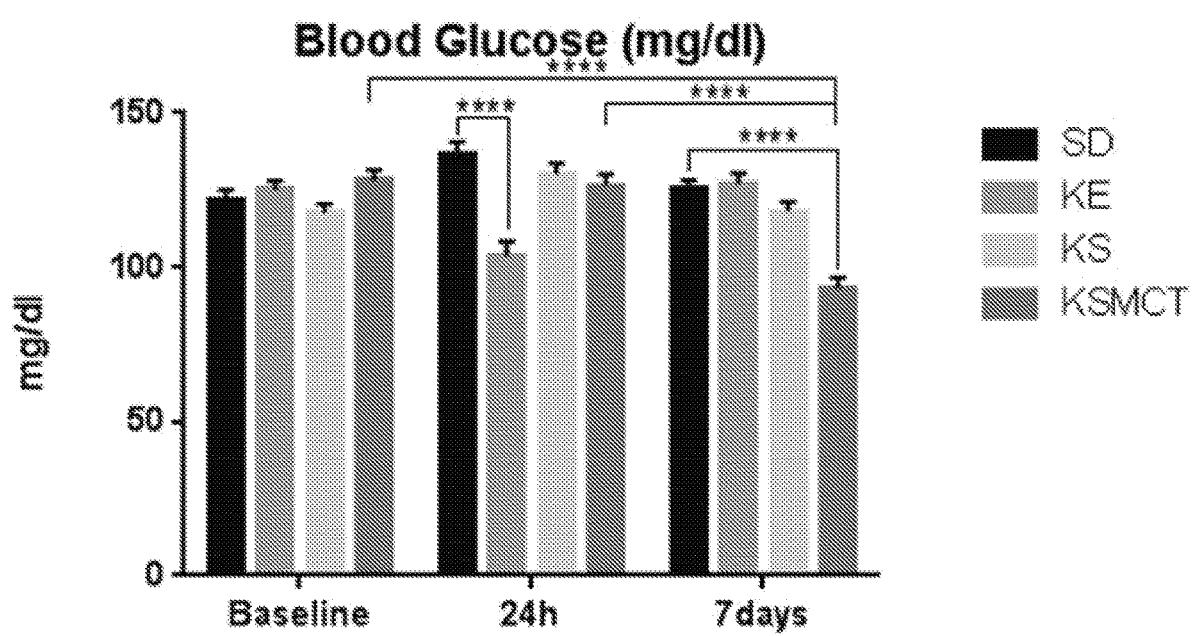

FIG. 6D shows that blood glucose levels were lower in KE group after 24 hours and in KSMCT group compared to baseline, control and 24 hours.

Figure 6E:
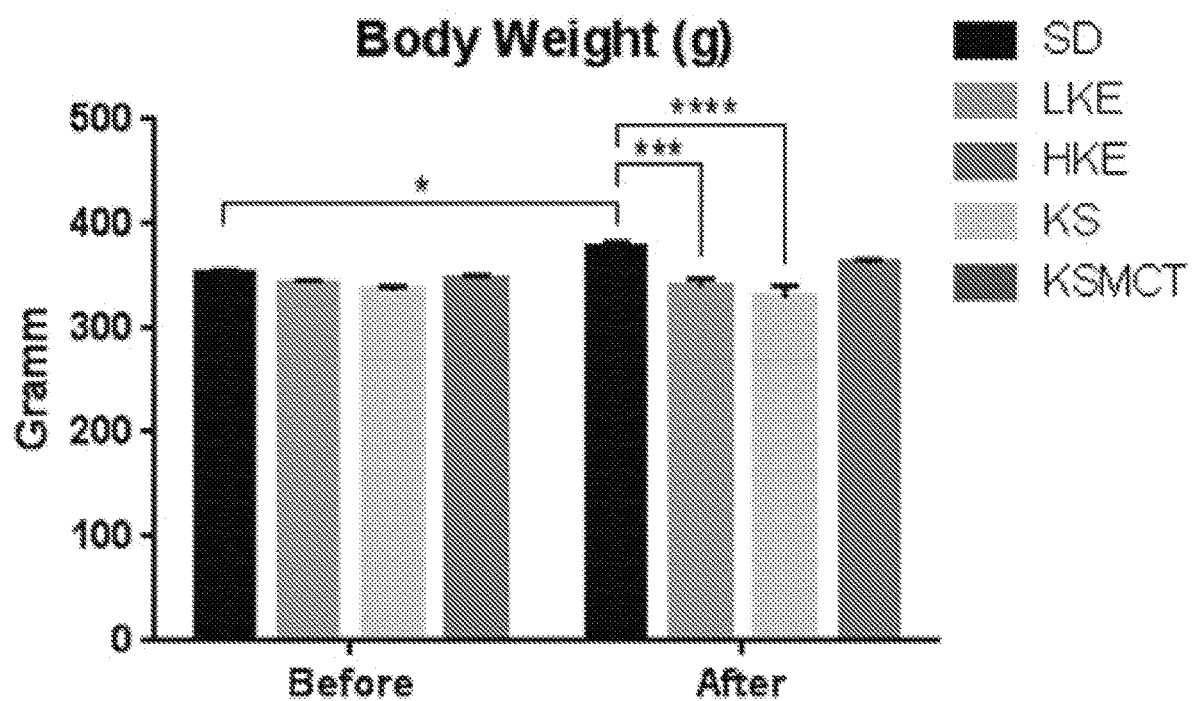

FIG. 6E depicts decreased body weights in KE and KS groups.

FIGS. 7A-7E depicts response of WAG/Rij rats to 7 days oral administration of exogenous ketone supplementation. Abbreviations: SD: standard rodent chow+water (~2.5 g/kg b.w. water/day); KE: SD+ketone ester (1,3-butanediol-acetoacetate diester, ~2.5 g/kg b.w./day); KS: SD+beta-hydroxybutyrate-mineral salt (βHB-S) (~2.5 g/kg b.w./day); KSMCT: SD+beta-hydroxybutyrate-mineral salt (BHB-S)+medium chain triglyceride (MCT) (KSMCT; ~2.5 g/kg b.w./day); (*p<0.05; p<0.01; *p<0.001; ****p<0.0001)

Figure 7A:
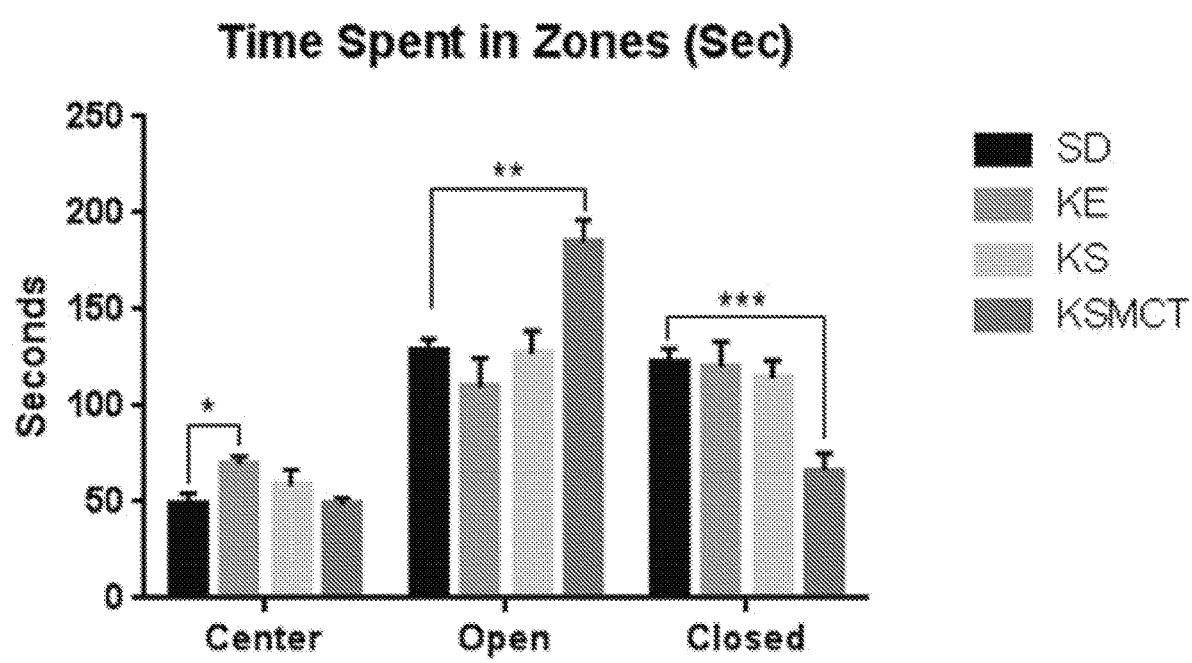

FIG. 7A depicts more time spent in open arms (open) and less time spent in closed arms (closed) by KSMCT group, compared to control.

Figure 7B:
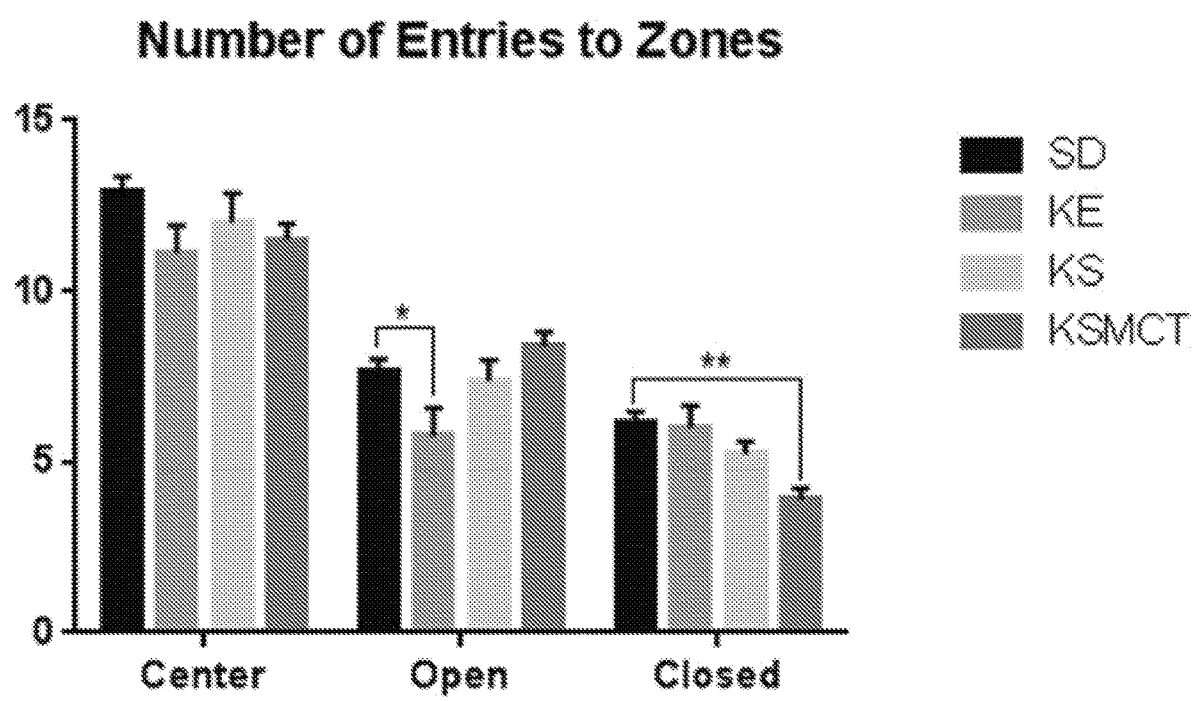

FIG. 7B depicts less entries in closed arms by KSMCT group and in open arms by KE group.

Figure 7C:
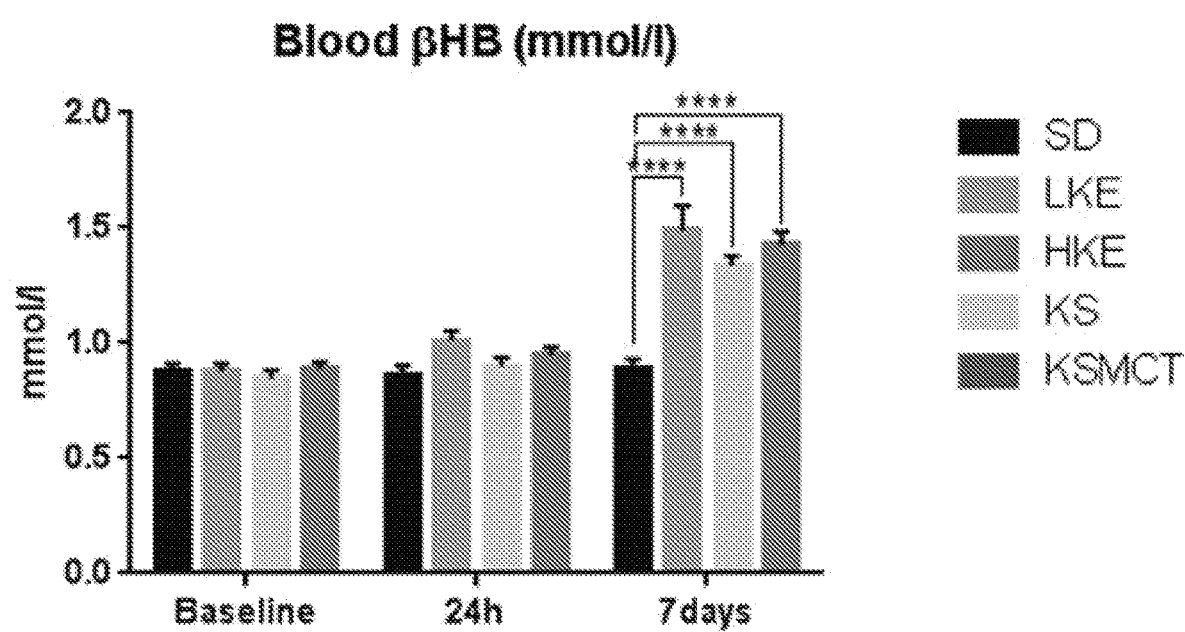

FIG. 7C shows that blood βHB levels were higher in all treatment groups (KE, KS and KSMCT) after 7 days, compared to baseline.

Figure 7D:
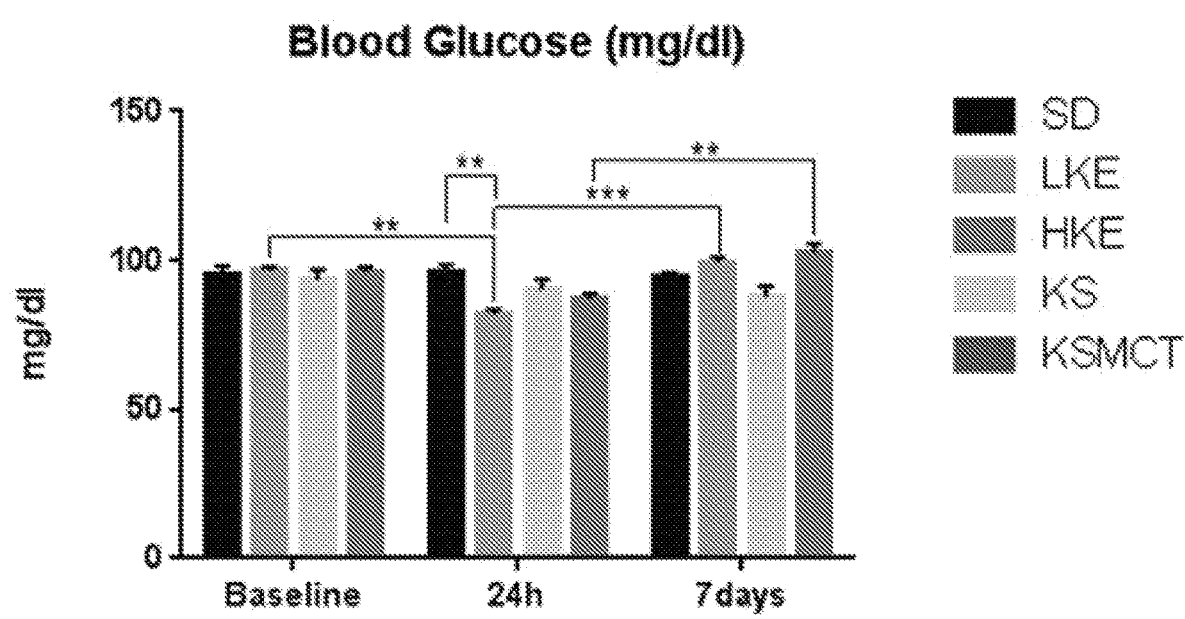

FIG. 7D shows that blood glucose levels decreased after 24 hours in KE group compared to baseline, but increased after 7 days compared to 24 hours in KE and KSMCT group.

Figure 7E:
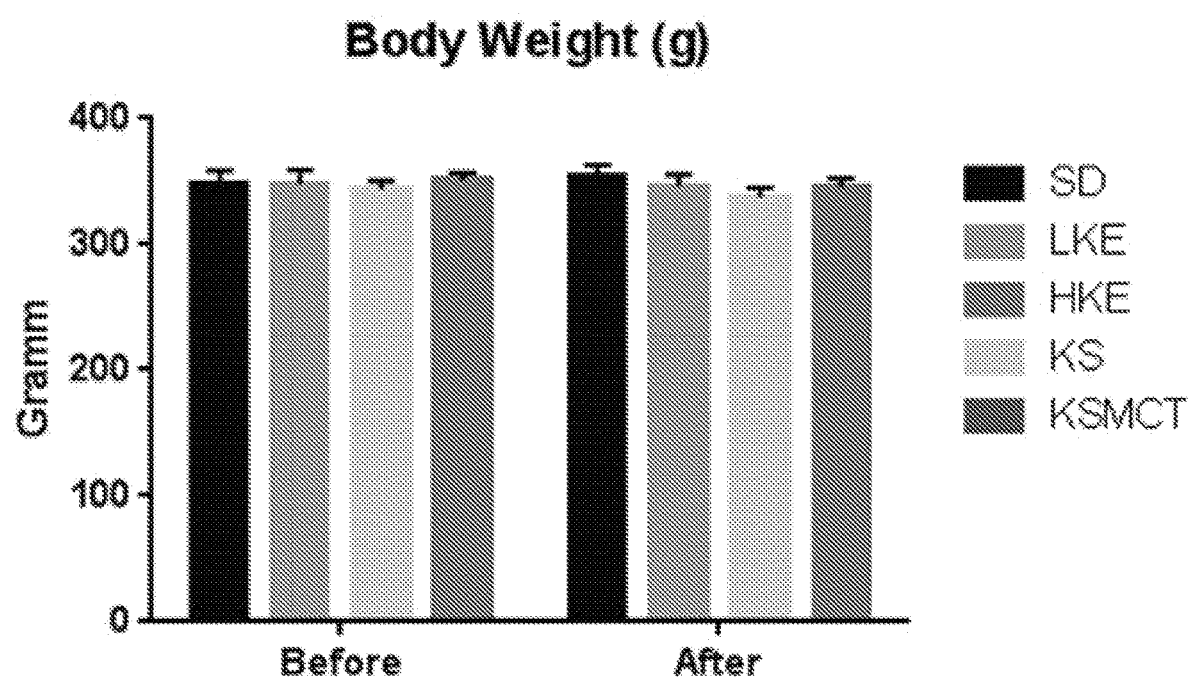

FIG. 7E shows that body weight did not change significantly in either group.

Figure 8A:
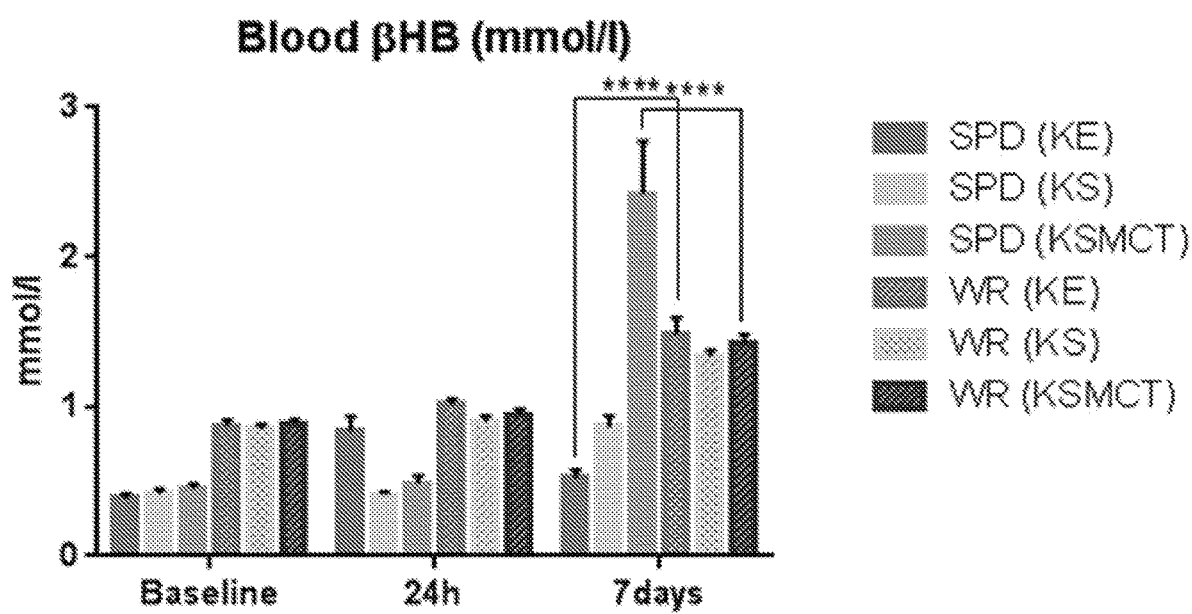
Figure 8B:
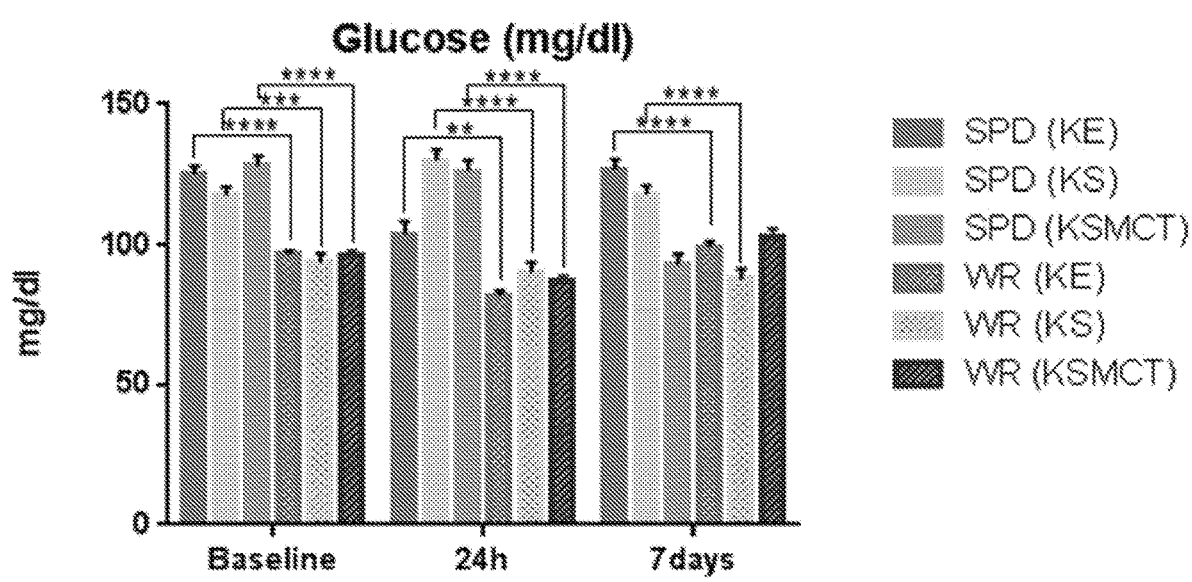

FIG. 8A-8B depict blood βHB and glucose levels compared between the two animal models. (p<0.01; **p<0.0001)

FIG. 8A shows that blood βHB levels were higher at 7 days in WAG/Rij rats after KE and KSMCT treatment.

FIG. 8B shows that blood glucose levels were significantly lower in WAG/Rij rats, except in KSMCT group at 7 days.

DETAILED DESCRIPTION OF THE PREFERRED EMBODIMENT

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

As used herein, "about" means approximately or nearly and in the context of a numerical value or range set forth means 15% of the numerical. In an embodiment, the term "about" can include traditional rounding according to significant figures of the numerical value. In addition, the phrase "about 'x' to 'y'" includes "about 'x' to about 'y'".

In certain embodiments, the current invention includes methods of treating or reducing anxiety-related behaviors. The methods include administering a therapeutically effective amount of ketone supplementation, such as butanediol, ketone esters and/or ketone salts, their combinations or combined with MCT chronically, sub-chronically or acutely (see aged rats).

As used herein, "treat", "treatment", "treating", and the like refer to acting upon a condition (e.g., anxiety-related behavior) with an agent (e.g., ketone supplementation) to affect the condition by improving or altering it. The improvement or alteration may include an improvement in symptoms or an alteration in the physiologic pathways associated with the condition. The aforementioned terms cover one or more treatments of a condition in a patient (e.g., a mammal, typically a human or non-human animal of veterinary interest), and includes: (a) reducing the risk of occurrence of the condition in a subject determined to be predisposed to the condition but not yet diagnosed, (b) impeding the development of the condition, and/or (c) relieving the condition, e.g., causing regression of the condition and/or relieving one or more condition symptoms (e.g., reduce anxiety-related behavior).

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a condition or symptom thereof and/or may be therapeutic in terms of a partial or complete cure or alleviation for a condition and/or adverse effect attributable to the condition.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

The term "therapeutically effective amount" as used herein describes concentrations or amounts of components such as agents which are effective for producing an intended result, including preventing further anxiety-related behavior, or treating anxiety-related behavior and related conditions. Compositions according to the present invention may be used to effect a favorable change in anxiety-related behavior, whether that change is an improvement, such as stopping or reversing the behavior, reducing levels of the behavior, or improving the behavior, relieve to some extent one or more of the symptoms of the condition being treated, and/or that amount that will prevent, to some extent, one or more of the symptoms of the condition that the host being treated has or is at risk of developing, or a complete cure of the disease or condition treated.

The term "administration" or "administering" is used throughout the specification to describe the process by which ketone supplementation or a composition comprising butanediol, beta-hydroxybutyrate or a ketone supplement (e.g., ketone ester, ketone salt, MCT) as an active agent, are delivered to a patient for therapeutic purposes. Ketone supplementation or the composition of the subject invention can be administered a number of ways including, but not limited to, parenteral (such term referring to intravenous and intra-arterial as well as other appropriate parenteral routes), subcutaneous, peritoneal, inhalation, vaginal, rectal, nasal, or instillation into body compartments.

Administration will often depend upon the amount of compound administered, the number of doses, and duration of treatment. In an embodiment, multiple doses of the agent are administered. The frequency of administration of the agent can vary depending on any of a variety of factors, such as extent of anxiety-related behavior, and the like. The duration of administration of the agent, e.g., the period of time over which the agent is administered, can vary, depending on any of a variety of factors, including patient response, etc.

The amount of the agent contacted (e.g., administered) can vary according to factors such as the degree of susceptibility of the individual, the age, sex, and weight of the individual, idiosyncratic responses of the individual, the dosimetry, and the like. Detectably effective amounts of the agent of the present disclosure can also vary according to instrument and film-related factors. Optimization of such factors is well within the level of skill in the art, unless otherwise noted.

As used herein, the term "subject," "patient," or "organism" includes humans and mammals (e.g., mice, rats, pigs, cats, dogs, and horses). Typical hosts to which an agent(s) of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range.

Study 1

Nutritional ketosis has been proven effective for seizure disorders and other neurological disorders. GLUT1 deficiency syndrome (G1D) is characterized by seizures resulting from impaired glucose metabolism in the brain. Anecdotal reports suggest that nutritional ketosis improves behavior and disposition in those with seizure disorders, including a reduction in anxiety-related behavior. An objective of this study was to determine the effects of ketone supplementation on anxiety-related behavior in Sprague-Dawley (SPD) and WAG/Rij rats.

I. Methods

Generally, exogenous ketone supplements were tested and fed chronically for 83 days and administered sub-chronically for 7 days by gavage, followed by assessment of anxiety measures on elevated plus maze (EPM) on 97 male SPD rats. The groups included standard diet (SD), ketogenic diet (KD), and SD+ketone supplementation (SD+KS). Ketone supplementation included ketone ester (KE) [low-dose ketone ester (LKE) (1,3-butanediol-acetoacetate diester, ~10 g/kg/day, SD+LKE) and high dose ketone ester (HKE) (1,3-butanediol-acetoacetate diester, ~25 g/kg/day, SD+HKE)], beta-hydroxybutyrate-mineral salt (βHB-S) (~25 g/kg/day, SD+KS), and βHB-S+medium chain triglyceride (MCT) (~25 g/kg/day, SD+KSMCT).

To extend the results and ensure that the results were not strain dependent, exogenous ketone supplements were tested on both SPD rats and Wistar Albino Glaxo/Rijswijk (WAG/Rij) rats for 7 days by gavage (5 g/kg/day and 2.5 g/kg/day, respectively, SD+KE and SD+KS), as WAG/Rij rats show reduced activity of GABAergic system (Luhmann H J, et al. Impairment of intracortical GABAergic inhibition in a rat model of absence epilepsy. Epilepsy Res. 1995 September; 22(1):43-51).

As background, the WAG/Rij rat strain was originally developed as an animal model of human absence epilepsy as the animals show spontaneous spike-wave discharges in the EEG (Coenen, A. M., et al, 2003. Genetic animal models for absence epilepsy: a review of the WAG/Rij strain of rats. Behav. Genet. 33, 635-655). Nevertheless, WAG/Rij rats are often used for investigation of different central nervous system (CNS) diseases, such as anxiety, similar to SPD rats by means of EPM (Kovács Z, et al. Facilitation of spike-wave discharge activity by lipopolysaccharides in Wistar Albino Glaxo/Rijswijk rats. Neuroscience. 2006 Jun. 30; 140(2):731-42; Kovács Z, et al. Neonatal tricyclic antidepressant clomipramine treatment reduces the spike-wave discharge activity of the adult WAG/Rij rat. Brain Res Bull. 2012 Nov. 1; 89(3-4):102-7; Kovács Z, et al. Absence epileptic activity changing effects of non-adenosine nucleoside inosine, guanosine and uridine in Wistar Albino Glaxo Rijswijk rats. Neuroscience. 2015 Aug. 6; 300:593-608; Sarkisova K Y, et al. Depressive-like behavioral alterations and c-fos expression in the dopaminergic brain regions in WAG/Rij rats with genetic absence epilepsy. Behav Brain Res. 2003 Sep. 15; 144(1-2):211-26; Sarkisova K Y, et al. Behavioral characteristics of WAG/Rij rats susceptible and non-susceptible to audiogenic seizures. Behav Brain Res. 2006 Jan. 6; 166(1):9-18; Sarkisova K, et al. The WAG/Rij strain: a genetic animal model of absence epilepsy with comorbidity of depression. Prog Neuropsychopharmacol Biol Psychiatry. 2011 Jun. 1; 35(4):854-76; Rebuli M E, et al. Impact of Low Dose Oral Exposure to Bisphenol A (BPA) on Juvenile and Adult Rat Exploratory and Anxiety Behavior: A CLARITY-BPA Consortium Study. Toxicol Sci. 2015 Jul. 23. pii: kfv163). Thus, the focus of this study was to test and determine the effects of different types of ketone supplementation on anxiety-related behavior by using EPM behavioral assay in two rat strains. Exogenous ketone supplements were fed chronically to SPD rats and administered sub-chronically to SPD rats and WAG/Rij rats and acutely to SPD rats prior to assessment of anxiety measures.

A. Animals

Three-month old male Sprague-Dawley rats (SPD, n=97) and eight-month old WAG/Rij (n=24) rats were used in the experiments. The animals were housed at Department of Molecular Pharmacology and Physiology (Hyperbaric Biomedical Research Laboratory, Morsani College of Medicine, University of South Florida, Tampa Fla., USA) and the Department of Zoology (University of West Hungary, Savaria Campus, Szombathely, Hungary). Animals were kept in groups of 2-4 under standard laboratory conditions (12:12 h light-dark cycle, light was on from 08.00 AM to 08.00 PM) in air-conditioned rooms at 22±2° C.

Animal treatment and measuring procedures were performed in accordance with the University of South Florida Institutional Animal Care and Use Committee (IACUC) guidelines (Protocol #0006R) and with the local ethical rules in accordance with the Hungarian Act of Animal Care and Experimentation (1998. XXVIII. Section 243/1998.) in conformity with the regulations for animal experimentation in the European Communities Council Directive of 24 Nov. 1986 (86/609/EEC). All efforts were made to reduce the number of animals used.

B. Synthesis and Formulation of Ketone Precursors

Ketone ester (KE, which is 1,3-butanediol-acetoacetate diester) was synthesized as previously described (D'Agostino, D., et al. (2013) Therapeutic ketosis with ketone ester delays central nervous system oxygen toxicity seizures in rats. *American Journal of Physiology. Regulatory, integrative and comparative physiology* 304(10):R829-36.doi:10.1152/ajpregu.00506.2012). Ketone salt (KS, which is $Na^+/K^+$-βHB mineral salt) is a novel agent that was mixed into a 50% solution supplying approximately 375 mg/g of pure βHB and 125 mg/g of $Na^+/K^+$. Accordingly, each dose of KS would equal ~1000-1500 mg of HB, depending on the weight of the animal. Both KE and KS were developed and synthesized in collaboration with Savind Inc. Human food grade MCT oil (~65% caprylic triglyceride) was purchased from Now Foods (Bloomingdale, Ill., USA). KS was mixed with medium chain triglyceride (MCT) in a 1:1 ratio (KSMCT) at the University of South Florida (USF, USA). Butanediol in aged rats.

C. Ketone Supplementation
i. Chronic Administration

In order to familiarize the animals to the intragastric gavage method, tap water was gavaged for 5 days before ketone supplementation. A total of 48 male SPD rats were fed for 83 days with either standard rodent chow (SD)+water application (~25 g/kg b.w. water/day) (SD/control group; n=9) or SD+ketone supplementation by gavage. Four treatment animal groups included low-dose KE (~10 g/kg b.w./day, SD+LKE group; n=10), high-dose KE (25 g/kg b.w./day, SD+HKE group; n=10), KS (~25 g/kg b.w./day, SD+KS group; n=9), and KSMCT (~25 g/kg b.w./day, SD+KSMCT group; n=10).

ii. Sub-Chronic Oral Gavage

Following the adaptation period to the intragastric gavage method, 51 male SPD rats were fed sub-chronically for 7 days with SD (SD/control group; n=11), KD (n=10) or gavaged daily with ketone supplements (5 g/kg b.w./day, SD+KE group: n=9, SD+KS group: n=9, SD+KSMCT group: n=10).

In addition, following the adaptation period to the intragastric gavage method, Wag/Rij male rats (n=24) were fed with SD and gavaged sub-chronically with ~2.5 g/kg b.w./day water (n=8, SD/control group), KE (n=8; SD+KE group) or KS (n=8; SD+KS group) for 7 days.

iii. Acute Oral Gavage

One year old SPD rats were gavaged and EPM test was performed 30 min after administration. Treatment groups BD, KE, KEMCT, KSMCT, KEKS.

D. Anxiety Assay

EPM (COULBOURN Instruments) was used to assess anxiety-related behavior of the rats after 83 days of chronic feeding or after 7 days of oral gavage. EPM experiments were carried out under non-stressful conditions (in a dimly lit and quiet room) between 12.00 and 14.00 hours.

As background, EPM is a widely used behavioral assay for rodents, and it has been validated to assess the anxiety responses of rodents (Pellow S, et al. Validation of open: closed arm entries in an elevated plus-maze as a measure of anxiety in the rat. J Neurosci Methods. 1985; 14:149-167; Walf, Alicia, et al. 2007. 'The Use of The Elevated Plus Maze As An Assay of Anxiety-Related Behavior in Rodents'. Nature Protocols 2 (2): 322-328. doi:10.1038/nprot.2007.44). This test relies upon rodents' proclivity toward dark enclosed spaces (approach) and an unconditioned fear of heights/open spaces (avoidance) (Barnett, S A. The Rat—A Study in Behavior. (Univ. Chicago Press, Chicago, 1975); Walf, Alicia, et al. 2007. 'The Use of The Elevated Plus Maze As An Assay of Anxiety-Related Behavior in Rodents'. Nature Protocols 2 (2): 322-328. doi: 10.1038/nprot.2007.44). EPM is an investigation method of anxiety that is primarily sensitive to benzodiazepine-type anxiolytics (e.g., diazepam) (Paslawski T, et al. The antidepressant drug phenelzine produces antianxiety effects in the plus-maze and increases in rat brain GABA. Psychopharmacology (Berl). 1996 September; 127(1):19-24. PubMed PMID: 8880939). Anti-anxiety behavior (increased open arm time and/or open arm entries) can be determined, which reflects the rodent's preference (or lack thereof) for protected areas (e.g., closed arms) and their innate motivation to explore novel environments (Walf, Alicia, et al. 2007. 'The Use of The Elevated Plus Maze As An Assay of Anxiety-Related Behavior in Rodents'. Nature Protocols 2 (2): 322-328. doi:10.1038/nprot.2007.44). Consequently, EPM assay on SPD and WAG/Rij rats was a suitable method for investigating the effect of ketone supplementation-evoked changes on anxiety level and anxiety-related behaviors.

The rats were transferred in their home cage to the experimental room 30 min prior to beginning the experiment. Briefly, rats were placed in the intersection of the four arms of the EPM, facing the open arm opposite to where the experimenter was and their behavior was recorded for 5 minutes. The amount of time spent and number of entries made on the open arms, closed arms and the center zones were recorded. Latency to entry into the closed arms and the distance travelled in each zones was also measured in chronically treated SPD rats. Notes were made on other ethological measures such as number of rears, head dips, fecal boli, and freezing, or stretched-attend postures.

At the end of the 5-minute test the rats were removed from the maze and placed back into their home cage. The maze was cleaned with 70% alcohol and after it with tap water and dried with paper towel between rats. The primary method for data collection was a video-tracking system with computer interface and video camera (SMART V3.0 PLATFORM, PANLAB, Harvard Apparatus, USA), to automatically collect behavioral data in SPD rats. A blinded observer was present in the testing room separated from the maze by a curtain, and manually collected EPM data in both SPD and WAG/Rij animals at the end of treatments.

E. Blood Analyses and Weight Measurement

In the chronic feeding study, blood 3HB and glucose levels were measured 24 hours before the $1^{st}$ day of ketone treatments (baseline levels) and after the $13^{th}$ week of ketone treatment. In the 7-day oral gavage studies, blood βHB and glucose levels were measured 24 hours before the $1^{st}$ day of ketone treatments (baseline levels; SPD and WAG/Rij rats) and after the $1^{st}$ day (SPD rats) and the $7^{th}$ day (SPD and WAG/Rij rats) of ketone gavaging. In acute study, blood βHB and glucose levels were measured 40 min after ketone treatment. Whole blood samples (10 μL) were taken from the saphenous vein for analysis of blood glucose (mg/dl) and βHB (mmol/l) levels with the commercially available glucose and ketone monitoring system PRECISION XTRA™ (ABBOTT Laboratories, Abbott Park, Ill., USA). The PRECISION XTRA™ ketone monitoring system only measures βHB blood levels; therefore, total blood ketone levels would be higher than measured.

The body weight of all animals was recorded before ketone treatments started (before) and after the last ketone treatments (after).

F. Statistics

All data are presented as the mean standard error of the mean (SEM). The effects of ketone supplementations on anxiety level were compared, as well as on blood βHB and glucose levels to control or/and baseline levels. Data analysis was performed using GraphPad PRISM version 6.0a. Results were considered significant when $p<0.05$. Significance was determined by unpaired t-test. Blood ketone, blood glucose, and body weight change were compared using a two-way ANOVA with Tukey's multiple comparisons test and unpaired t-test.

II. Results

It was determined herein that, when compared to control (no ketone supplementation), ketone supplementation reduced anxiety in rats on EPM as measured by less entries to closed arms (sub-chronic SD+KS: SPD and WAG/Rij rats), more time spent in open arms (sub-chronic SD+KS: SPD and WAG/Rij rats; chronic SD+KS/KSMCT: SPD rats), more distance travelled in open arms (chronic SD+KS/KSMCT: SPD rats), and delayed latency to entrance to closed arms (chronic SD+HKE/KS/KSMCT: SPD rats). The chronic and sub-chronic ketone supplements also caused significant elevation of blood βHB levels and changed blood glucose levels. This data indicates that chronic and sub-chronic ketone supplementation not only elevated blood ketone levels in both animal models, but reduced anxiety-related behavior. These influences may also be highly beneficial for patients managing diseases with nutritional ketosis.

A. Ketone Supplementation Reduced Anxiety on Elevated Plus Maze i. Less Entries to Closed Arms with Ketone Supplements Entries to the closed arms were less frequent with SD+KS treatment in both rat models after 7 days of gavaging (FIGS. 2A and 3A; p=0.026; 0.00046). SPD rats also entered fewer times to the center when treated with SD+KS (FIG. 2A; p=0.016) compared to control (SD) animals.

ii. More Time Spent in Open Arms with Ketone Supplements

Figure 1A:
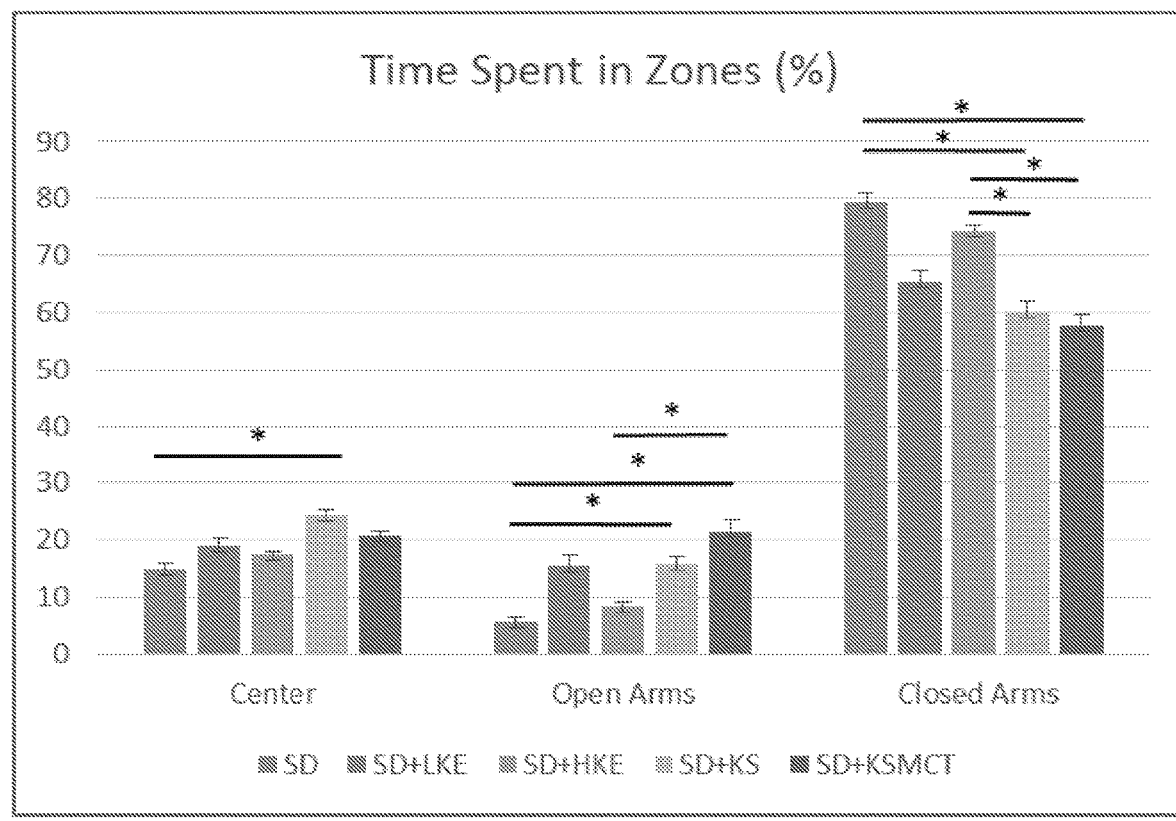
FIGS. 1A-1E depict response of SPD (Sprague-Dawley) rats to chronic feeding of exogenous ketone supplementation. Abbreviations: SD: standard rodent chow+water (~25 g/kg b.w. water/day); SD+LKE: SD+low-dose ketone ester (1,3-butanediol-acetoacetate diester, ~10 g/kg b.w./day); SD+HKE: SD+high dose ketone ester (~25 g/kg b.w./day); SD+KS: SD+beta-hydroxybutyrate-mineral salt (βHB-S) (~25 g/kg b.w./day); SD+KSMCT: SD+βHB-S+medium chain triglyceride (MCT) (~25 g/kg b.w./day); ($*p<0.05$; $p<0.01$; $*p<0.001$; $****p<0.0001$).

After chronic feeding the time spent in the open arms was significantly more in SD+KS and SD+KSMCT groups (p=0.017 and 0.022, respectively), while time spent in the closed arms was significantly less (p=0.01 and 0.005) in these groups, compared to the control (SD). Time spent in the center was significantly more (p=0.04) in SD+KS group (FIG. 1A). Also seen in FIG. 1A, time spent in open arms were significantly more in SD+KS and SD+KSMCT groups (p=0.017 and 0.022, respectively), while time spent in closed arms were significantly less (p=0.01; 0.005) in these groups, compared to control (SD). Time spent in the center was significantly more (p=0.04) in SD+KS group.

After 7 days of gavaging SPD rats, the time spent in the open arms increased in the SD+KE group, whereas time spent in the center decreased in KD, SD+KE and SD+KS groups (FIG. 2B). In WAG/Rij rats the SD+KS treated rats spent more time in the open arms and less time in the closed arms, whereas SD+KE treated rats spent more time in the center (FIG. 3B) compared to the control (SD) group.

iii. Delayed Latency of Entrance to Closed Arms with Ketone Supplements

Figure 1B:
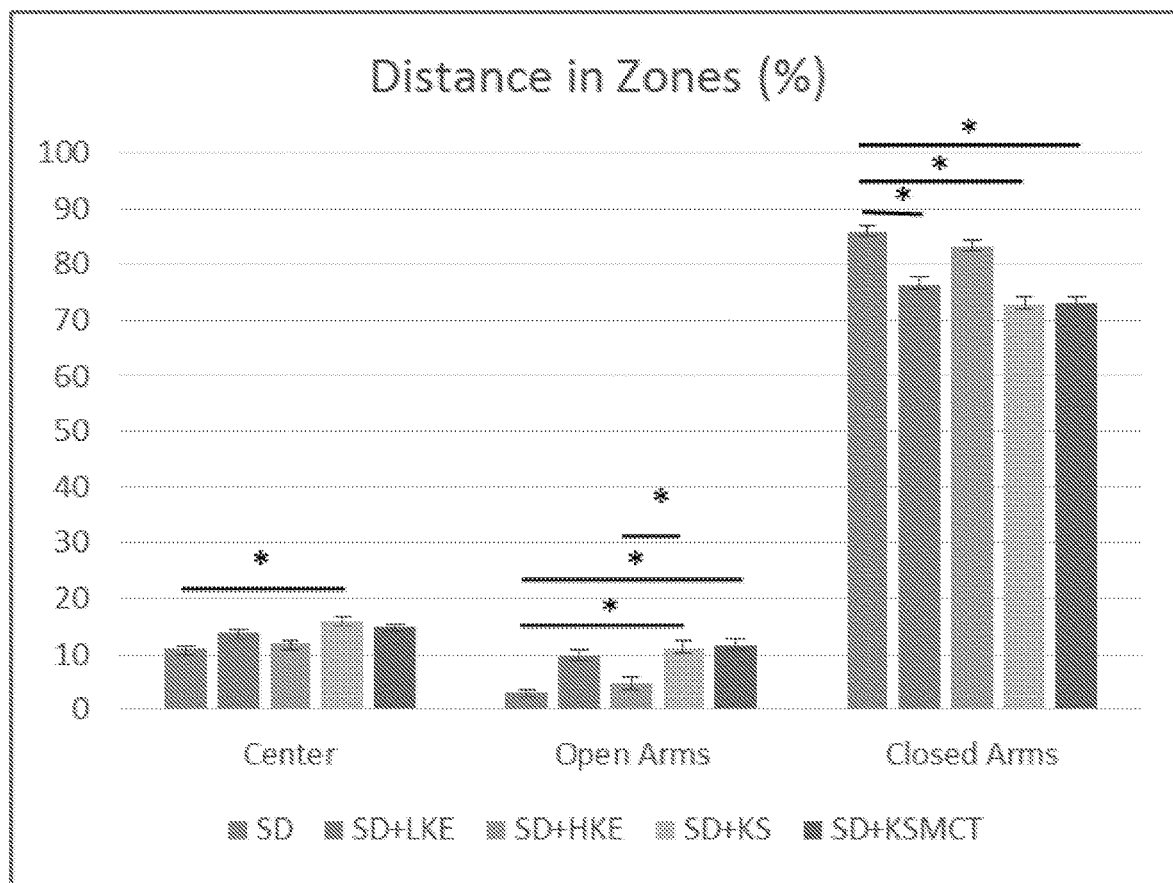
Figure 1C:
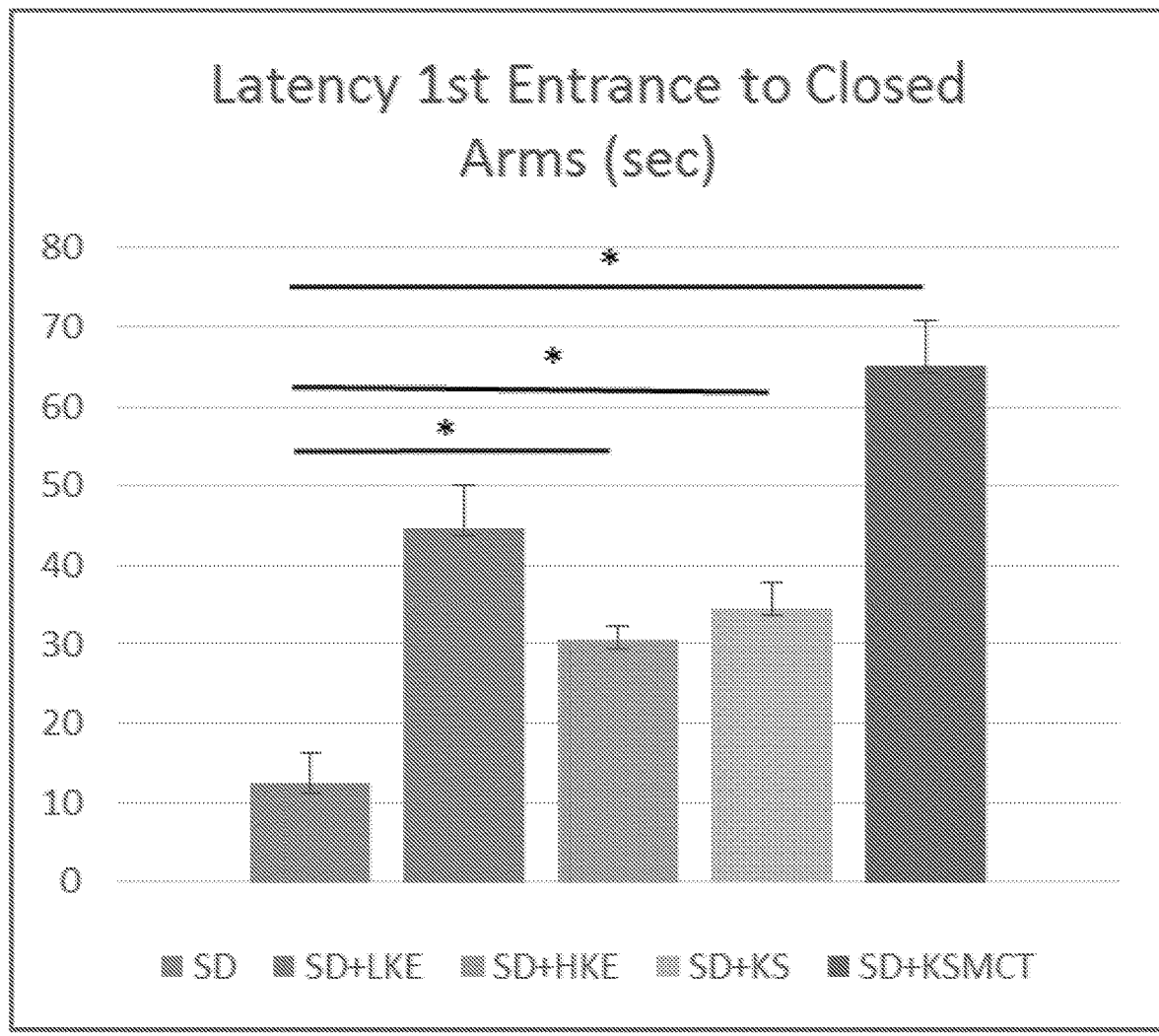

The latency to first entrance of closed arms was significantly greater in SD+HKE, SD+KS and SD+KSMCT groups after chronic feeding (p=0.037, 0.034 and 0.014, respectively) (FIG. 1C). Also seen in FIG. 1C, latency to first entrance to closed arms was significantly higher in HKE, SD+KS and SD+KSMCT groups (p=0.037; 0.035; 0.015, respectively), compared to control (SD).

iv. More Distance Traveled in Open Arms with Ketone Supplements

After chronic feeding, the distance traveled in the open arms was significantly greater in SD+KS and SD+KSMCT groups (p=0.02 and 0.02), and distance traveled in the closed arms was significantly less in SD+LKE, SD+KS and SD+KSMCT groups (p=0.04, 0.009 and 0.007), compared to the control (SD). Distance traveled in the center was more in SD+KS group (p=0.046; FIG. 1B). Also seen in FIG. 1B, distance travelled in open arms were significantly more in SD+KS and SD+KSMCT groups (p=0.02; 0.02), and distance travelled in closed arms were significantly less in LKE, SD+KS and SD+KSMCT groups (p=0.04; 0.009; 0.007), compared to control (SD). Distance travelled in the center was more in SD+KS group (p=0.046).

B. Elevation of Blood/βHB Levels with Ketone Supplements

Figure 1D:
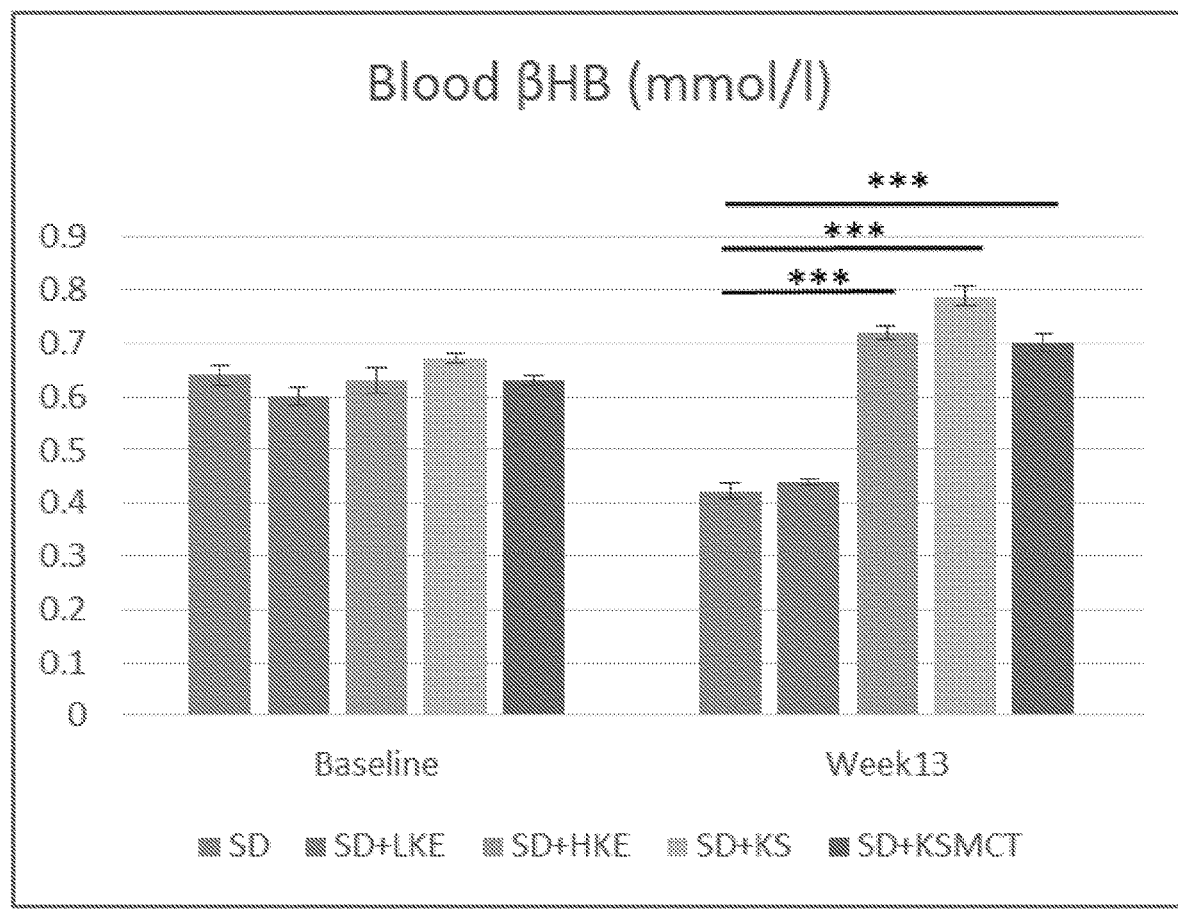
Figure 1E:
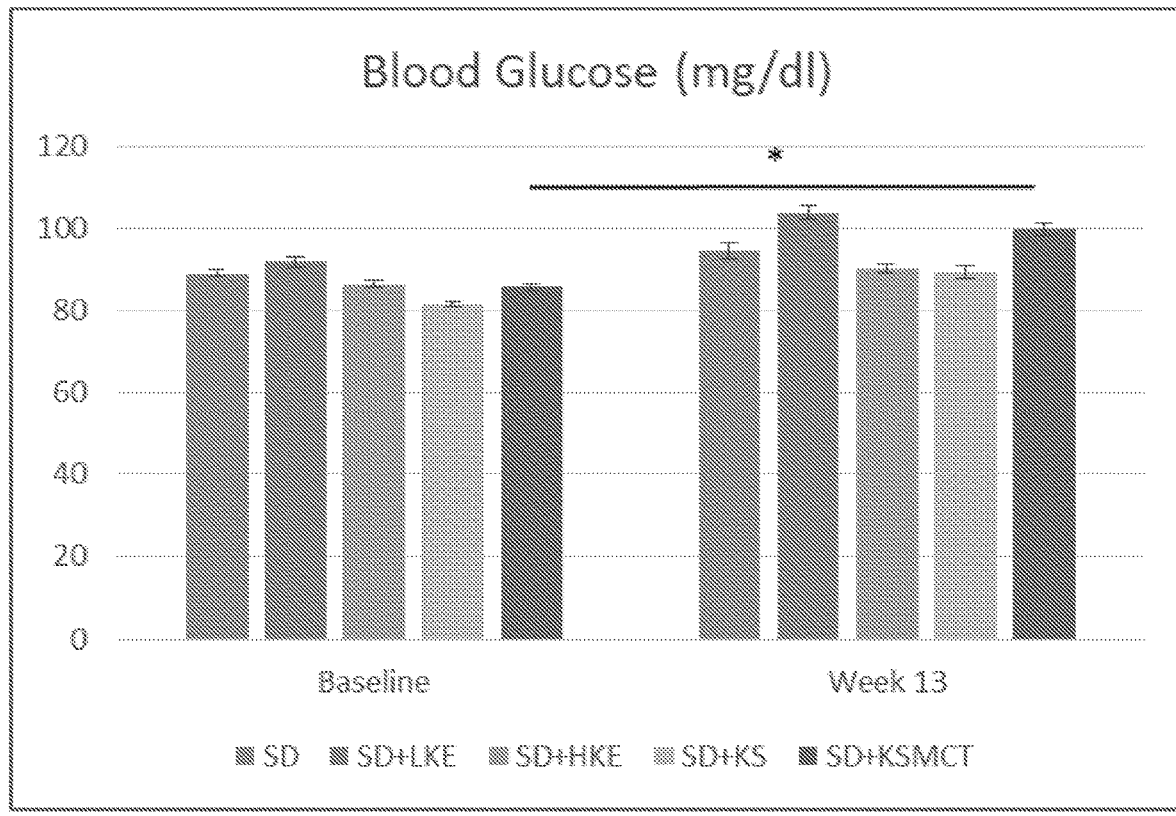

After 83 days of chronic feeding in SPD rats, blood βHB was elevated in SD+HKE, SD+KS and SD+KSMCT treatment groups (p=5,5E-05; 4,5E-05; 0,0004, respectively), compared to control (FIG. 1D, Table 1).

TABLE 1

| Tukey's multiple comparisons test | Mean Diff. | 95% CI of diff. | Significant? | Summary |
|---|---|---|---|---|
| Blood βHB (90 days) | | | | |
| Baseline: SD vs. After: SD | 0.2178 | 0.01103 to 0.4245 | Yes | * |
| Baseline: SD + HKE vs. After: SD | 0.2078 | 0.001033 to 0.4145 | Yes | * |
| Baseline: SD + KS vs. After: SD | 0.2444 | 0.03233 to 0.4566 | Yes | * |
| Baseline: SD + KS vs. After: SD + LKE | 0.2267 | 0.01992 to 0.4334 | Yes | * |
| Baseline: SD + KSMCT vs. After: SD | 0.2078 | 0.001033 to 0.4145 | Yes | * |
| After: SD vs. After: SD + HKE | −0.2978 | −0.5045 to −0.09103 | Yes | *** |
| After: SD vs. After: SD + KS | −0.3653 | −0.5839 to −0.1466 | Yes | **** |
| After: SD vs. After: SD + KSMCT | −0.2778 | −0.4845 to −0.07103 | Yes | ** |
| After: SD + LKE vs. After: SD + HKE | −0.28 | −0.4812 to −0.07877 | Yes | *** |
| After: SD + LKE vs. After: SD + KS | −0.3475 | −0.5609 to −0.1341 | Yes | **** |
| After: SD + LKE vs. After: SD + KSMCT | −0.26 | −0.4612 to −0.05877 | Yes | ** |
| Blood Glucose (90 days) | | | | |
| Baseline: SD + HKE vs. After: SD + LKE | −17.3 | −33.96 to −0.6428 | Yes | * |
| Baseline: SD + KS vs. After: SD + LKE | −22.24 | −39.36 to −5.131 | Yes | ** |
| Baseline: SD + KS vs. After: SD + KSMCT | −18.24 | −35.36 to −1.131 | Yes | * |
| Baseline: SD + KSMCT vs. After: SD + LKE | −18.1 | −34.76 to −1.443 | Yes | * |
| Body Weight (90 days) | | | | |
| Baseline: SD vs. After: SD | −95.7 | −167.2 to −24.19 | Yes | ** |
| Baseline: SD vs. After: SD + KSMCT | −97.41 | −167.0 to −27.81 | Yes | *** |
| Baseline: SD + LKE vs. After: SD | −97.81 | −169.3 to −26.30 | Yes | ** |
| Baseline: SD + LKE vs. After: SD + KSMCT | −99.52 | −169.1 to −29.92 | Yes | *** |
| Baseline: SD + HKE vs. After: SD | −88.9 | −160.4 to −17.39 | Yes | ** |
| Baseline: SD + HKE vs. After: SD + KSMCT | −90.61 | −160.2 to −21.01 | Yes | ** |
| Baseline: SD + KS vs. After: SD | −84.77 | −156.3 to −13.26 | Yes | ** |
| Baseline: SD + KS vs. After: SD + KSMCT | −86.48 | −156.1 to −16.88 | Yes | ** |
| Baseline: SD + KSMCT vs. After: SD | −92.65 | −164.2 to −21.14 | Yes | ** |
| Baseline: SD + KSMCT vs. After: SD + KSMCT | −94.36 | −164.0 to −24.76 | Yes | ** |
| After: SD vs. After: SD + HKE | 73.96 | 2.453 to 145.5 | Yes | * |
| After: SD + HKE vs. After: SD + KSMCT | −75.67 | −145.3 to −6.071 | Yes | * |

Blood βHB levels were elevated in SPD rats after 24 hours of a single gavage in KD and SD+KE groups (FIG. 2C; p=1.67E-06; 0.00015), compared to baseline. The levels were also elevated in all treatment groups after 7 days of administration, compared to the control (SD) group (FIG. 2C, Table 2).

TABLE 2

| Blood βHB (7 days) | | | | |
|---|---|---|---|---|
| Tukey's multiple comparisons test | Mean Diff. | 95% CI of diff. | Significant? | Summary |
| Baseline: SD vs. 24 h: KD | −0.7182 | −1.221 to −0.2153 | Yes | *** |
| Baseline: SD vs. 7 days: KD | −0.68 | −1.196 to −0.1641 | Yes | ** |
| Baseline: SD vs. 7 days: SD + KSMCT | −2.018 | −2.521 to −1.515 | Yes | **** |
| Baseline: KD vs. 24 h: KD | −0.5273 | −1.041 to −0.01354 | Yes | * |
| Baseline: KD vs. 7 days: SD + KSMCT | −1.827 | −2.341 to −1.314 | Yes | **** |
| Baseline: SD + KE vs. 24 h: KD | −0.7348 | −1.238 to −0.2319 | Yes | *** |
| Baseline: SD + KE vs. 7 days: KD | −0.6967 | −1.213 to −0.1808 | Yes | *** |
| Baseline: SD + KE vs. 7 days: SD + KSMCT | −2.035 | −2.538 to −1.532 | Yes | **** |
| Baseline: SD + KS vs. 24 h: KD | −0.7 | −1.214 to −0.1863 | Yes | *** |
| Baseline: SD + KS vs. 7 days: KD | −0.6618 | −1.188 to −0.1354 | Yes | ** |
| Baseline: SD + KS vs. 7 days: SD + KSMCT | −2 | −2.514 to −1.486 | Yes | **** |
| Baseline: SD + KSMCT vs. 24 h: KD | −0.6682 | −1.171 to −0.1653 | Yes | *** |
| Baseline: SD + KSMCT vs. 7 days: KD | −0.63 | −1.146 to −0.1141 | Yes | ** |
| Baseline: SD + KSMCT vs. 7 days: SD + KSMCT | −1.968 | −2.471 to −1.465 | Yes | **** |
| 24 h: SD vs. 24 h: KD | −0.8 | −1.314 to −0.2863 | Yes | **** |
| 24 h: SD vs. 24 h: SD + KE | −0.5235 | −1.026 to −0.02057 | Yes | * |
| 24 h: SD vs. 7 days: KD | −0.7618 | −1.288 to −0.2354 | Yes | *** |
| 24 h: SD vs. 7 days: SD + KS | −0.5455 | −1.059 to −0.03172 | Yes |  |
| 24 h: SD vs. 7 days: SD + KSMCT | −2.1 | −2.614 to −1.586 | Yes | **** |
| 24 h: KD vs. 24 h: SD + KS | 0.7098 | 0.2069 to 1.213 | Yes | *** |
| 24 h: KD vs. 24 h: SD + KSMCT | 0.6348 | 0.1319 to 1.138 | Yes | ** |
| 24 h: KD vs. 7 days: SD | 0.8015 | 0.2986 to 1.304 | Yes | **** |
| 24 h: KD vs. 7 days: SD + KE | 0.596 | 0.05444 to 1.137 | Yes | * |
| 24 h: KD vs. 7 days: SD + KSMCT | −1.3 | −1.814 to −0.7863 | Yes | **** |
| 24 h: SD + KE vs. 7 days: SD | 0.525 | 0.03314 to 1.017 | Yes | * |
| 24 h: SD + KE vs. 7 days: SD + KSMCT | −1.577 | −2.079 to −1.074 | Yes | **** |
| 24 h: SD + KS vs. 7 days: KD | −0.6717 | −1.188 to −0.1558 | Yes | ** |
| 24 h: SD + KS vs. 7 days: SD + KSMCT | −2.01 | −2.513 to −1.507 | Yes | **** |
| 24 h: SD + KSMCT vs. 7 days: KD | −0.5967 | −1.113 to −0.08080 | Yes | ** |
| 24 h: SD + KSMCT vs. 7 days: SD + KSMCT | −1.935 | −2.438 to −1.432 | Yes | **** |
| 7 days: SD vs. 7 days: KD | −0.7633 | −1.279 to −0.2475 | Yes | **** |
| 7 days: SD vs. 7 days: SD + KS | −0.547 | −1.050 to −0.04406 | Yes | * |
| 7 days: SD vs. 7 days: SD + KSMCT | −2.102 | −2.604 to −1.599 | Yes | **** |
| 7 days: KD vs. 7 days: SD + KE | 0.5578 | 0.004209 to 1.111 | Yes | * |
| 7 days: KD vs. 7 days: SD + KSMCT | −1.338 | −1.865 to −0.8118 | Yes | **** |
| 7 days: SD + KE vs. 7 days: SD + KSMCT | −1.896 | −2.437 to −1.354 | Yes | **** |
| 7 days: SD + KS vs. 7 days: SD + KSMCT | −1.555 | −2.068 to −1.041 | Yes | **** |
| Blood Glucose (7 days) | | | | |
| Baseline: SD vs. 24 h: KD | 20.45 | 2.876 to 38.03 | Yes | ** |
| Baseline: SD vs. 24 h: SD + KE | 17.64 | 0.05754 to 35.22 | Yes | * |
| Baseline: SD vs. 7 days: SD + KSMCT | 28.55 | 10.97 to 46.12 | Yes | **** |
| Baseline: KD vs. 24 h: SD | −18.74 | −35.95 to −1.534 | Yes | * |
| Baseline: KD vs. 7 days: SD + KSMCT | 25.27 | 7.694 to 42.85 | Yes | *** |
| Baseline: SD + KE vs. 24 h: KD | 24 | 6.421 to 41.58 | Yes | *** |
| Baseline: SD + KE vs. 24 h: SD + KE | 21.18 | 3.603 to 38.76 | Yes | ** |
| Baseline: SD + KE vs. 7 days: SD + KSMCT | 32.09 | 14.51 to 49.67 | Yes | **** |
| Baseline: SD + KS vs. 24 h: SD | −19.25 | −36.08 to −2.420 | Yes | * |
| Baseline: SD + KS vs. 7 days: SD + KSMCT | 24.77 | 7.556 to 41.97 | Yes | *** |
| Baseline: SD + KSMCT vs. 24 h: KD | 27.09 | 9.512 to 44.67 | Yes | **** |
| Baseline: SD + KSMCT vs. 24 h: SD + KE | 24.27 | 6.694 to 41.85 | Yes | *** |
| Baseline: SD + KSMCT vs. 7 days: SD + KSMCT | 35.18 | 17.60 to 52.76 | Yes | **** |
| 24 h: SD vs. 24 h: KD | 35.92 | 18.72 to 53.13 | Yes | **** |
| 24 h: SD vs. 24 h: SD + KE | 33.11 | 15.90 to 50.31 | Yes | **** |
| 24 h: SD vs. 7 days: KD | 19.83 | 2.181 to 37.49 | Yes | * |
| 24 h: SD vs. 7 days: SD + KS | 18.92 | 1.716 to 36.13 | Yes | * |
| 24 h: SD vs. 7 days: SD + KSMCT | 44.02 | 26.81 to 61.22 | Yes | **** |
| 24 h: KD vs. 24 h: SD + KS | −29 | −46.58 to −11.42 | Yes | **** |
| 24 h: KD vs. 24 h: SD + KSMCT | −25.45 | −43.03 to −7.876 | Yes | *** |
| 24 h: KD vs. 7 days: SD | −24.09 | −41.30 to −6.882 | Yes | *** |
| 24 h: KD vs. 7 days: SD + KE | −25.84 | −45.00 to −6.685 | Yes | *** |
| 24 h: SD + KE vs. 24 h: SD + KS | −26.18 | −43.76 to −8.603 | Yes | **** |
| 24 h: SD + KE vs. 24 h: SD + KSMCT | −22.64 | −40.22 to −5.058 | Yes | ** |
| 24 h: SD + KE vs. 7 days: SD | −21.27 | −38.48 to −4.064 | Yes | ** |
| 24 h: SD + KE vs. 7 days: SD + KE | −23.02 | −42.18 to −3.867 | Yes | ** |
| 24 h: SD + KS vs. 7 days: SD + KSMCT | 37.09 | 19.51 to 54.67 | Yes | **** |
| 24 h: SD + KSMCT vs. 7 days: SD + KSMCT | 33.55 | 15.97 to 51.12 | Yes | **** |
| 7 days: SD vs. 7 days: SD + KSMCT | 32.18 | 14.97 to 49.39 | Yes | **** |
| 7 days: KD vs. 7 days: SD + KSMCT | 24.18 | 6.169 to 42.19 | Yes | *** |
| 7 days: SD + KE vs. 7 days: SD + KSMCT | 33.93 | 14.78 to 53.09 | Yes | **** |
| 7 days: SD + KS vs. 7 days: SD + KSMCT | 25.09 | 7.512 to 42.67 | Yes | *** |

TABLE 2-continued

| Blood βHB (7 days) | | | | |
|---|---|---|---|---|
| Tukey's multiple comparisons test | Mean Diff. | 95% CI of diff. | Significant? | Summary |
| Before: SD vs. After: SD | −25.58 | −49.81 to −1.357 | Yes | * |
| Before: KD vs. After: SD | −42.92 | −67.14 to −18.69 | Yes | **** |
| Before KD vs. After: SD + KSMCT | −27.39 | −52.16 to −2.623 | Yes | * |
| Before: SD + KE vs. After: SD | −33.75 | −57.98 to −9.524 | Yes | *** |
| Before: SD + KS vs. After: SD | −40.83 | −65.06 to −16.61 | Yes | **** |
| Before: SD + KS vs. After: SD + KSMCT | −25.31 | −50.08 to −0.5401 | Yes | * |
| Before: SD + KSMCT vs. After: SD | −29.17 | −53.39 to −4.941 | Yes | ** |
| After: SD vs. After: KD | 38.74 | 13.33 to 64.15 | Yes | *** |
| After: SD vs. After: SD + KE | 37.03 | 10.86 to 63.19 | Yes | *** |
| After: SD vs. After: SD + KS | 48.25 | 23.48 to 73.02 | Yes | **** |
| After: SD + KS vs. After: SD + KSMCT | −32.73 | −58.03 to −7.424 | Yes | ** |

After 7 days of gavaging, blood βHB was elevated in SD+KE, SD+KS groups in WAG/Rij rats (FIG. 3C) compared to baseline. In SPD rats, blood βHB was also elevated in all treatment groups compared to baseline (except KD group) and compared to control group as well (FIG. 2C, Table 2).

C. Ketone Supplementations and Blood Glucose Levels

In SPD rats after chronic and sub-chronic ketone treatments, blood glucose levels were lower at 24 hours in SD, KD, SD+KS, SD+KE groups compared to baseline, and were lower in KD, SD+KE and SD+KSMCT groups compared to the control group (FIG. 2D).

In SPD rats after 7 days of oral gavaging, blood glucose was lower in SD+KSMCT compared to control and to baseline (FIG. 2D).

After 13 weeks, blood glucose increased in SD+KSMCT group compared to the baseline (FIG. 1D).

D. Differences in Changes of Blood Ketone and Glucose Levels Between the Two Animal Models There was significant difference in both βHB and glucose levels between the two animal models at baseline (Table 3). While the blood glucose and βHB levels in SPD SD+KE group did not change from baseline to 7 days, there was a significant difference in blood βHB between baseline and 7 days in SPD SD+KS, WAG/Rij SD+KE and WAG/Rij SD+KS groups. After 7 days, there was a significant difference in βHB between SPD SD+KE and SPD SD+KS groups, but not between WAG/Rij SD+KE and WAG/Rij SD+KS groups nor was there a difference in their glucose levels. Both βHB and glucose levels were significantly different between SPD and WAG/Rij animals at 7 days (Table 3).

TABLE 3

| Compare S-D to WagRij | |
|---|---|
| Table Analyzed | βHB |
| Two-way ANOVA | Ordinary |
| Alpha | 0.05 |

| Source of Variation | % of total variation | P value | P value summary | Significant? |
|---|---|---|---|---|
| Interaction | 4.552 | 0.0005 | *** | Yes |
| Row Factor | 25.48 | <0.0001 | **** | Yes |
| Column Factor | 54.75 | <0.0001 | **** | Yes |

| ANOVA table | SS | DF | MS | F (DFn, DFd) | P value |
|---|---|---|---|---|---|
| Interaction | 0.6132 | 3 | 0.2044 | F (3, 67) = 6.708 | P = 0.0005 |
| Row Factor | 3.433 | 1 | 3.433 | F (1, 67) = 112.7 | P < 0.0001 |
| Column Factor | 7.375 | 3 | 2.458 | F (3, 67) = 80.68 | P < 0.0001 |
| Residual | 2.042 | 67 | 0.03047 | | |
| Number of missing values | 21 | | | | |
| Compare cell means regardless of rows and columns | | | | | |
| Number of families | 1 | | | | |
| Number of comparisons per family | 28 | | | | |
| Alpha | 0.05 | | | | |

| Tukey's multiple comparisons test | Mean Diff. | 95% CI of diff. | Significant? | Summary |
|---|---|---|---|---|
| Baseline: S-D (SD + KE) vs. Baseline: S-D (SD + KS) | −0.03485 | −0.2628 to 0.1931 | No | ns |
| Baseline: S-D (SD + KE) vs. Baseline: WR (SD + KE) | −0.4917 | −0.7409 to −0.2424 | Yes | **** |
| Baseline: S-D (SD + KE) vs. Baseline: WR (SD + KS) | −0.5042 | −0.7534 to −0.2549 | Yes | **** |
| Baseline: S-D (SD + KE) vs. 7 days: S-D (SD + KE) | −0.1389 | −0.3797 to 0.1019 | No | ns |

TABLE 3-continued

| Compare S-D to WagRij | | | | |
|---|---|---|---|---|
| Baseline: S-D (SD + KE) vs. 7 days: S-D (SD + KS) | −0.4803 | −0.7083 to −0.2523 | Yes | **** |
| Baseline: S-D (SD + KE) vs. 7 days: WR (SD + KE) | −1.104 | −1.353 to −0.8549 | Yes | **** |
| Baseline: S-D (SD + KE) vs. 7 days: WR (SD + KS) | −1.042 | −1.291 to −0.7924 | Yes | **** |
| Baseline: S-D (SD + KS) vs. Baseline: WR (SD + KE) | −0.4568 | −0.7106 to −0.2030 | Yes | **** |
| Baseline: S-D (SD + KS) vs. Baseline: WR (SD + KS) | −0.4693 | −0.7231 to −0.2155 | Yes | **** |
| Baseline: S-D (SD + KS) vs. 7 days: S-D (SD + KE) | −0.104 | −0.3495 to 0.1414 | No | ns |
| Baseline: S-D (SD + KS) vs. 7 days: S-D (SD + KS) | −0.4455 | −0.6783 to −0.2126 | Yes | **** |
| Baseline: S-D (SD + KS) vs. 7 days: WR (SD + KE) | −1.069 | −1.323 to −0.8155 | Yes | **** |
| Baseline: S-D (SD + KS) vs. 7 days: WR (SD + KS) | −1.007 | −1.261 to −0.7530 | Yes | **** |
| Baseline: WR (SD + KE) vs. Baseline: WR (SD + KS) | −0.0125 | −0.2856 to 0.2606 | No | ns |
| Baseline: WR (SD + KE) vs. 7 days: S-D (SD + KE) | 0.3528 | 0.08740 to 0.6182 | Yes | ** |
| Baseline: WR (SD + KE) vs. 7 days: S-D (SD + KS) | 0.01136 | −0.2424 to 0.2651 | No | ns |
| Baseline: WR (SD + KE) vs. 7 days: WR (SD + KE) | −0.6125 | −0.8856 to −0.3394 | Yes | **** |
| Baseline: WR (SD + KE) vs. 7 days: WR (SD + KS) | −0.55 | −0.8231 to −0.2769 | Yes | **** |
| Baseline: WR (SD + KS) vs. 7 days: S-D (SD + KE) | 0.3653 | 0.09990 to 0.6307 | Yes | ** |
| Baseline: WR (SD + KS) vs. 7 days: S-D (SD + KS) | 0.02386 | −0.2299 to 0.2776 | No | ns |
| Baseline: WR (SD + KS) vs. 7 days: WR (SD + KE) | −0.6 | −0.8731 to −0.3269 | Yes | **** |
| Baseline: WR (SD + KS) vs. 7 days: WR (SD + KS) | −0.5375 | −0.8106 to −0.2644 | Yes | **** |
| 7 days: S-D (SD + KE) vs. 7 days: S-D (SD + KS) | −0.3414 | −0.5869 to −0.09594 | Yes | ** |
| 7 days: S-D (SD + KE) vs. 7 days: WR (SD + KE) | −0.9653 | −1.231 to −0.6999 | Yes | **** |
| 7 days: S-D (SD + KE) vs. 7 days: WR (SD + KS) | −0.9028 | −1.168 to −0.6374 | Yes | **** |
| 7 days: S-D (SD + KS) vs. 7 days: WR (SD + KE) | −0.6239 | −0.8776 to −0.3701 | Yes | **** |
| 7 days: S-D (SD + KS) vs. 7 days: WR (SD + KS) | −0.5614 | −0.8151 to −0.3076 | Yes | **** |
| 7 days: WR (SD + KE) vs. 7 days: WR (SD + KS) | 0.0625 | −0.2106 to 0.3356 | No | ns |

| | |
|---|---|
| Table Analyzed | Glucose |
| Two-way ANOVA | Ordinary |
| Alpha | 0.05 |

| Source of Variation | % of total variation | P value | P value summary | Significant? |
|---|---|---|---|---|
| Interaction | 0.6162 | 0.7389 | ns | No |
| Row Factor | 0.9674 | 0.1641 | ns | No |
| Column Factor | 66.21 | <0.0001 | **** | Yes |

| ANOVA table | SS | DF | MS | F (DFn, DFd) | P value |
|---|---|---|---|---|---|
| Interaction | 93.28 | 3 | 31.09 | F (3, 66) = 0.4205 | P = 0.7389 |
| Row Factor | 146.4 | 1 | 146.4 | F (1, 66) = 1.980 | P = 0.1641 |
| Column Factor | 10022 | 3 | 3341 | F (3, 66) = 45.18 | P < 0.0001 |
| Residual | 4880 | 66 | 73.95 | | |
| Number of missing values | 22 | | | | |
| Compare cell means regardless of rows and columns | | | | | |
| Number of families | 1 | | | | |
| Number of comparisons per family | 28 | | | | |
| Alpha | 0.05 | | | | |

TABLE 3-continued

| Compare S-D to WagRij | | | | |
|---|---|---|---|---|
| Tukey's multiple comparisons test | Mean Diff. | 95% CI of diff. | Significant? | Summary |
| Baseline: S-D (SD + KE) vs. Baseline: S-D (SD + KS) | 7.326 | −3.910 to 18.56 | No | ns |
| Baseline: S-D (SD + KE) vs. Baseline: WR (SD + KE) | 28.41 | 15.90 to 40.92 | Yes | **** |
| Baseline: S-D (SD + KE) vs. Baseline: WR (SD + KS) | 28.78 | 16.28 to 41.29 | Yes | **** |
| Baseline: S-D (SD + KE) vs. 7 days: S-D (SD + KE) | −1.841 | −14.35 to 10.67 | No | ns |
| Baseline: S-D (SD + KE) vs. 7 days: S-D (SD + KS) | 7 | −4.478 to 18.48 | No | ns |
| Baseline: S-D (SD + KE) vs. 7 days: WR (SD + KE) | 25.66 | 13.15 to 38.17 | Yes | **** |
| Baseline: S-D (SD + KE) vs. 7 days: WR (SD + KS) | 22.28 | 9.777 to 34.79 | Yes | **** |
| Baseline: S-D (SD + KS) vs. Baseline: WR (SD + KE) | 21.08 | 8.797 to 33.37 | Yes | **** |
| Baseline: S-D (SD + KS) vs. Baseline: WR (SD + KS) | 21.46 | 9.172 to 33.74 | Yes | **** |
| Baseline: S-D (SD + KS) vs. 7 days: S-D (SD + KE) | −9.167 | −21.45 to 3.119 | No | ns |
| Baseline: S-D (SD + KS) vs. 7 days: S-D (SD + KS) | −0.3258 | −11.56 to 10.91 | No | ns |
| Baseline: S-D (SD + KS) vs. 7 days: WR (SD + KE) | 18.33 | 6.047 to 30.62 | Yes | *** |
| Baseline: S-D (SD + KS) vs. 7 days: WR (SD + KS) | 14.96 | 2.672 to 27.24 | Yes | ** |
| Baseline: WR (SD + KE) vs. Baseline: WR (SD + KS) | 0.375 | −13.08 to 13.83 | No | ns |
| Baseline: WR (SD + KE) vs. 7 days: S-D (SD + KE) | −30.25 | −43.71 to −16.79 | Yes | **** |
| Baseline: WR (SD + KE) vs. 7 days: S-D (SD + KS) | −21.41 | −33.92 to −8.902 | Yes | **** |
| Baseline: WR (SD + KE) vs. 7 days: WR (SD + KE) | −2.75 | −16.21 to 10.71 | No | ns |
| Baseline: WR (SD + KE) vs. 7 days: WR (SD + KS) | −6.125 | −19.58 to 7.334 | No | ns |
| Baseline: WR (SD + KS) vs. 7 days: S-D (SD + KE) | −30.63 | −44.08 to −17.17 | Yes | **** |
| Baseline: WR (SD + KS) vs. 7 days: S-D (SD + KS) | −21.78 | −34.29 to −9.277 | Yes | **** |
| Baseline: WR (SD + KS) vs. 7 days: WR (SD + KE) | −3.125 | −16.58 to 10.33 | No | ns |
| Baseline: WR (SD + KS) vs. 7 days: WR (SD + KS) | −6.5 | −19.96 to 6.959 | No | ns |
| 7 days: S-D (SD + KE) vs. 7 days: S-D (SD + KS) | 8.841 | −3.667 to 21.35 | No | ns |
| 7 days: S-D (SD + KE) vs. 7 days: WR (SD + KE) | 27.5 | 14.04 to 40.96 | Yes | **** |
| 7 days: S-D (SD + KE) vs. 7 days: WR (SD + KS) | 24.13 | 10.67 to 37.58 | Yes | **** |
| 7 days: S-D (SD + KS) vs. 7 days: WR (SD + KE) | 18.66 | 6.152 to 31.17 | Yes | *** |
| 7 days: S-D (SD + KS) vs. 7 days: WR (SD + KS) | 15.28 | 2.777 to 27.79 | Yes | ** |
| 7 days: WR (SD + KE) vs. 7 days: WR (SD + KS) | −3.375 | −16.83 to 10.08 | No | ns |

E. Body Weight Changes During Ketone Supplementation

Figure 1F:
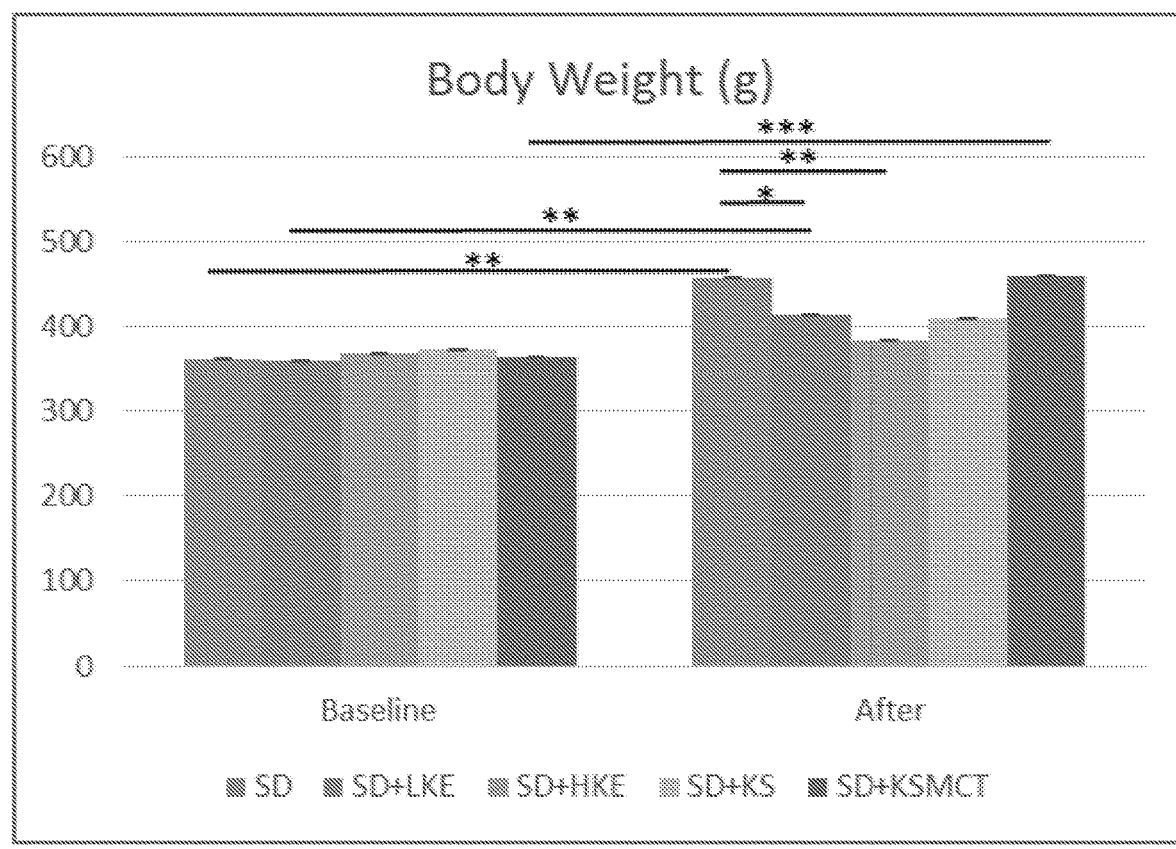
FIG. 1F is a graphical illustration showing that body weight was higher in SD+LKE and SD+HKE groups, compared to control at week 13, while all body weight increased, except SD+HKE and SD+KS, compared to baseline.

After chronic feeding, the body weight of SPD rats was lower in SD+HKE group compared to the control. The body weight increased in SD and SD+KSMCT groups, compared to their baseline (FIG. 1F, Table 1). After 7 days of treatment the body weight of SPD rats increased in SD group, compared to its baseline. The body weight was lower in all treatment groups except SD+KSMCT after 7 days compared to control (FIG. 2E, Table 2). In WAG/Rij rats the body weight did not change significantly in either group during the treatment period (FIG. 3E).

With these data and results obtained, it can be seen that the current study was able to demonstrate the anxiolytic effect of chronic and sub-chronic ketone supplementation in both SPD and WAG/Rij rats by means of EPM, as measured by less entries to closed arms, more time spent in open arms, more distance travelled in open arms, and delayed latency to entrance to closed arms were measured. The exogenous ketone supplementation tested in the present study increased the open arms exploration in the EPM and increased the latency to enter the closed arms, showing anxiolytic effect Differences could be observed between the effects of different ketone supplements on anxiety. After 7 days treatment, KS reduced the number of entries to the closed arms in both animal models, and it also reduced the time spent in closed arms and increased the time spent in open arms in WAG/Rij rats. The KE increased the time spent in the open arms by SPD animals. After 83 days treatment in SPD animals, both the KS and KSMCT treated rats decreased time spent in the closed arms and increased time spent in the open arms and the center (KS only), increased the distance in open arms, decreased the distance in closed arms, and increased the latency to first entry to closed arms. The LKE reduced the distance in closed arms, and the HKE increased the latency to first entrance to closed arms in SPD animals.

In summary, the KS seemed to be the most efficient compound to reduce anxiety together with KSMCT, but low- and high-dose KE also had a beneficial effect on reducing anxiety. Thus, theoretically, as ketone supplementation may generate similar changes in brain neurotransmitter systems as KD by means of ketosis (FIGS. 1A-1F, 2A-2E, and 3A-3E), chronic and sub-chronic ketone supplementation-provoked anxiolytic effects may be evoked by means of glutamatergic and/or GABAergic as well as adenosinergic system in SPD and WAG/Rij rats. However, the knowledge is not sufficient in the art to explain the mechanism(s) by which ketone supplementation exerts its anti-anxiety effects. Thus, unexpected results were achieved herein when administering ketone supplementation to the rats.

Higher βHB levels were measured before (baseline) and after sub-chronic ketone supplementation in WAG/Rij rats (SD+KE and SD+KS) compared to SPD rats (FIGS. 2C and 3C). This result and the reduced activity of GABAergic system in WAG/Rij rat brain (Luhmann H J, et al. Impairment of intracortical GABAergic inhibition in a rat model of absence epilepsy. Epilepsy Res. 1995 September; 22(1):43-51) may explain that 10 times lower doses of KE and KS (~2.5 g/kg) than applied in SPD rats (~25 g/kg) effectively decreased the anxiety level in WAG/Rij rats. Higher basal ketone levels (and its putative anti-anxiety effects) in WAG/Rij rats may also cause lower basal anxiety levels compared to SPD rats (e.g., WAG/Rij rats spent more time in the open arms compared to SPD rats before ketone supplements) (FIGS. 2B and 3B).

In conclusion, based on the present study, it can be concluded that chronic and sub-chronic administration of exogenous ketone supplementation may be an effective way to reduce anxiety. Achieving nutritional ketosis with exogenous ketone supplementation while maintaining a normal diet might be an alternative to the KD, or may further augment the therapeutic efficacy of the KD. These elevated ketone levels have proven to be effective for alleviating symptoms of GLUT1D syndrome, including behavioral characteristics. The foregoing data and results show that chronic, sub-chronic and acute administration of ketone supplements not only elevated blood ketone levels, but also reduced anxiety-related behavior, which can be highly beneficial for patients managing diseases (e.g., GLUT1D syndrome) with nutritional ketosis. Since achieving nutritional ketosis requires strict dietary restrictions, compliance is a major difficulty in this treatment. The administration of exogenous ketone supplements that increase ketone levels in the blood without dietary restrictions may be an effective option to those willing to reach and stay at the state of nutritional ketosis. Exogenous ketone supplementation provides an alternative method to reduce anxiety for healthy individuals, as well as those who need to maintain nutritional ketosis.

Study 2

Another study was carried out using substantially similar methodologies and procedures as in Study 1, specifically using the EPM test to evaluate anxiety-related behavior in 1-year old SD rats when administered ketone supplementation versus control. FIG. 4A shows that 30 min after single dose administration of ketone supplements, the 1-year old SD rats spent more time in open arms, compared to the control group. Additionally, FIG. 4B shows that ~40 min after single dose administration of ketone supplements and right after completion of 5 min EPM test, all treatment group had significantly elevated βHB levels, compared to the control group. Finally, FIG. 4C shows that ~40 min after single dose administration of ketone supplements and right after completion of 5 min EPM test, the KE group had significantly lower blood glucose level, compared to the control group.

Study 3

It was an object of the current study to determine the effects of ketone supplementation on anxiety-related behavior in SPD and WAG/Rij rats. It was speculated that the ketone supplements reduced anxiety-related behavior not solely by elevating blood ketone levels, but also by effecting the regulation of 5-HT levels. Studies have shown that rats pre-treated with amphetamine exhibited increased anxiety-like behavior on the EPM, which was successfully reversed by paroxetine, a selective serotonin (5-HT) reuptake inhibitor (Tu W, et al. Serotonin in the ventral hippocampus modulates anxiety-like behavior during amphetamine withdrawal. Neuroscience. 2014 Sep. 18; 281C:35-43. doi: 10.1016/j.neuroscience.2014.09.019). Those results suggested that 5-HT levels in the ventral hippocampus are critical for regulating anxiety behavior and that increasing 5-HT levels may be an effective strategy for reducing anxiety (Tu W, et al. Serotonin in the ventral hippocampus modulates anxiety-like behavior during amphetamine withdrawal. Neuroscience. 2014 Sep. 18; 281C:35-43. doi: 10.1016/j.neuroscience.2014.09.019).

Generally, exogenous ketone supplementation was tested by adding to food and feeding chronically for 83 days in SPD rats and administering sub-chronically for 7 days in both rat models by daily intragastric gavage bolus, followed by assessment of anxiety measures on EPM. The groups included standard diet (SD) or SD+ketone supplementation. Low-dose ketone ester (LKE) (1,3-butanediol-acetoacetate diester, ~10 g/kg/day, LKE), high dose ketone ester (HKE) (~25 g/kg/day, HKE), beta-hydroxybutyrate-mineral salt (βHB-S) (~25 g/kg/day, KS), and βHB-S+MCT (~25 g/kg/day, KSMCT) were used as ketone supplementation for chronic administration. To extend the results, exogenous ketone supplements were also tested sub-chronically on SPD rats (KE, KS and KSMCT; 5 g/kg/day) and on WAG/Rij rats (KE, KS and KSMCT; 2.5 g/kg/day).

At the end of treatments behavioral data collection was conducted manually by a blinded observer and with a video-tracking system, after which blood βHB and glucose levels were measured. Ketone supplementation reduced anxiety on EPM as measured by less entries to closed arms (sub-chronic KE and KS: SPD rats and KSMCT: WAG/Rij rats), more time spent in open arms (sub-chronic KE: SPD and KSMCT: WAG/Rij rats; chronic KSMCT: SPD rats), more distance travelled in open arms (chronic KS and KSMCT: SPD rats), and by delayed latency to entrance to closed arms (chronic KSMCT: SPD rats), when compared to control. The data indicated that chronic and sub-chronic ketone supplementation not only elevated blood βHB levels in both animal models, but reduced anxiety-related behavior. It was concluded that ketone supplementation represents a promising anxiolytic strategy through a novel means of inducing nutritional ketosis.

I. Methods

A. Animals

Two months old male SPD (n=87) and eight months old male WAG/Rij (n=32) rats were used in the experiments. The animals were housed at Department of Molecular Pharmacology and Physiology (Hyperbaric Biomedical Research Laboratory, Morsani College of Medicine, University of South Florida, Tampa Fla., USA) and the Department of Zoology (University of West Hungary, Savaria Campus, Szombathely, Hungary). Animals were kept in groups of 2-4 under standard laboratory conditions (12:12 h light-dark cycle, light was on from 08.00 AM to 08.00 PM) in air-conditioned rooms at 22±2° C.

Previous studies showed that the percentage of open arm entries linearly increase with age (Lynn D A, et al. The Ontogeny of Anxiety-Like Behavior in Rats from Adolescence to Adulthood. Developmental Psychobiology. 2010; 52(8):731-739. doi:10.1002/dev.20468) and the aging-related changes in EPM behavior are strain-specific (Ferguson S A, et al. Aging effects on elevated plus maze behavior in spontaneously hypertensive, Wistar-Kyoto and Sprague-Dawley male and female rats. Physiol Behav. 2005 Aug. 7; 85(5):621-8. PubMed PMID: 16043200). Thus, the rats used in the present study involved two strains and animals of different age to minimize or eliminate that variable.

Animal treatment and measuring procedures were performed in accordance with the University of South Florida Institutional Animal Care and Use Committee (IACUC) guidelines (Protocol #0006R) and with the local ethical rules in accordance with the Hungarian Act of Animal Care and Experimentation (1998. XXVIII. Section 243/1998.) in conformity with the regulations for animal experimentation in the European Communities Council Directive of 24 Nov. 1986 (86/609/EEC). All experiments were approved by the University of South Florida Institutional Animal Care and Use Committee and all efforts were made to reduce the number of animals used.

B. Synthesis and Formulation of Ketone Precursors

Ketone ester (KE; 1,3-butanediol-acetoacetate diester) was synthesized as previously described (D'Agostino, D., Pilla, R., Held, H., Landon, C., Puchowicz, M., Brunengraber, H., Ari, C., Arnold, P., and Dean, J. (2013) Therapeutic ketosis with ketone ester delays central nervous system oxygen toxicity seizures in rats. *American Journal of Physiology. Regulatory, integrative and comparative physiology* 304(10):R829-36). Ketone salt (KS, which is $Na^+/K^+$-β-hydroxybutyrate mineral salt) is a novel agent that was mixed into a 50% solution supplying approximately 375 mg/g of pure βHB and 125 mg/g of $Na^+/K^+$ in a 1:1 ratio. Accordingly, each dose of KS would equal ~1000-1500 mg of HB, depending on the weight of the animal. Both KE and KS were developed and synthesized in collaboration with Savind Inc. Human food grade MCT oil (60% caprylic triglyceride/40 capric triglyceride) was purchased from Now Foods (Bloomingdale, Ill., USA). KS was mixed with medium chain triglyceride (MCT) in a 1:1 ratio (KSMCT) at the University of South Florida (USF, USA).

C. Ketone Supplementation

In order to determine the effect of different administration forms, chronic and sub-chronic administration were tested. During chronic administration, the ketone supplementation was mixed into the regular rodent chow, which the animals had access to all day for several weeks. During sub-chronic administration, the ketone supplementation was gavaged orally at a single time point daily for only 7 days.

i. Chronic administration

A total of 48 male SPD rats were fed for 83 days with either standard rodent chow (2018 Teklad Global 18% Protein Rodent Diet (#2018), Harlan) (SD/control; n=9) or SD+ketone supplementation. Four treatment animal groups included low-dose KE (~10 g/kg b.w./day, LKE; n=10), high-dose KE (~25 g/kg b.w./day, HKE; n=10), KS (~25 g/kg b.w./day, KS; n=9), and KSMCT (~25 g/kg b.w./day, KSMCT; n=10). Higher dose was used for chronic administration, as the rats were consuming food-integrated ketone supplementation throughout the day, not at a single time point.

ii. Sub-Chronic Administration (Oral Gavage)

In order to familiarize the animals to the intragastric gavage method, water was gavaged for 5 days prior to ketone supplementation. Following the adaptation period to the intragastric gavage method, 39 male SPD rats were fed with SD (SD/control group; n=11), described in previous studies (Poff et al., 2013) and gavaged daily with 5 g/kg b.w./day water (SD/control; n=11) or ketone supplements KE (n=9), KS (n=9), KSMCT (n=10) sub-chronically for 7 days.

In addition, following the adaptation period to the intragastric gavage method, WAG/Rij male rats (n=32) were fed with SD and gavaged sub-chronically with ~2.5 g/kg b.w./day water (SD/control; n=8), KE (n=8), KS (n=8) or KSMCT (n=8) for 7 days. For the sub-chronic gavage administration, the gavage dose was used that induced desired elevation of blood ketone based on the current inventors' previous studies (Kesl et al. 2016).

D. Anxiety Assay

EPM (Coulbourn Instruments) was used to assess anxiety-related behavior of the rats after 83 days of chronic feeding or after 7 days of oral gavage. EPM experiments were carried out under non-stress conditions (in dimly lit and quiet room) between 12.00 and 14.00 hours.

The rats were transferred in their home cage to the experimental room 30 min prior to beginning the experiment. Briefly, rats were placed in the intersection of the four arms of the EPM, facing the open arm opposite to where the experimenter was and their behavior was recorded for 5 minutes. The amount of time spent and number of entries made on the open arms, closed arms and the center zones were video recorded. Latency to entry into the closed arms and the distance travelled in each zones was also measured in chronically treated SPD rats. Only those behaviors are discussed at each experimental scenario where significant difference was found. At the end of the 5-minute test, the rats were removed from the maze and placed back into their home cage. The maze was cleaned with 70% alcohol and after it with tap water and dried with paper towel between rats. The primary method for data collection was a video-tracking system with computer interface and video camera (SMART V3.0 PLATFORM, Panlab, Harvard Apparatus, USA), to automatically collect behavioral data in SPD rats. A blinded observer was present in the testing room separated from the maze by a curtain, and collected EPM data in both SPD and WAG/Rij animals.

E. Blood Analyses and Weight Measurement

In the chronic feeding study, blood βHB and glucose levels were measured 24 hours before the $1^{st}$ day of ketone treatments (baseline levels) and at the $13^{th}$ week after the EPM experiment. In the 7-day oral gavage studies, blood βHB and glucose levels were measured 24 hours before the $1^{st}$ day of ketone treatments (baseline levels; SPD and WAG/Rij rats), 24 hours after the first gavage, and 60 min after gavage on the $7^{th}$ day (SPD and WAG/Rij rats). Whole blood samples (10 µL) were taken from the saphenous vein for analysis of blood glucose (mg/dl) and βHB (mmol/l) levels with the commercially available glucose and ketone (βHB) monitoring system Precision Xtra™ (Abbott Laboratories, Abbott Park, Ill., USA).

The body weight of all animals was recorded before the first ketone treatment (before) and on the last day of the ketone treatment (after).

F. Statistics

All data are presented as the mean standard error of the mean (SEM). The effects of ketone supplementations on anxiety-related behavior were compared, as well as on blood βHB and glucose levels to control or/and baseline levels. Data analysis was performed using GraphPad PRISM version 6.0a. Results were considered significant when p<0.05. Significance was determined by one-way ANOVA with Fisher's LSD test for the behavioral data. Blood ketone, blood glucose, and body weight change were compared using a two-way ANOVA with Tukey's multiple comparisons test.

II. Results

A. Ketone Supplementation Reduced Anxiety on Elevated Plus Maze i. More Time Spent in Open Arms with Ketone Supplements After chronic feeding of ketone supplementation in SPD rats the time spent in the open arms was significantly more in KSMCT group (p=0.0094), while time spent in the closed arms was significantly less in LKE, KS and KSMCT groups (p=0.0389, 0.0077 and 0.0019, respectively), compared to the control (SD) in SPD rats. Time spent in the center was significantly more in KS group (p=0.0239) (FIG. 5A).

After 7 days of gavage administration in SPD rats (sub-chronic), the time spent in the open arms increased in the KE group (p=0.0281), whereas time spent in the center decreased in KE, KS and KSMCT groups (p=0.0005, <0.0001 and 0.023, respectively) (FIG. 6A). In WAG/Rij rats the KSMCT treated rats spent more time in the open arms (p=0.0018) and less time in the closed arms (p=0.0003), whereas KE treated rats spent more time in the center (p=0.0027), compared to the control (SD) group (FIG. 7A).

ii. Less Entries to Closed Arms with Ketone Supplements

Entries to the closed arms were less frequent with KE and KS treatment (p=0.0436 and 0.0234, respectively) in SPD and with KSMCT treatment (p=0.0014) in WAG/Rij rat models, respectively, after 7 days of administration (FIGS. 6B and 7B). SPD rats also entered fewer times to the center when treated with KS (FIG. 6A; p=0.0193), compared to control (SD) animals. Conversely, WAG/Rij rats made less entries to open arms in KE treated group (p=0.0318).

iii. More Distance Traveled in Open Arms, Less in Closed Arms and Delayed Latency of Entrance to Closed Arms with Ketone Supplements After chronic feeding in SPD rats, the distance traveled in the open arms was significantly greater in KS and KSMCT groups (p=0.036 and 0.0165, respectively), and distance traveled in the closed arms was significantly less in LKE, KS and KSMCT groups (p=0.0252, 0.00041, and 0.0032, respectively), compared to the control (SD). Distance traveled in the center was more in KS and KSMCT groups (p=0.0206 and 0.0482, respectively; FIG. 5B).

The latency to first entrance of closed arms was significantly greater in KSMCT group after chronic feeding (p=0.0038) (FIG. 5C).

B. Elevation of Blood βHB Levels with Ketone Supplements

After 83 days of chronic feeding in SPD rats, blood HB levels remained significantly elevated in HKE, KS and KSMCT groups, compared to control (p=0.0004, <0.0001, and 0.0014, respectively; FIG. 5D) while it decreased in SD compared to baseline (p=0.0307).

Blood βHB levels were elevated in SPD rats after 24 hours of a single gavage in KE group (p=0.0325; FIG. 6C), compared to control.

In SPD rats, βHB was elevated in KSMCT groups at 7 days compared to their level at 24 h and baseline (p<0.0001; FIG. 6C). Blood βHB was also elevated in KS and KSMCT treatment groups compared to control group (p=0.0194 and <0.0001, respectively; FIG. 6C). After 7 days of gavage, blood βHB was elevated in KE, KS and KSMCT groups in WAG/Rij rats (p<0.0001) compared to baseline, 24 hours, and control (FIG. 7C).

C. Ketone Supplementation and Blood Glucose Levels

After 13 weeks of chronic feeding in SPD rats, blood glucose did not change significantly in any groups (FIG. 5E).

However, in SPD rats, after sub-chronic ketone treatments, blood glucose levels were lower at 24 hours in KE group compared to control (p<0.0001; FIG. 6D). After 7 days of oral gavage, blood glucose was lower in KSMCT compared to control, to baseline, and to the level at 24 h in SPD rats (p<0.0001; FIG. 6D).

In WAG/Rij rats, the KE group had lower glucose levels after 24 h, compared to baseline levels (p=0.0064). However, after 7 days, their levels were elevated again, compared to the level at 24 h (p=0.0006) (FIG. 7D). Moreover, glucose levels were also elevated after 7 days compared to 24 h in KSMCT group (FIG. 7D).

D. Differences in Changes of Blood Ketone and Glucose Levels Between the Two Animal Models There was significant difference in βHB levels between the two animal models in KE and KSMCT groups at 7 days only (FIG. 8A). The glucose levels were different between the two animal models in each treatment groups at each of the time points, except in KSMCT group at 7 days (FIG. 8B).

E. Body Weight Changes During Ketone Supplementation

After chronic feeding, the body weight of SPD rats was lower in HKE group compared to the control (p=0.0366). The body weight increased in SD and KSMCT groups, compared to their baseline (p=0.0015, 0.0012; FIG. 5F).

After 7 days of treatment, the body weight of SPD rats increased in SD group, compared to its baseline (p=0.0297). The body weight was lower in KE and KS treatment groups after 7 days, compared to control (p=0.0005 and <0.0001, respectively; FIG. 6E). In WAG/Rij rats, the body weight did not change significantly in either group during the treatment period (FIG. 7E).

Considering the totality of the foregoing results, the current study has demonstrated the anxiolytic effect of chronic (13 week) and sub-chronic (7 days) administration of several forms of ketone supplementation in both SPD and WAG/Rij rats. The ketone supplements tested in this study allowed for a rapid and controlled induction of physiologic ketosis without the need for fasting or severe dietary restrictions. Anxiolytic effect was assessed by means of EPM and evidenced by less entries and time spent in closed arms, more entries and time spent in open arms, more distance travelled in open arms, and delayed/increased latency to entrance into closed arms.

In spite of WAG/Rij rats showing different anxiety behavior compared to SPD rats (e.g., WAG/Rij rats spent approximately equal times in the closed and open arms without ketone supplementation: FIGS. 6A and 7A), sub-chronic ketone supplementation was effective not only in SPD rats but also in WAG/Rij rats (FIGS. 6A-6B and 7A-7B). Thus, the results on WAG/Rij rats strengthened the premise of anxiolytic effect of exogenous ketone supplementation found in SPD rats.

In summary, LKE decreased time spent in closed arms and reduced distance travelled in closed arms after chronic treatment. Moreover, KE increased time spent in open arms, decreased time spent in center and decreased number of entries in closed arms after sub-chronic treatment in SPD rats. KS was proven to be effective in reducing time spent and distance travelled in closed arms and increase distance traveled in open arms after chronic treatment. It also reduced time spent and number of entries to center, while decreasing number of entries in closed arms after sub-chronic treatment in SPD rats. KSMCT effectively increased time spent and distance traveled in open arms and decreased time spent and distance traveled in closed arms, as well as delayed latency to first entrance to closed arms after chronic treatment in SPD rats. In WAG/Rij rats KSMCT successfully increased time spent in open arms and decreased time spent and number of entries in closed arms after sub-chronic treatment. Differences could be observed between the effects of different ketone supplements on anxiety. These results indicate that KS and KSMCT are the most effective after chronic treatment, while KE and KS seem to be the most effective after sub-chronic treatment in rats without pathology (SPD). In rats with pathology (WAG/Rij), KSMCT was the most effective treatment after sub-chronic administration.

Higher βHB levels were measured after sub-chronic ketone supplementation in WAG/Rij rats (KE and KSMCT) compared to SPD rats (FIG. 8A). This result and the reduced activity of GABAergic system in WAG/Rij rat brain (Luhmann et al., 1995) may explain that half doses of KE and KSMCT (~2.5 g/kg b.w./day) than applied in SPD rats (~5 g/kg b.w./day) effectively decreased the anxiety level in WAG/Rij rats. Higher basal ketone levels (and its putative anti-anxiety effects) in WAG/Rij rats may also cause lower basal anxiety levels compared to SPD rats (e.g., WAG/Rij rats spent more time in the open arms compared to SPD rats before ketone supplements) (FIGS. 6A and 7A).

In conclusion, based on the present study, it can be concluded that chronic and sub-chronic administration of exogenous ketone supplementation may be an effective way to reduce anxiety.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

Glossary of Claim Terms

Administer: This term is used herein to refer to the process by which ketone supplementation or a composition comprising a ketone supplement (e.g., ketone ester, ketone salt) as an active agent, are delivered to a patient for therapeutic purposes. Ketone supplementation or the composition of the subject invention can be administered a number of ways including, but not limited to, parenteral (such term referring to intravenous and intra-arterial as well as other appropriate parenteral routes), subcutaneous, peritoneal, inhalation, vaginal, rectal, nasal, or instillation into body compartments. Administration will often depend upon the amount of compound administered, the number of doses, and duration of treatment. In an embodiment, multiple doses of the agent are administered. The frequency of administration of the agent can vary depending on any of a variety of factors, such as extent of anxiety-related behavior, and the like. The duration of administration of the agent, e.g., the period of time over which the agent is administered, can vary, depending on any of a variety of factors, including patient response, etc. The amount of the agent contacted (e.g., administered) can vary according to factors such as the degree of susceptibility of the individual, the age, sex, and weight of the individual, idiosyncratic responses of the individual, the dosimetry, and the like. Detectably effective amounts of the agent of the present disclosure can also vary according to instrument and film-related factors. Optimization of such factors is well within the level of skill in the art, unless otherwise noted.

Anxiety disorder: This term is used herein to refer to a disease or condition that is characterized by inward or outward manifestations of anxiety.

Chronically: This term is used herein to refer to long-term treatment of an individual subject suffering from an anxiety disorder or experiencing anxiety-related behavior, by administering ketone supplementation. In the studies presented herein, a long-term treatment period was considered to be about 83 days.

Exogenous ketone supplementation: This term is used herein to refer to a compound—including BD, ketone salt, ketone ester, or combination thereof or combined with MCT—administered to and ingested by a patient or subject suffering from an anxiety disorder or experiencing anxiety-related behavior.

Patient: This term is used herein to refer to a human or mammal (e.g., mouse, rat, pig, cat, dog, and horse). Typical hosts to which an agent(s) of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

Sub-chronically: This term is used herein to refer to a shorter-term treatment of an individual subject suffering from an anxiety disorder or experiencing anxiety-related behavior, by administering ketone supplementation. In the studies presented herein, a short-term treatment period was considered to be about 7 days. These short-term treatments may be repeated, as needed.

Therapeutically effective amount: This term is used herein to refer to describes concentrations or amounts of components such as agents which are effective for producing an intended result, including preventing further anxiety-related behavior, or treating anxiety-related behavior and related conditions. Compositions according to the present invention may be used to effect a favorable change in anxiety-related behavior, whether that change is an improvement, such as stopping or reversing the behavior, reducing levels of the behavior, or improving the behavior, relieve to some extent one or more of the symptoms of the condition being treated, and/or that amount that will prevent, to some extent, one or more of the symptoms of the condition that the host being treated has or is at risk of developing, or a complete cure of the disease or condition treated.

Treating: This term is used herein to refer to acting upon a condition (e.g., anxiety-related behavior) with an agent (e.g., ketone supplementation) to affect the condition by improving or altering it. The improvement or alteration may include an improvement in symptoms or an alteration in the physiologic pathways associated with the condition. The aforementioned terms cover one or more treatments of a condition in a patient (e.g., a mammal, typically a human or non-human animal of veterinary interest), and includes: (a) reducing the risk of occurrence of the condition in a subject determined to be predisposed to the condition but not yet diagnosed, (b) impeding the development of the condition, and/or (c) relieving the condition, e.g., causing regression of the condition and/or relieving one or more condition symptoms (e.g., reduce anxiety-related behavior).

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of treating a patient suffering from an anxiety disorder, comprising orally administering to the patient a therapeutically effective amount of exogenous ketone supplementation chronically, sub-chronically, or acutely, wherein the ketone supplementation comprises a medium chain triglyceride in combination with a beta hydroxybutyrate mineral salt.

2. The method as in claim 1, wherein the beta-hydroxybutyrate mineral salt is in a concentration of about 0.4 to 25 grams of the salt per kilogram of body weight per day.

3. The method as in claim 1, wherein the beta-hydroxybutyrate mineral salt is admixed with the medium chain triglyceride in a 1:1 ratio.

4. The method as in claim 1, wherein the ketone supplementation is administered chronically.

5. A method of reducing anxiety in a patient or subject, comprising administering to the patient or subject a therapeutically effective amount of exogenous ketone supplementation chronically or sub-chronically, wherein the ketone supplementation comprises a medium chain triglyceride in combination with a beta hydroxybutyrate mineral salt.

6. The method as in claim 5, wherein the ketone supplementation includes the beta hydroxybutyrate mineral salt in a concentration of about 0.4 to 25 grams of the salt per kilogram of body weight per day.

7. The method as in claim 5, wherein the beta hydroxybutyrate mineral salt is admixed with the medium chain triglyceride in a 1:1 ratio.

8. The method as in claim 5, wherein the ketone supplementation is administered chronically.

9. A method of reducing anxiety in a patient or subject, comprising chronically administering to the patient or subject a therapeutically effective amount of exogenous ketone supplementation, wherein the ketone supplementation includes a ketone salt comprising beta-hydroxybutyrate sodium and/or potassium salt admixed with a medium chain triglyceride in a 1:1 ratio, such that a concentration of the beta-hydroxybutyrate-mineral salt is about 0.4-25 grams of the beta-hydroxybutyrate-mineral salt per kilogram of body weight per day and a concentration of the medium chain triglyceride is about 0.4-25 grams of the medium chain triglyceride per kilogram of body weight per day.

10. The method of claim 9, wherein the anxiety disorder is associated with conditioned fear.

* * * * *